US007543239B2

(12) United States Patent
Viswanathan et al.

(10) Patent No.: US 7,543,239 B2
(45) Date of Patent: Jun. 2, 2009

(54) USER INTERFACE FOR REMOTE CONTROL OF MEDICAL DEVICES

(75) Inventors: Raju R. Viswanathan, St. Louis, MO (US); Walter M. Blume, St. Louis, MO (US); Jeffrey M. Garibaldi, St. Louis, MO (US); John Rauch, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 728 days.

(21) Appl. No.: 11/146,413

(22) Filed: Jun. 6, 2005

(65) Prior Publication Data

US 2006/0041180 A1 Feb. 23, 2006

Related U.S. Application Data

(60) Provisional application No. 60/576,946, filed on Jun. 4, 2004.

(51) Int. Cl.
*G06F 3/00* (2006.01)

(52) U.S. Cl. .................................... 715/772; 715/764

(58) Field of Classification Search ................ 715/772, 715/740, 764, 768, 854, 856; 600/11; 128/899
See application file for complete search history.

(56) References Cited

U.S. PATENT DOCUMENTS

| 5,654,864 | A | 8/1997 | Ritter et al. |
| 5,931,818 | A | 8/1999 | Werp et al. |
| 6,014,580 | A | 1/2000 | Blume et al. |
| 6,015,414 | A | 1/2000 | Werp et al. |
| 6,128,174 | A | 10/2000 | Ritter et al. |
| 6,148,823 | A | 11/2000 | Hastings |
| 6,152,933 | A | 11/2000 | Werp et al. |
| 6,157,853 | A | 12/2000 | Blume et al. |
| 6,212,419 | B1 | 4/2001 | Blume et al. |
| 6,241,671 | B1 | 6/2001 | Ritter et al. |
| 6,246,784 | B1 * | 6/2001 | Summers et al. ............ 382/128 |
| 6,277,082 | B1 * | 8/2001 | Gambale ..................... 600/549 |
| 6,292,678 | B1 | 9/2001 | Hall et al. |
| 6,296,604 | B1 | 10/2001 | Garibaldi et al. |
| 6,298,257 | B1 | 10/2001 | Hall et al. |
| 6,304,768 | B1 | 10/2001 | Blume et al. |
| 6,315,709 | B1 | 11/2001 | Garibaldi et al. |
| 6,330,467 | B1 | 12/2001 | Creighton, IV et al. |
| 6,343,936 | B1 * | 2/2002 | Kaufman et al. ............ 434/262 |
| 6,352,363 | B1 | 3/2002 | Munger et al. |
| 6,364,823 | B1 | 4/2002 | Garibaldi et al. |
| 6,375,606 | B1 | 4/2002 | Garibaldi et al. |

(Continued)

OTHER PUBLICATIONS

International Search Report and Written Opinion for corresponding PCT/US05/19880 Date: Sep. 16, 2008 pp. 10.

*Primary Examiner*—Sy D Luu
(74) *Attorney, Agent, or Firm*—Harness, Dickey & Pierce, P.L.C.

(57) ABSTRACT

An interface for remotely controlling a medical device in a patient's body provides a two dimensional display of a three dimensional rendering of the operating region, and allows the user to select the orientation or location of the distal end of the medical device on the display and then operate a navigation system to cause the distal end of the medical device to approximately assume the selected orientation or location.

22 Claims, 64 Drawing Sheets

U.S. PATENT DOCUMENTS

| | | |
|---|---|---|
| 6,385,472 B1 | 5/2002 | Hall et al. |
| 6,401,723 B1 | 6/2002 | Garibaldi et al. |
| 6,428,551 B1 | 8/2002 | Hall et al. |
| 6,459,924 B1 | 10/2002 | Creighton, IV et al. |
| 6,505,062 B1 | 1/2003 | Ritter et al. |
| 6,507,751 B2 | 1/2003 | Blume et al. |
| 6,514,082 B2 * | 2/2003 | Kaufman et al. ............ 434/262 |
| 6,522,909 B1 | 2/2003 | Garibaldi et al. |
| 6,524,303 B1 | 2/2003 | Garibaldi |
| 6,527,782 B2 | 3/2003 | Hogg et al. |
| 6,537,196 B1 | 3/2003 | Creighton, IV et al. |
| 6,538,634 B1 * | 3/2003 | Chui et al. .................. 345/156 |
| 6,542,766 B2 | 4/2003 | Hall et al. |
| 6,562,019 B1 | 5/2003 | Sell |
| 6,630,879 B1 | 10/2003 | Creighton, IV et al. |
| 6,662,034 B2 | 12/2003 | Segner et al. |
| 6,677,752 B1 | 1/2004 | Creighton, IV et al. |
| 6,702,804 B1 | 3/2004 | Ritter et al. |
| 6,733,511 B2 | 5/2004 | Hall et al. |
| 6,755,816 B2 | 6/2004 | Ritter et al. |
| 6,817,364 B2 | 11/2004 | Garibaldi et al. |
| 6,834,201 B2 | 12/2004 | Gillies et al. |
| 6,902,528 B1 | 6/2005 | Garibaldi et al. |
| 6,911,026 B1 | 6/2005 | Hall et al. |
| 6,968,846 B2 | 11/2005 | Viswanathan |
| 6,975,197 B2 | 12/2005 | Creighton, IV |
| 6,980,843 B2 | 12/2005 | Eng et al. |
| 7,008,418 B2 | 3/2006 | Hall et al. |
| 7,010,338 B2 | 3/2006 | Ritter et al. |
| 7,012,603 B2 * | 3/2006 | Chen et al. .................. 345/419 |
| 7,019,610 B2 | 3/2006 | Creighton, IV et al. |
| 7,020,512 B2 | 3/2006 | Ritter et al. |
| 7,066,924 B1 | 6/2006 | Garibaldi et al. |
| 7,148,887 B2 * | 12/2006 | Kaufman et al. ............ 345/419 |
| 7,167,180 B1 * | 1/2007 | Shibolet ...................... 345/474 |
| 7,194,117 B2 * | 3/2007 | Kaufman et al. ............ 382/128 |
| 7,349,563 B2 * | 3/2008 | Kiraly et al. ................ 382/128 |
| 7,372,988 B2 * | 5/2008 | Yoakum-Stover et al. ... 382/154 |
| 2001/0038683 A1 | 11/2001 | Ritter et al. |
| 2002/0019644 A1 | 2/2002 | Hastings et al. |
| 2002/0177789 A1 | 11/2002 | Ferry et al. |
| 2004/0006301 A1 | 1/2004 | Sell et al. |
| 2004/0019447 A1 | 1/2004 | Shachar |
| 2004/0064153 A1 | 4/2004 | Creighton, IV et al. |
| 2004/0068173 A1 * | 4/2004 | Viswanathan ............... 600/407 |
| 2004/0096511 A1 | 5/2004 | Harburn et al. |
| 2004/0133130 A1 | 7/2004 | Ferry et al. |
| 2004/0157082 A1 | 8/2004 | Ritter et al. |
| 2004/0158972 A1 | 8/2004 | Creighton, IV et al. |
| 2004/0186376 A1 | 9/2004 | Hogg et al. |
| 2004/0199074 A1 | 10/2004 | Ritter et al. |
| 2004/0249262 A1 | 12/2004 | Werp et al. |
| 2004/0249263 A1 | 12/2004 | Creighton, IV |
| 2004/0260172 A1 | 12/2004 | Ritter et al. |
| 2005/0020911 A1 | 1/2005 | Viswanathan et al. |
| 2005/0043611 A1 | 2/2005 | Sabo et al. |
| 2005/0065435 A1 * | 3/2005 | Rauch et al. ................ 600/427 |
| 2005/0096589 A1 | 5/2005 | Shachar |
| 2005/0113628 A1 | 5/2005 | Creighton, IV et al. |
| 2005/0113812 A1 | 5/2005 | Viswanathan et al. |
| 2005/0119687 A1 | 6/2005 | Dacey, Jr. et al. |
| 2005/0182315 A1 | 8/2005 | Ritter et al. |
| 2005/0256398 A1 | 11/2005 | Hastings et al. |
| 2006/0009735 A1 | 1/2006 | Viswanathan et al. |
| 2006/0025679 A1 | 2/2006 | Viswanathan et al. |
| 2006/0036125 A1 | 2/2006 | Viswanathan et al. |
| 2006/0036163 A1 | 2/2006 | Viswanathan |
| 2006/0041178 A1 | 2/2006 | Viswanathan et al. |
| 2006/0041179 A1 | 2/2006 | Viswanathan et al. |
| 2006/0041180 A1 | 2/2006 | Viswanathan et al. |
| 2006/0041181 A1 | 2/2006 | Viswanathan et al. |
| 2006/0041245 A1 | 2/2006 | Ferry et al. |
| 2006/0058646 A1 | 3/2006 | Viswanathan |
| 2006/0062450 A1 * | 3/2006 | Yoakum-Stover et al. ... 382/154 |
| 2006/0074297 A1 | 4/2006 | Viswanathan |
| 2006/0079745 A1 | 4/2006 | Viswanathan |
| 2006/0079812 A1 | 4/2006 | Viswanathan |
| 2006/0093193 A1 | 5/2006 | Viswanathan |
| 2006/0094956 A1 * | 5/2006 | Viswanathan ............... 600/431 |
| 2006/0100505 A1 | 5/2006 | Viswanathan |
| 2006/0114088 A1 | 6/2006 | Shachar |
| 2006/0116633 A1 | 6/2006 | Shachar |
| 2006/0144407 A1 | 7/2006 | Aliberto et al. |
| 2006/0144408 A1 | 7/2006 | Ferry |
| 2007/0173689 A1 * | 7/2007 | Ozaki et al. ................. 600/111 |
| 2007/0276225 A1 * | 11/2007 | Kaufman et al. ............ 600/416 |

* cited by examiner

250

Unable to Recall the Vector stored with the point "Mitral Valve10:00".
The Magnetic Field of the MNS was Reduced when the point was stored.
Only Applied fields can be Recalled.

USER INTERFACE FOR REMOTE CONTROL OF MEDICAL DEVICES

CROSS REFERENCE TO RELATED APPLICATIONS

This application claims benefit of U.S. Provisional Application Ser. No. 60/576,946, filed Jun. 4, 2004, incorporated herein by reference

BACKGROUND OF THE INVENTION

This invention relates to the remote navigation of medical devices in a patient's body, and in particular to a user interface for controlling a remote navigation system.

Advances in technology have resulted in systems that allow a physician or other medical professional to remotely control the orientation of the distal of a medical device. It is now fairly routine steer the distal end of a medical device inside a patient's body by manipulating controls on the proximal end of the medical device. Recently magnetic navigation systems have been developed that allow a physician to orient the distal end of a medical device using the field of an external source magnet. Other systems have been discussed for the automated remote orientation of the distal end of a medical device, for example by operating magnetostrictive or electrostrictive elements incorporated into the medical device. However the medical device is oriented, it is still difficult for a physician to visualize the procedure site (which is out of view inside the patient's body), to selected the desired direction in which to orient the distal end of the medical device and communicate the selected direction to the system in order to orient the distal end of the medical device in the selected direction.

SUMMARY OF THE INVENTION

The present invention relates to an interface to facilitate the selection of the desired direction in which to orient the distal end of the medical device and to communicate the selected direction to a navigation system in order to orient the distal end of the medical device in the selected direction. While the present invention is described primarily in connection with a magnetic navigation system, the invention is not so limited, and can be used in connection with other navigation systems, such as those that can orient the distal end of a medical device with mechanical means, electrostrictive elements, magnetostrictive elements, or otherwise.

BRIEF DESCRIPTION OF THE DRAWINGS

Corresponding reference numerals indicate corresponding parts throughout the several views of the drawings.

DETAILED DESCRIPTION OF THE INVENTION

Figure 1:
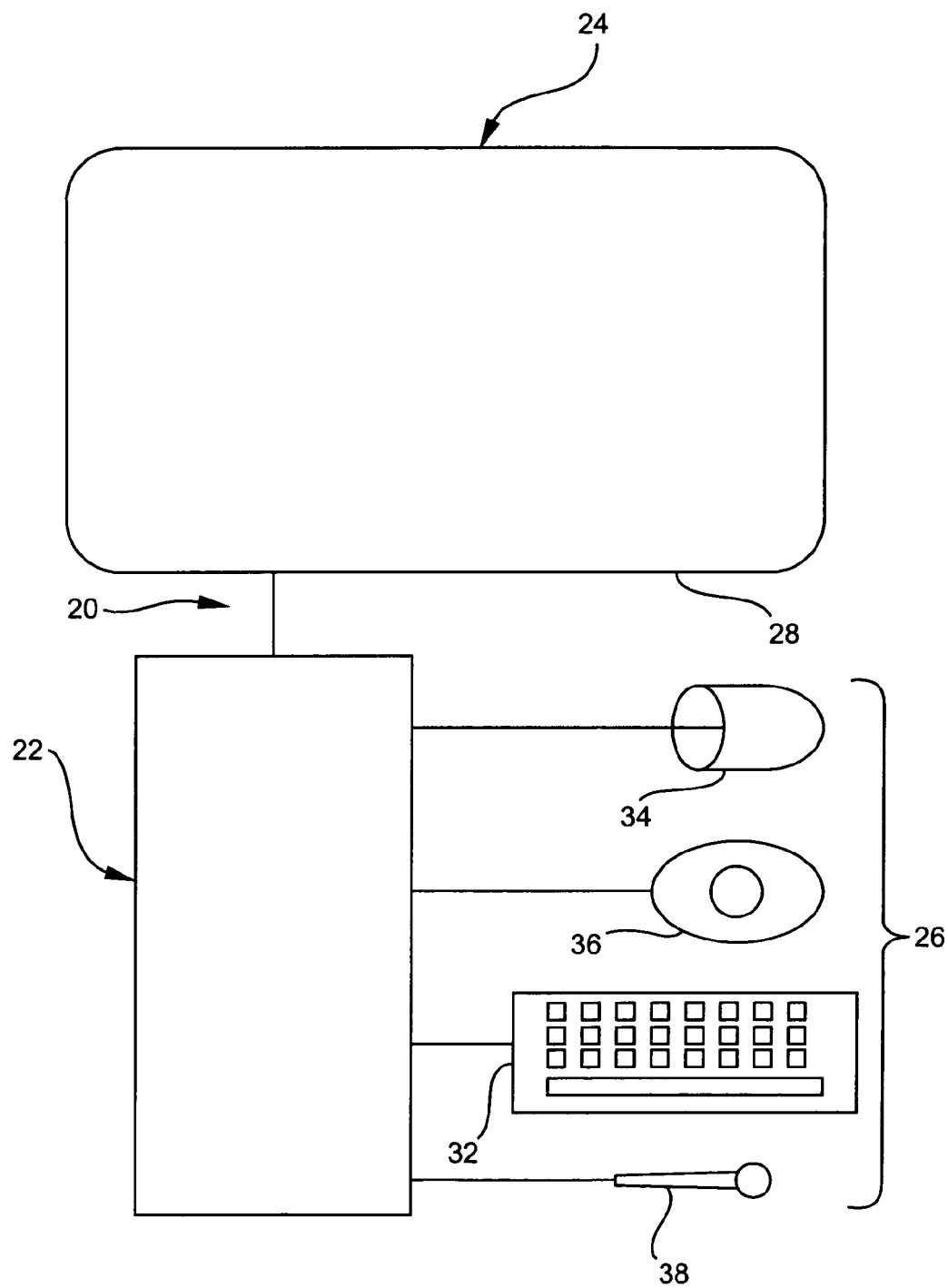
FIG. 1 is a schematic diagram of an interface system according to the principles of this invention.

This invention relates to an interface for a navigation system for orienting the distal end of a medical device inside a patient's body. As shown in FIG. 1 the interface, indicated generally as 20, comprises a processor 22, a display 24, and an input device 26. The display 24 preferably includes at least one monitor 28, which may be a flat panel LCD display which is small, compact, and less prone to interference. The input device 26 may include a keyboard 32, a mouse 34, a track ball 36, microphone 38, or other device for controlling a cursor on the display 24.

Figure 2:
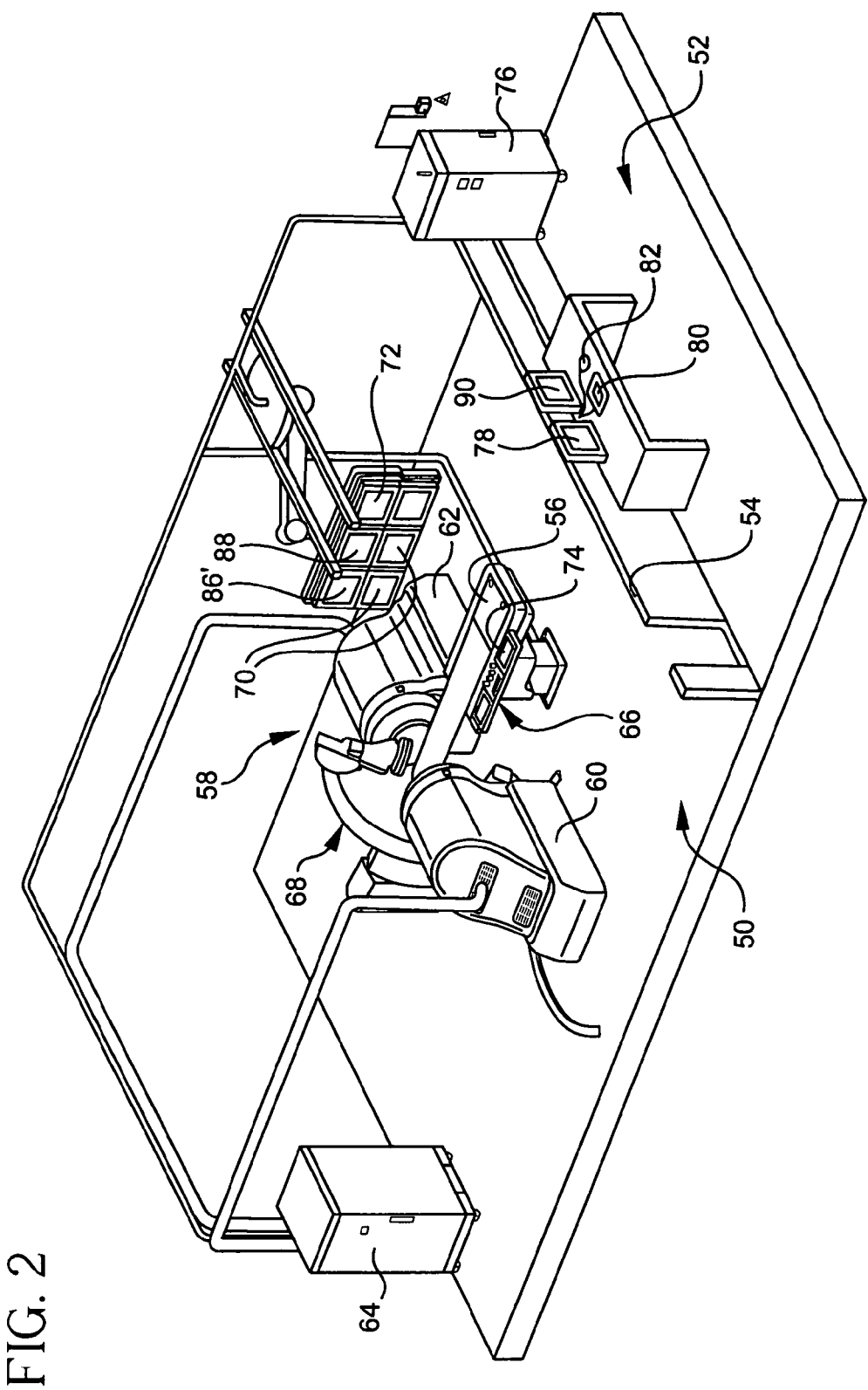
FIG. 2 is a schematic diagram of a possible implementation of the interface for use in controlling a magnetic surgery system.

A possible implementation of an interface system is indicated in FIG. 2, in which components of the interface are distributed in the procedure room 50 where the patient is located, and a control room 52. The control room 52 is preferably adjacent the procedure room 50, and there may be a window 54 between the control room and the procedure room to permit direct observation of the patient, however the control room could be remote from the patient, and with the aid of the present interface, a physician could conduct a procedure on a patient in the procedure from a control room on a different floor, in a different building, or even in a different city.

As shown in FIG. 2, a magnetic surgery suite comprising a patient bed 56, and a magnetic navigation system 58 comprising opposed magnet units 60 and 62 on opposite sides of the patient bed operated by a processor 64 and controlled by controls 66 adjacent the patient 56. An imaging system 68, such as a x-ray imaging on a C-arm, displays images of the operating region on a monitors 70 in the procedure room 50. The interface system of the present invention provides a convenient way for a physician to operate the magnetic navigation system 58 to control the distal end of a medical device in the operating region inside the patient's body.

The interface includes a display on, for example, an LCD monitor 72, and a mouse 74 in the procedure room 50, a processor 76, a display on, for example, monitor 78, a key board 80, and a mouse 82 in the control room 54. Additional displays on monitors 86 and 88 can be provided in the procedure room 50 which integrate images from the imaging system 68 with the interface. One or more additional monitors 90 can be provided in the control room so that the images are available in the control room as well. The monitors 72 and 78 preferably display a multi-pane display.

Figure 3:
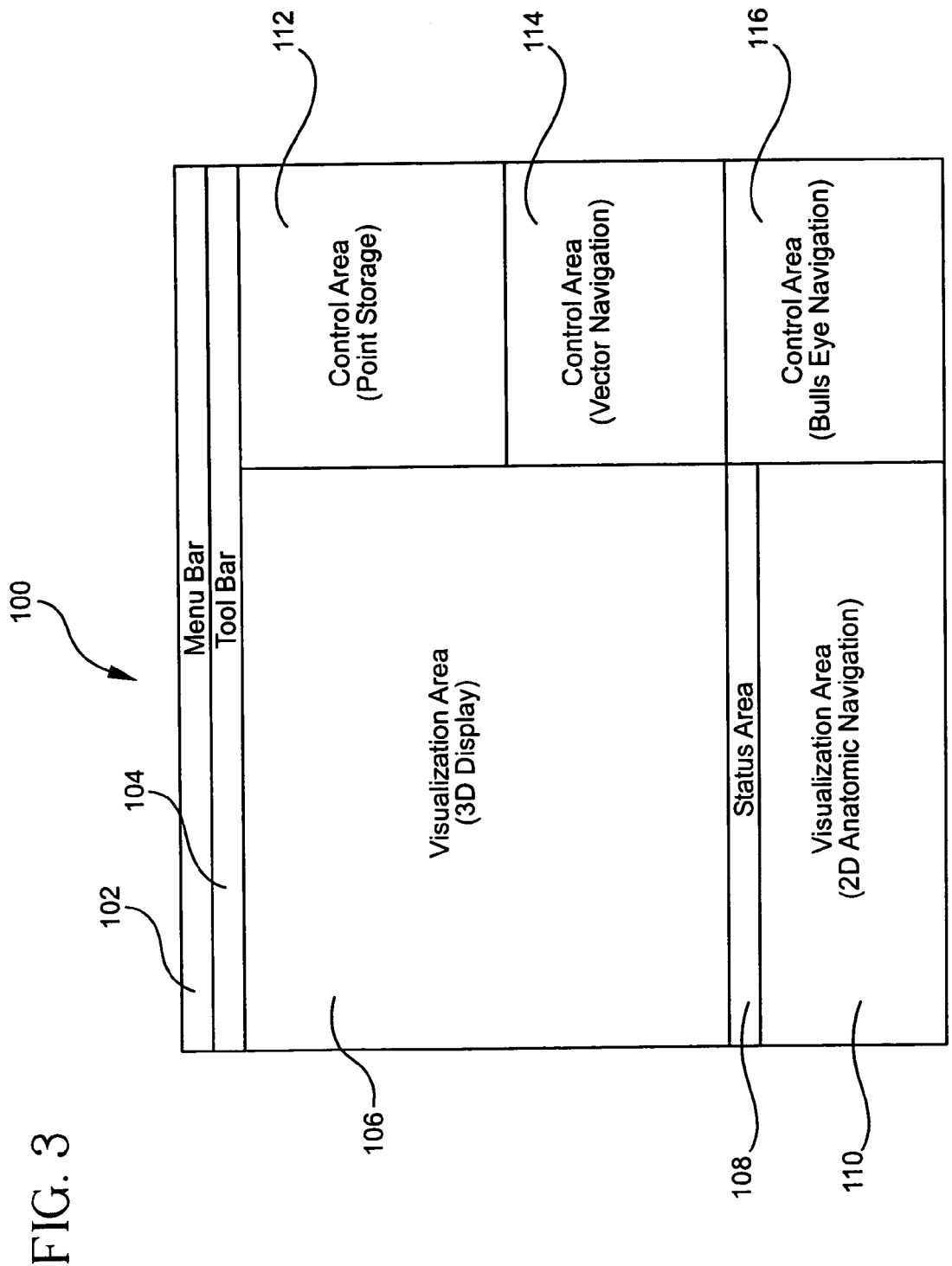
FIG. 3 is a schematic diagram of the display of a first preferred embodiment of the interface of this invention.
Figure 4A:
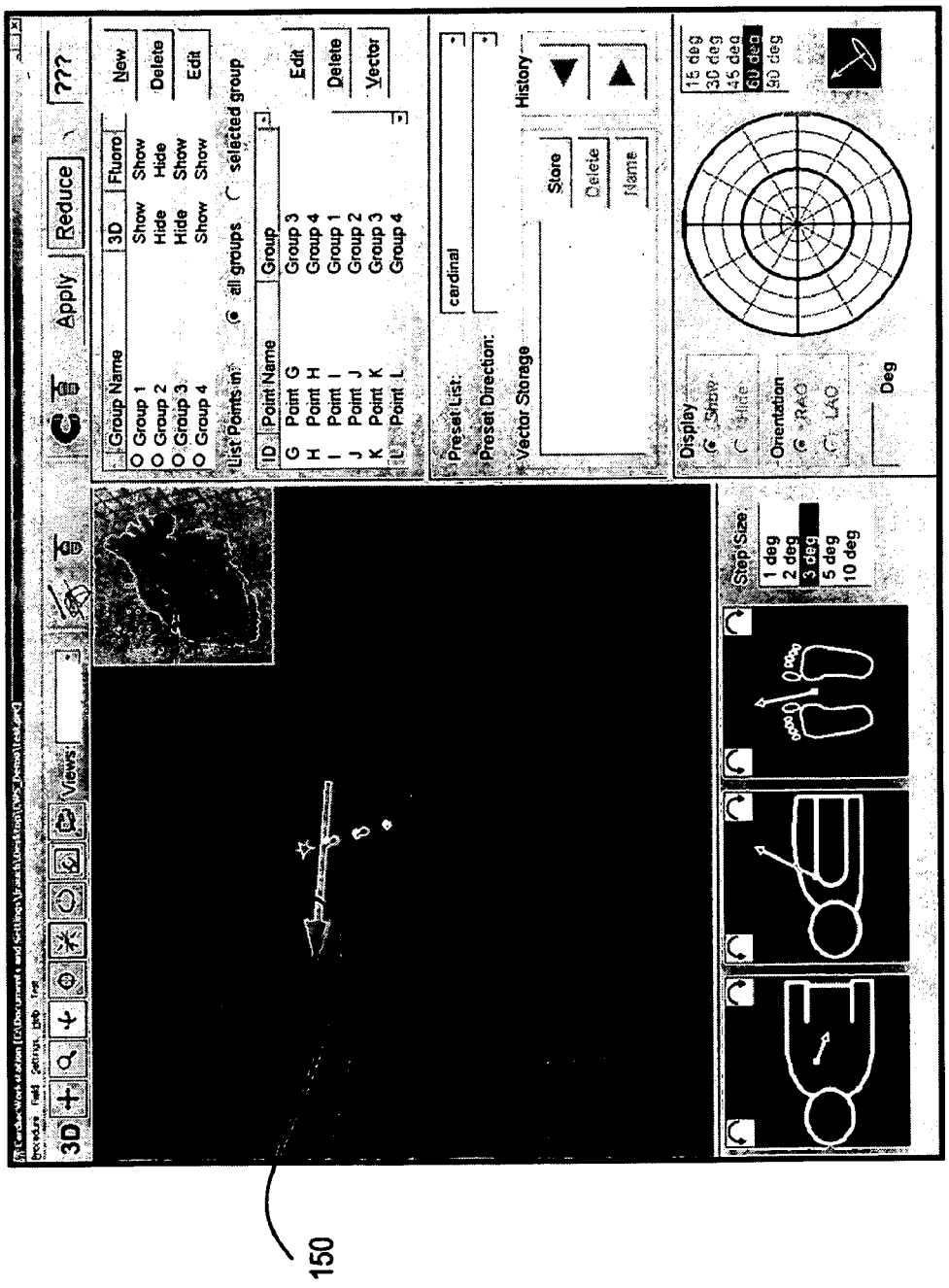
FIG. 4A is a view of the display of the first preferred embodiment of the interface of this invention, showing several points on the 3-D display pane and the desired orientation arrow.
Figure 4B:
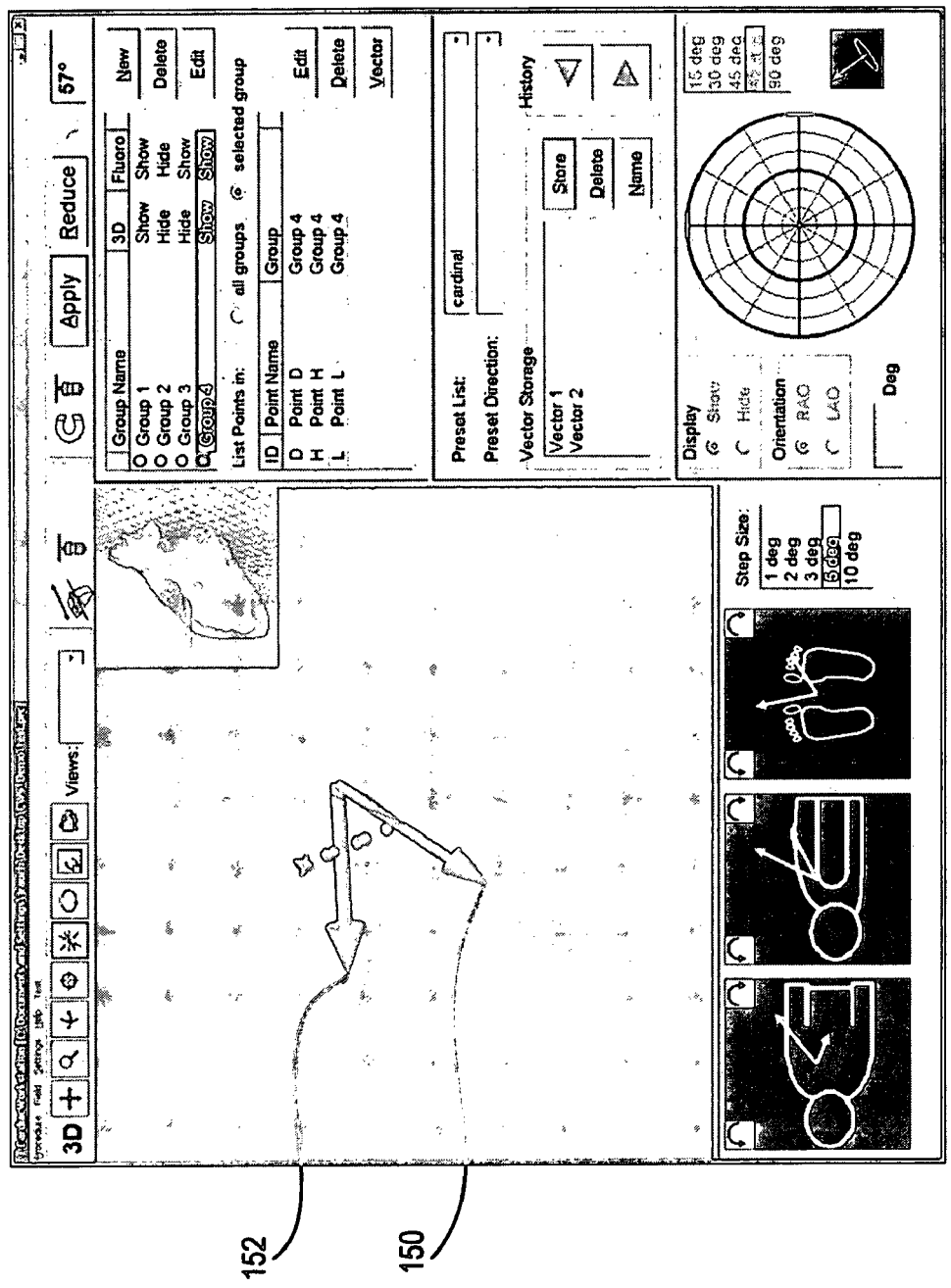
FIG. 4B is a view of the display of the first preferred embodiment of the interface of the invention, showing several points on the 3-D display pane, a current direction vector and a desired direction vector.
Figure 4C:
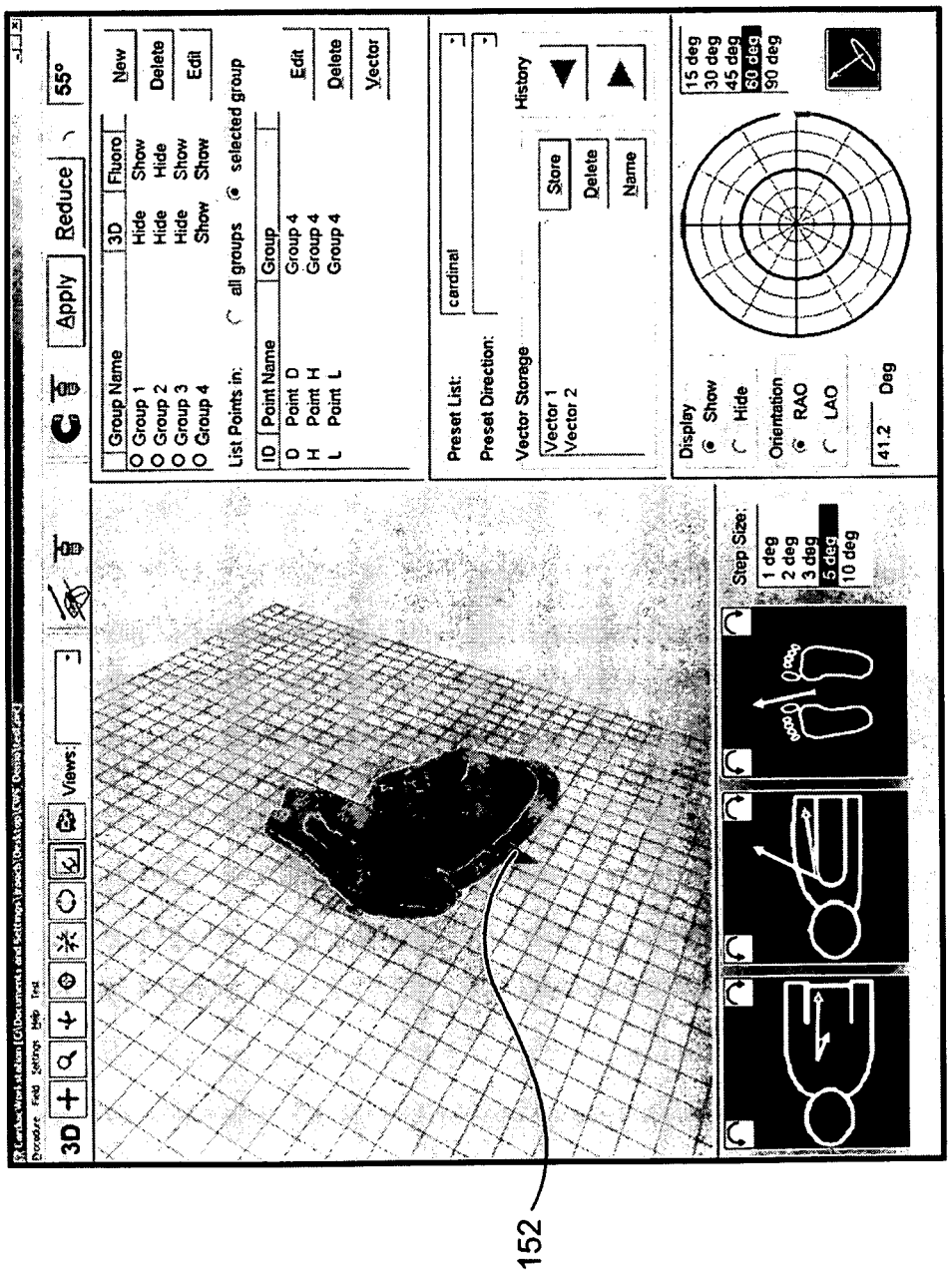
FIG. 4C is a view of the display of the first preferred embodiment of the interface of the invention, showing the anatomical model in the 3-D display pane, with the picture-in-picture feature turned off.
Figure 4D:
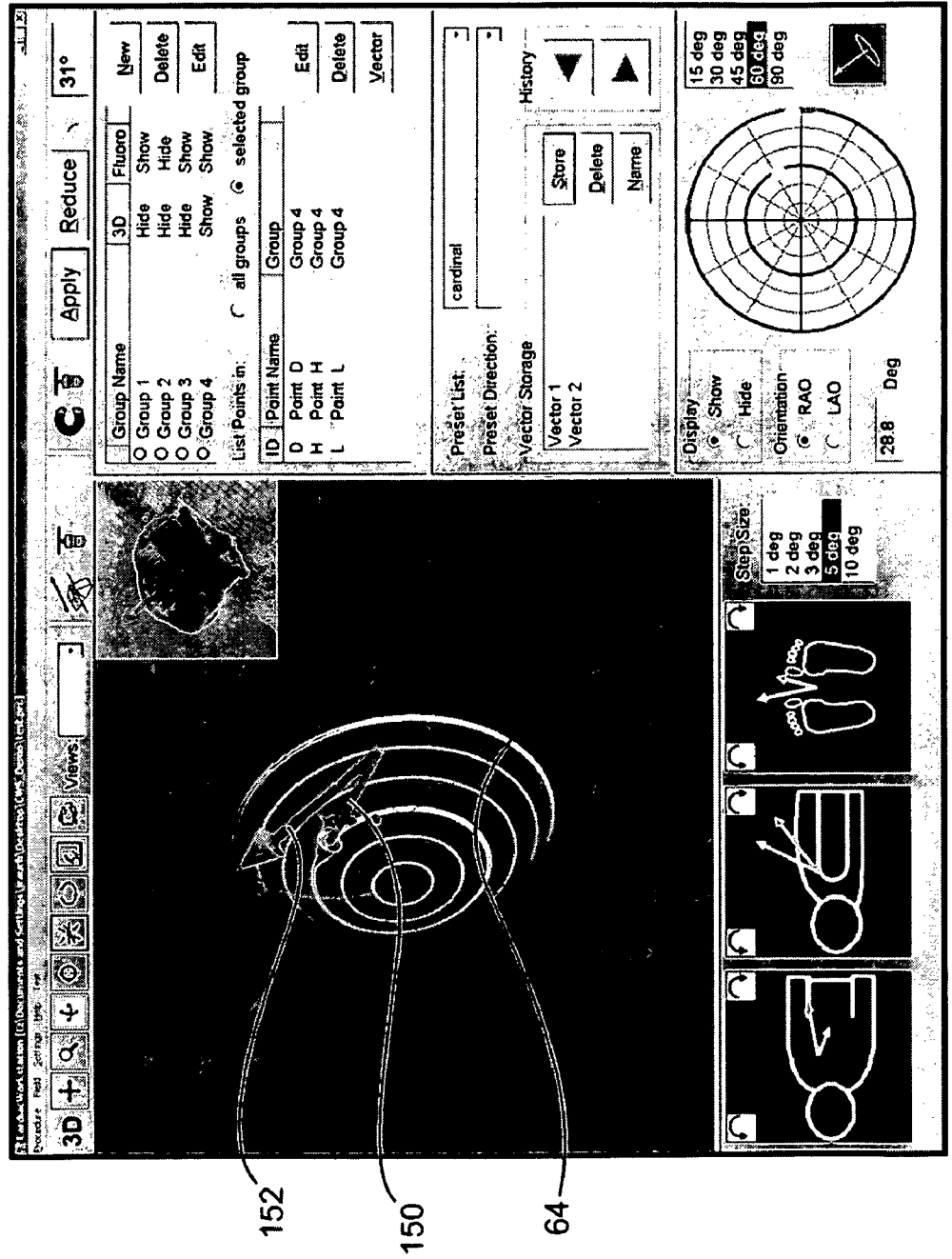
FIG. 4D is a view of the display of the first preferred embodiment of the interface of the invention, showing the bull's eye display in the 3-D display pane.
Figure 4E:
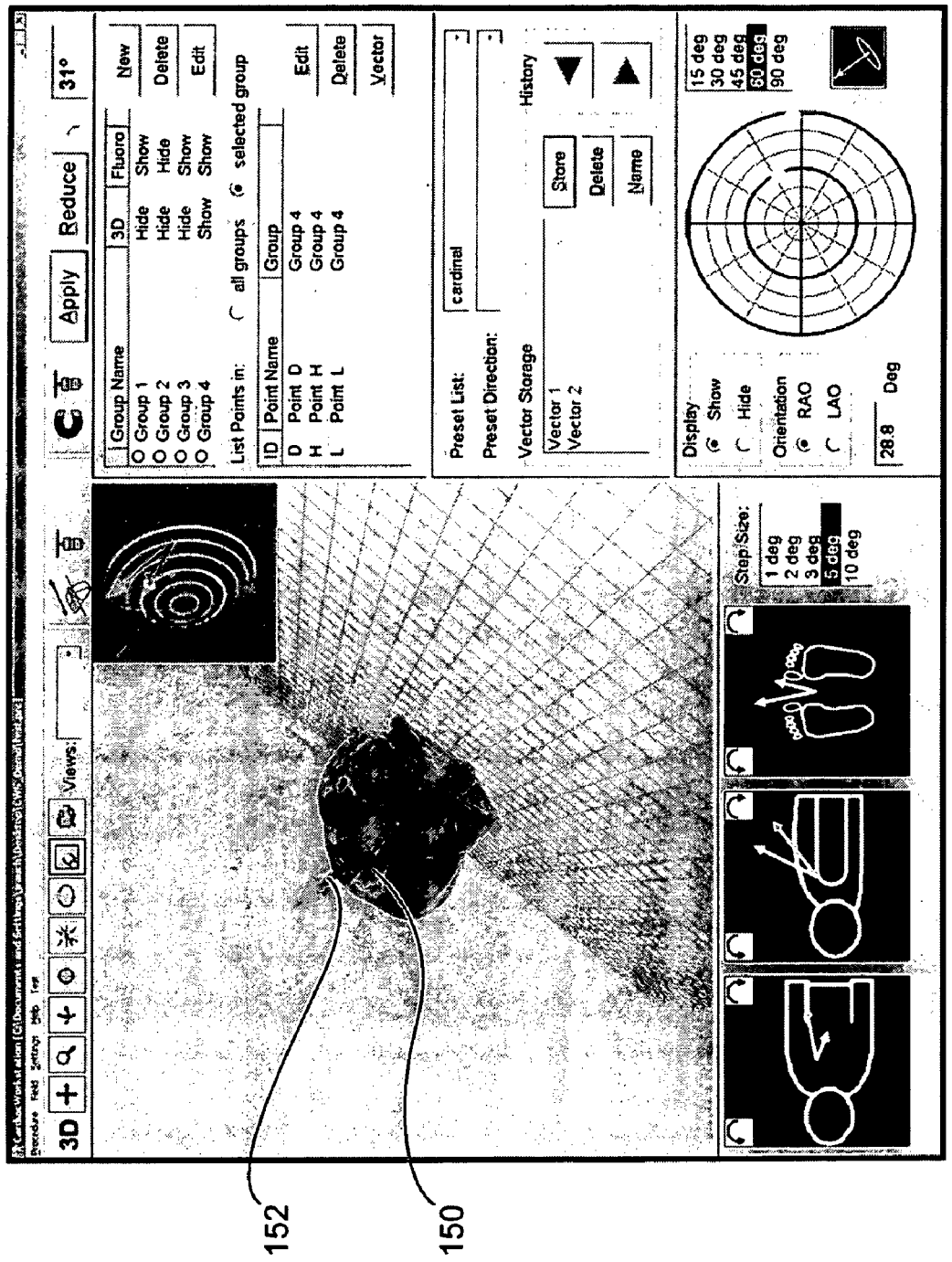
FIG. 4E is a view of the display of the first preferred embodiment of the interface of the invention, showing the bull's eye display in the picture-in-picture portion of the 3-D display pane.
Figure 4F:
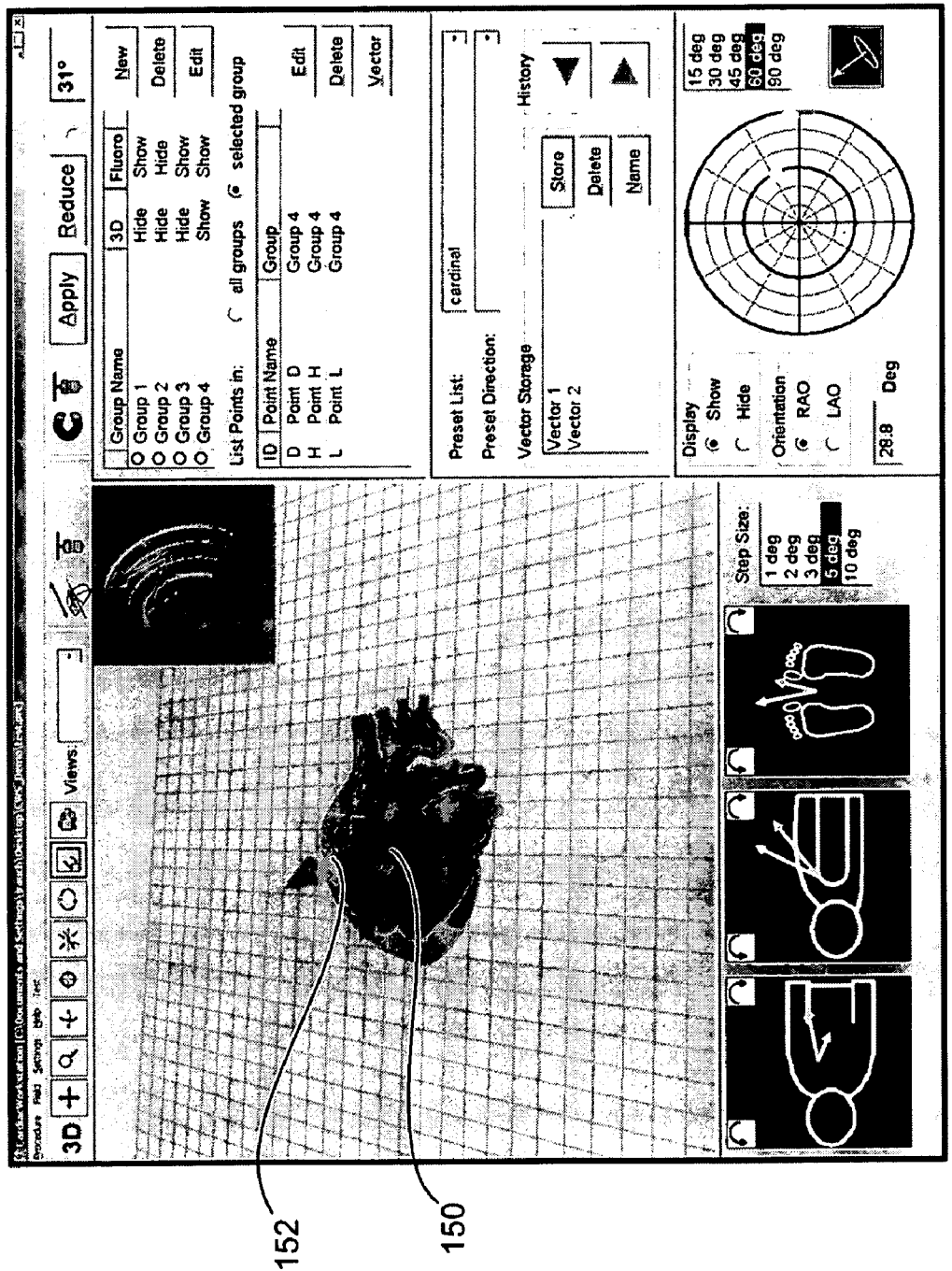
FIG. 4F is a view of the display of the first preferred embodiment of the interface of the invention, showing the bull's eye display in the picture-in-picture portion of the 3-D display pane, and anatomical model in the main 3-D display with the viewpoint changed from FIG. 4E.
Figure 4G:
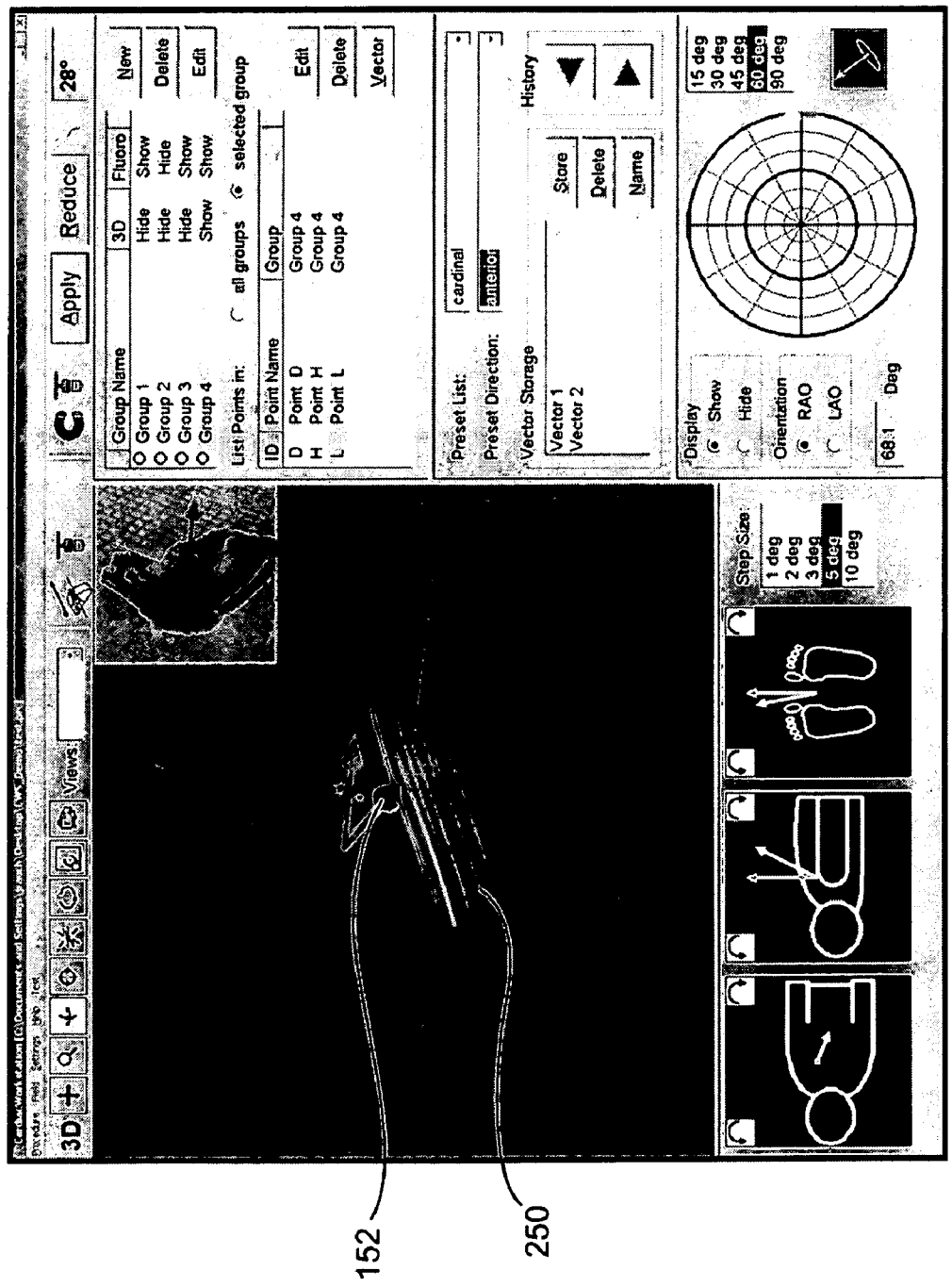
FIG. 4G is a view of the display of the first preferred embodiment of the interface of the invention.
Figure 4H:
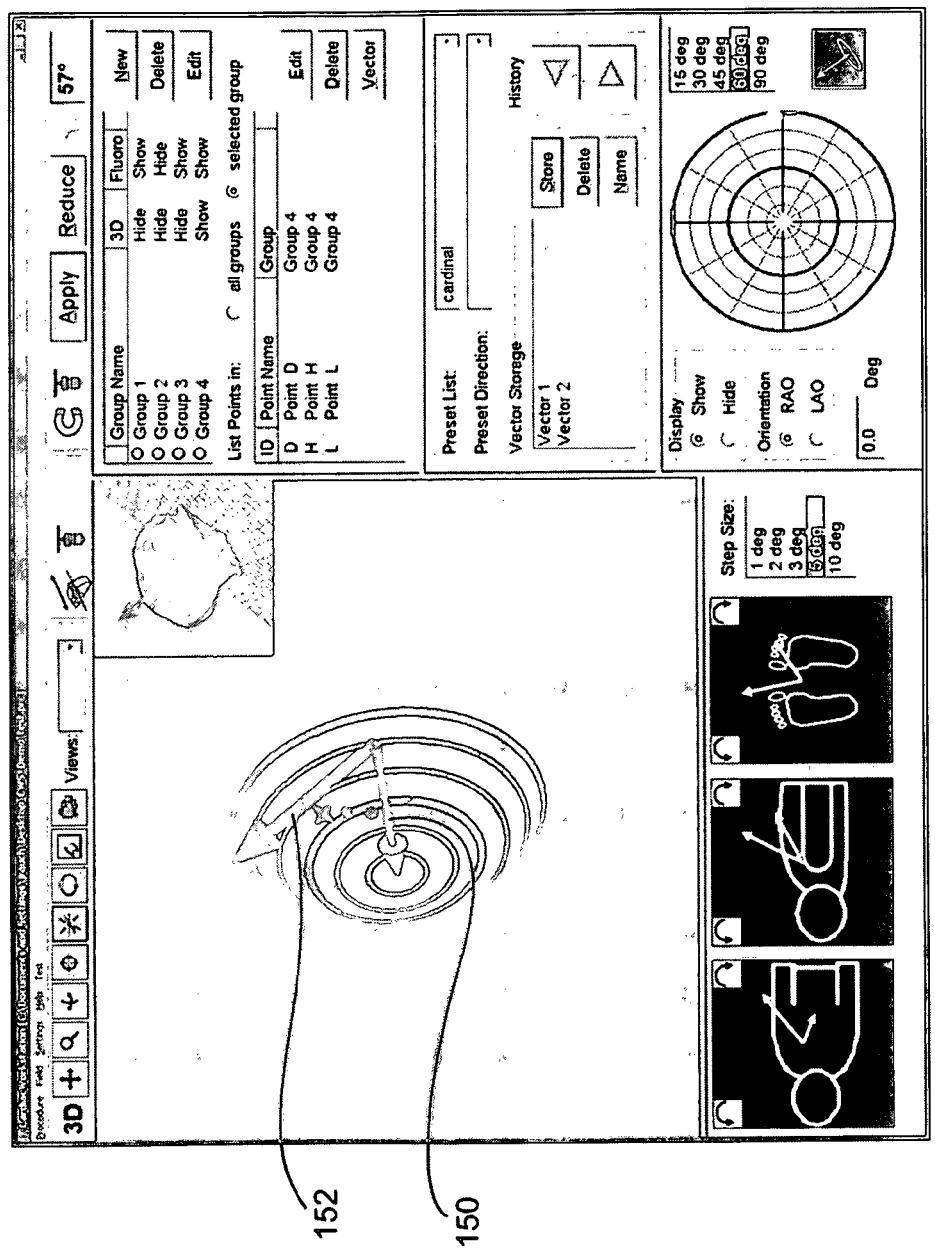
FIG. 4H is a view of the display of the first preferred embodiment of the interface of the invention.
Figure 4I:
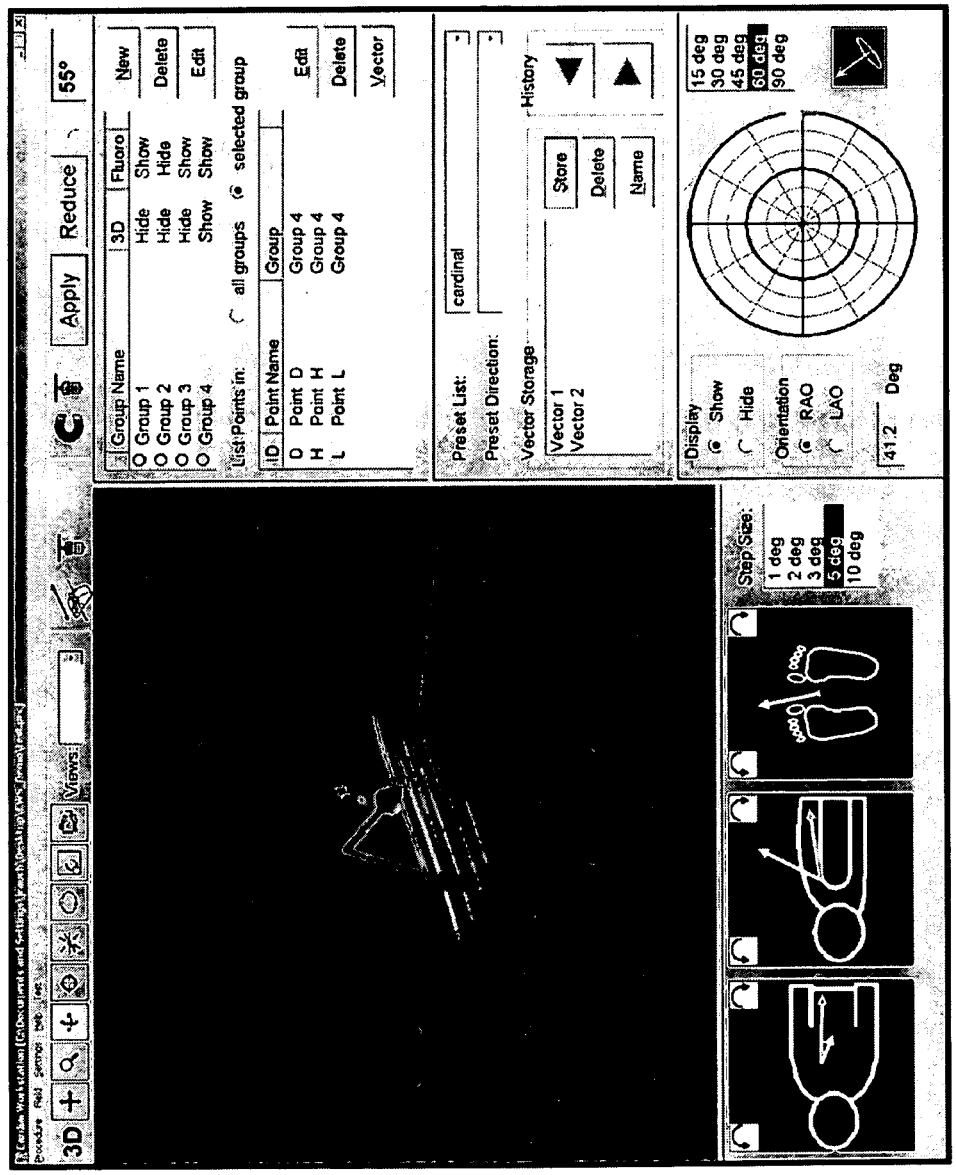
FIG. 4I is a view of the display of the first preferred embodiment of the interface of the invention.
Figure 4J:
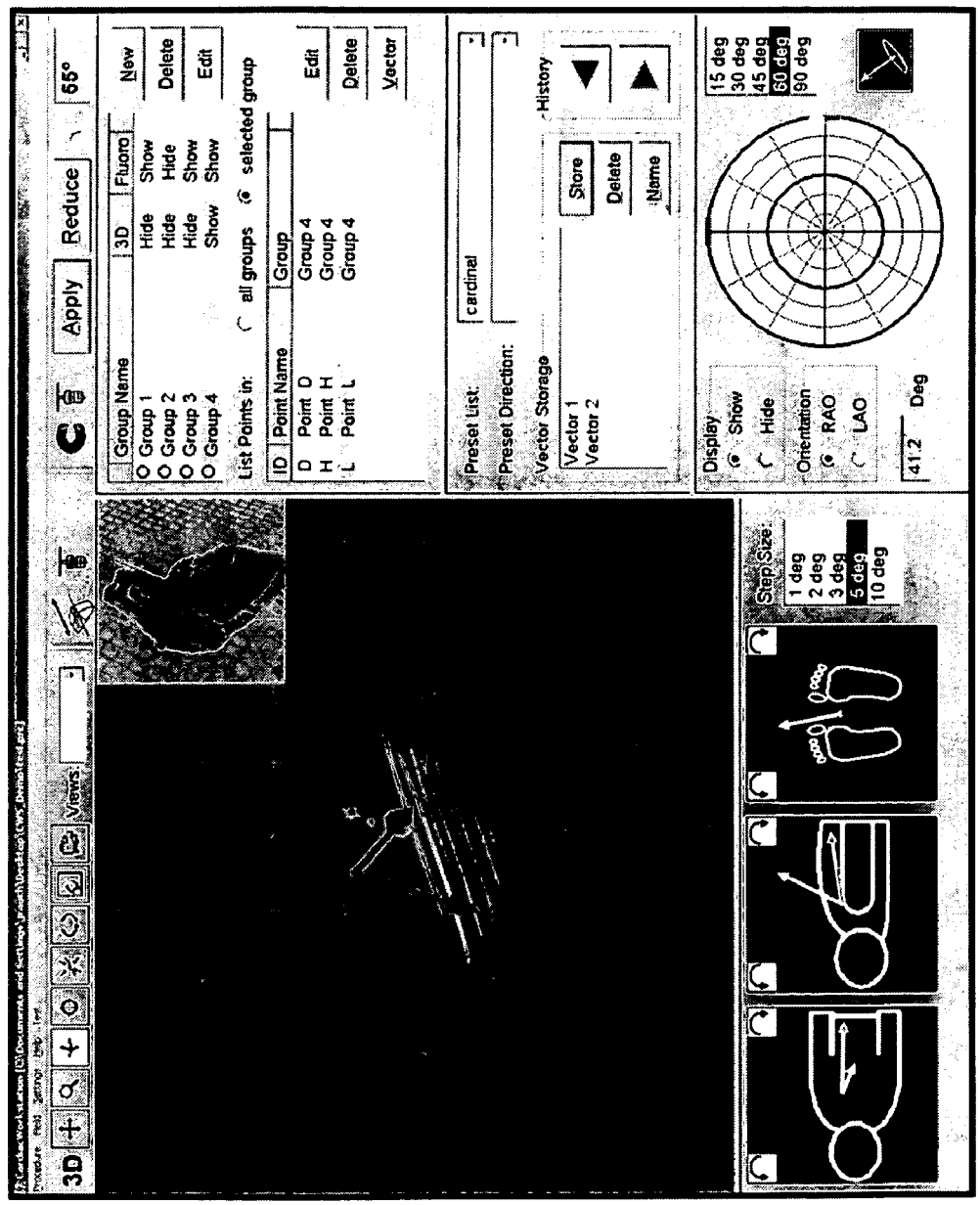
FIG. 4J is a view of the display of the first preferred embodiment of the interface of the invention.

In a first preferred embodiment, as shown in FIG. 3 the display 100 on the monitors 72 and 78, includes a menu bar 102, a tool bar 104, a 3-D display pane 106, a status area 108, a 2-D anatomical control pane 110, a point navigation control pane 112, and a vector navigation control pane 114, and a bull's eye navigation control pane 116. Of course the display 100 could include additional panes or fewer panes or different panes. An example of a display in accordance with this invention is shown in FIG. 4.

Figure 5:
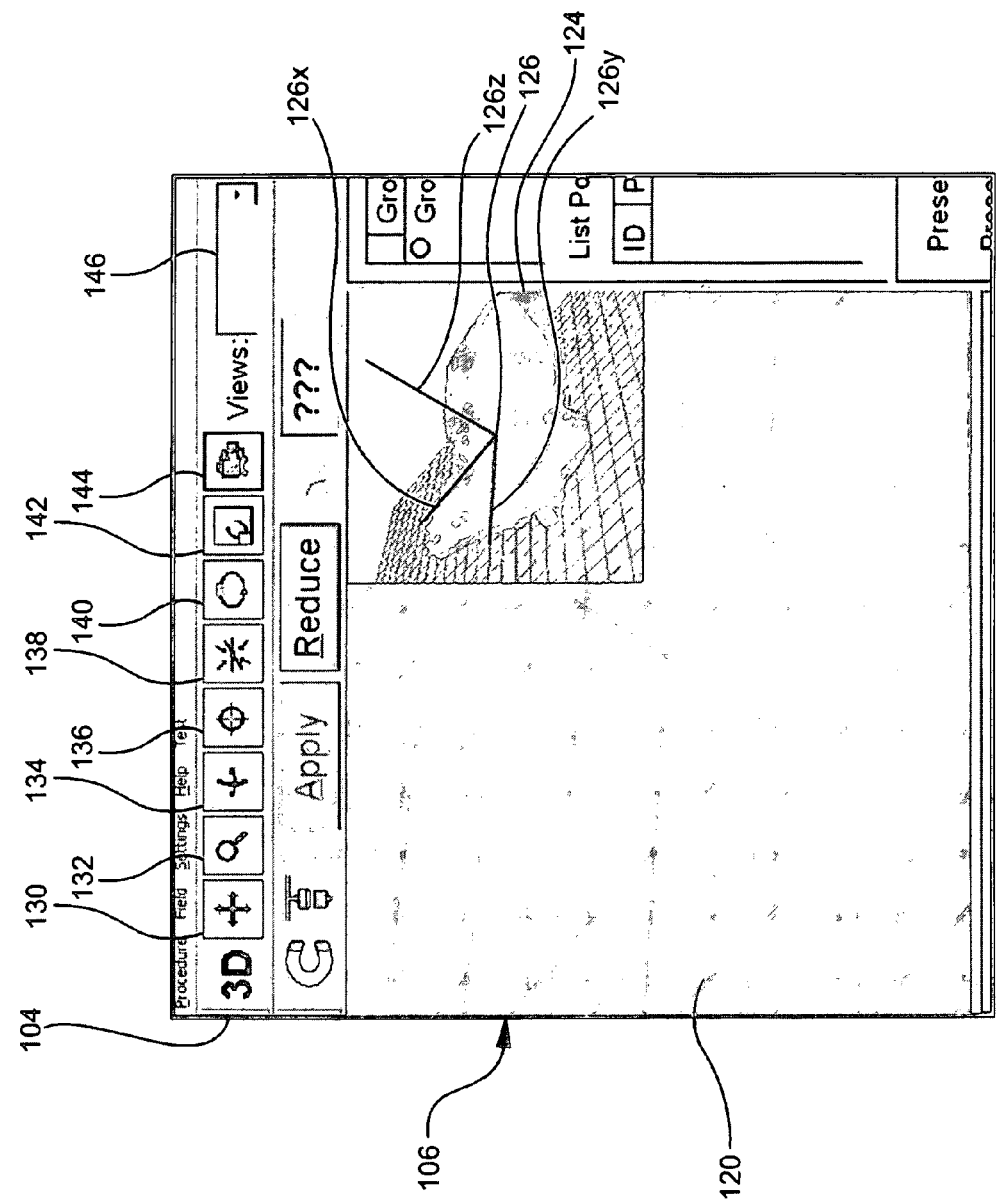
FIG. 5 is an enlarged view of the 3-D display pane of the first preferred embodiment of the interface of this invention.

A 3-D display pane 106 in accordance with this invention is shown in FIG. 5. The display preferably includes a three-dimensional representation 120 of the patient orientation. As shown in FIG. 5 this representation 120 may be a representation of a horizontal grid corresponding to the surface of the patient support 56. Alternatively, the may be a three dimensional representation of an idealized patient, or of the patient support 56. A coordinate system 122 is optionally included in the representation to facilitate the physician's understanding of the orientation. In the first preferred embodiment, the coordinate system 122 comprises a longitudinal axis $122x$, which might for example be colored blue, a horizontal axis $122y$, which might for example be colored red, and a anterior-posterior axis $122z$, which might, for example be colored green. The pane 106 preferably also includes a subpane 124 that displays three dimensional representation of the operating region. In this first preferred embodiment this representation is an transparent, three dimensional idealized representation of the portion of the patient's body in which the procedure is taking place, e.g. a human heart as shown in FIG. 5. To facilitate the user's interpretation of the image, the image may be displayed over a horizontal backing grid. Instead of an idealized representation of the procedure site, the image could be an actual preoperative image, or an actual current image. A coordinate system 126 is optionally included in the representation to facilitate the user's understanding of the orientation. In the first preferred embodiment, the coordinate system 126 comprises a longitudinal axis $126x$, parallel to the direction as axis $122x$, and which may similarly be colored blue, a horizontal axis $126y$, parallel to the direction of axis $122y$, and which may similarly be colored red, and a anterior-posterior axis $126z$, parallel to the direction of axis $122z$, and which may similarly be colored green.

The tool bar 104 includes a 3D tool bar 128 with controls for controlling the 3-D display pane 106. In this first preferred embodiment, these controls include a translation button 130, a magnification button 132, a rotation button 134, a point selection button 136, a point centering button 138, an image autorotate button 140, a swap button 142, and an image capture button 144. These buttons are preferably "virtual buttons", i.e., they are elements on the display which the user can operate by pointing a cursor and clicking.

A view selection menu bar 146 is also provided on the 3D tool bar 128. The view selection menu 146 has an arrow that can be operated to drop down a menu of views to display in the pane 106. These preferably include cranial, caudal, anterior, posterior, left and right, as well as one or more user defined views. Of course other standard views could be provided depending upon the procedures for which the interface is used.

The translation button 130 can be actuated to enter the viewpoint translation mode by pointing the cursor to the button and clicking. In the viewpoint translation mode, the cursor might change in appearance, for example to a shape corresponding to the icon on the button 130. In this mode the view point can be changed by grabbing the image by clicking when the cursor is on the image, and dragging the cursor to move the image and thus the viewpoint in any direction. The cursor can be moved using mouse 74 or 82. This preferably also causes a corresponding translation of the view point of the image in the subpane 124.

The magnification button 132 can be operated to enter the magnification or zoom mode by pointing the cursor to the button and clicking, for example with mouse 74 or 82. In the zoom mode the cursor might change in appearance, for example to a shape corresponding to the magnifying glass icon on the button 132. In this mode the magnification of the patient reference image 120 can be accomplished by grabbing the image by pointing the cursor and clicking, and dragging the cursor downwardly and/or to the right to increase the magnification, or upwardly or to the left to decrease the magnification. Changing the size of the patient reference image preferably also does not change the size of the procedure site reference image.

The rotation button 134 can be operated to enter the image rotation mode by pointing the cursor to the button and clicking, for example with mouse 74 or 82. In the image rotation mode the cursor might change in appearance, for example to a shape corresponding to the shape on the button 134. In this mode the image can be rotated by grabbing the image by pointing the cursor and clicking, and dragging the cursor horizontally to rotate the view point of the image about a generally vertical axis, and vertically to rotate the view point about a generally horizontal axis. Of course the image can be dragged both horizontally and vertically to rotate the axis about a diagonal axis. Rotating the patient reference image preferably also rotates the procedure site reference image, so that these two images always have the same viewpoint.

The point select button 136 can be operated to enter the point selection mode by pointing the cursor to the button and clicking, for example with mouse 74 or 82. In the point selection mode the cursor might change in appearance, for example to a shape corresponding to the shape on the button 136. In this mode a point in the image 120 can be selected by moving the cursor over a point on image and clicking, for example with mouse 74 or 82. The selection of the point causes the point to be identified on the point navigation pane 112, as described in more detail below.

The point center button 138 can be operated to enter the point selection mode by pointing the cursor to the button and clicking, for example with mouse 74 or 82. In the point center mode the cursor might change in appearance, for example to a shape corresponding to the shape on the button 138. In this mode the view point for the image 120 can be centered upon a selected point by moving the cursor over a point on image and clicking, for example with mouse 74 or 82.

The autorotation button 140 can be operated to enter the autorotation mode by pointing the cursor to the button and clicking, for example with mouse 74 or 82. In the autorotation mode the cursor might change in appearance, for example to the shape corresponding to shape on the rotation button. In this mode the viewpoint for the image rotates automatically horizontally to the left. The direction of the rotation can be changed by pointing the cursor on the image and clicking and dragging in the desired new direction of rotation.

The image swap button 142 can be operated to swap the images displayed in the main pane 106 and in the subpane 124 by pointing the cursor to the button and clicking, for example with mouse 74 or 82.

The image capture button 144 can be operated to enter the image capture mode by pointing the cursor to the button, and clicking, for example with mouse 74 or 82. This opens a box that allows the user to save the image on the pane 106 for future reference.

The interface preferably displays a visual indicator of the desired orientation for the distal end of the medical device. In this first preferred embodiment, this indicator is an arrow 150, whose shaft is aligned with the desired orientation, with a large conical head pointing in the desired direction. The arrow 150 is preferably a distinctive color such as green. The interface preferably also displays a visual indicator of the current orientation of the distal end of the medical device. In this first preferred embodiment, this indicator is an arrow 152, whose shaft is aligned with the current orientation of the distal end of the medical device, with a larger conical head pointing in the desired direction.

A localization system could be provided for determining the current position and orientation of the distal end of the medical device. An image representative of the distal end of the medical device can then be generated and displayed in the pane 106. There are numerous method for localizing the distal end of the medical device, for example transmitting magnetic signals between one or more reference locations and the medical device, x-ray image processing, ultrasound localization, or electric potential localization.

In the first preferred embodiment, the interface is adapted for use with a magnetic navigation system that operates by generating a magnetic field of selected direction in the operating region, which causes a magnetically responsive element associated with the distal end of the medical device to generally align with the applied field. Because of the physical properties of the catheter, limitations in the strength of the applied field, and the conditions in the procedure site, the distal end of the medical device may not align precisely with the applied magnetic field. While the difference between the applied magnetic field and the actual direction of the distal end of the medical device can be accounted for through modeling or a look-up table, in the first preferred embodiment the arrow 150 representing the desired orientation may represent the desired direction of the applied magnetic field, rather than the desired direction of the medical device itself. Similarly, the arrow 152 representing the current orientation may represent the direction of the magnetic field to currently being applied, rather than the actual direction of the device itself. However, the differences between the actual direction of the medical device and the applied magnetic field can be characterized by equation or an empirically determined look-up table, or localization of the device can be provided so that even when used with a magnetic navigation system, the arrow 150 represents the actual desired orientation of the medical device, and arrow 152 represents the actual current direction.

To help visualize the three-dimensional direction of the indicator, the arrow 150 can be surrounded with an "umbrella" 154—a shape or surface surrounding the arrow so that its direction and orientation can be more easily visualized. One implementation of the umbrella 154 is as a wire frame hemisphere. In addition to improving the visualization of the direction of the arrow 150, the umbrella 154 can be used to selection the orientation of the arrow 150. When the cursor hovers over the surface of the umbrella, the cursor can change appearance, for example to resemble the rotation icon on button 134. The direction of the arrow 150 can be changed by rotating the hemisphere by pointing the cursor to the hemisphere, clicking, and dragging the cursor in the desired direction of rotation. In addition the arrow 150 and hemisphere 154 can be configured so that when the cursor hovers over the root of the arrow 150, the cursor can change in appearance, for example to resemble the translation icon on button 130. The position of the root of the arrow 150 can be changed by clicking the cursor and dragging the cursor in the desired direction of movement.

Figure 6A:
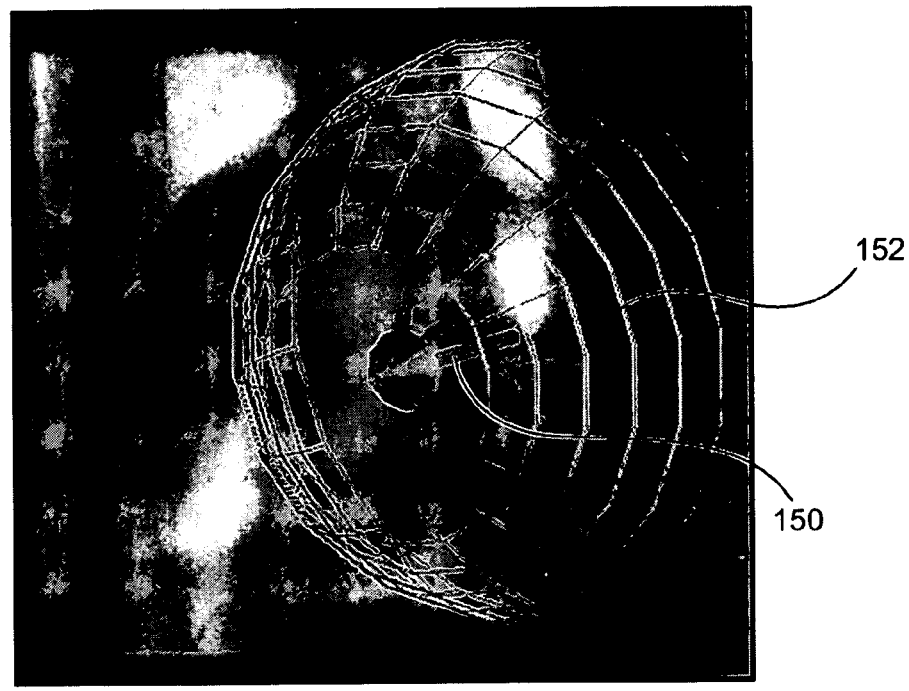
FIG. 6A and FIG. 6B are left anterior oblique (LAO) and right anterior oblique (RAO) images of the procedure site with desired orientation arrow and visualization surface superposed thereon.
Figure 6B:

In the first preferred embodiment, the interface includes displays of the fluoroscopic images of the operating region, with the arrow 150 superposed thereon. For example, as shown in FIGS. 6A and 6B, the imaging system 68 can provide biplanar images of the operating region, and the arrow 150 and umbrella 154 provided on each image. These images could be displayed on monitors 86 and 88 in the procedure room 50, and on monitor 90 in the control room 52. Preferably, the user can change the direction of the arrow 150 on these images as well by rotating and translating the arrow and umbrella as described above.

Figures 6C, 7:
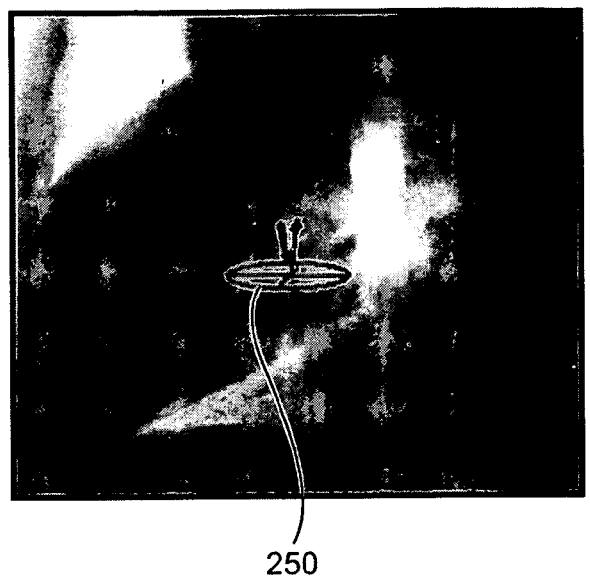
FIG. 6C is an alternate implementation of the visualization surface superposed thereon.
FIG. 7 is an enlarged view of the status pane of the first preferred embodiment of the interface of this invention.

The display 100 of the interface preferably also includes a status area 108, where, as shown in FIG. 7, a text, graphic, or combination text and graphic message of the status of the interface can be displayed to the user. These messages can be colored coded for example to convey an immediate impression of the importance or significance of the message displayed.

While the orientation of the distal end of the medical device can be manipulated directly on the pane 106, for example by manipulating the umbrella 154, the display 100 of the interface preferably includes at least one pane to aid the user in selecting the desired orientation for the medical device. In this first preferred embodiment there are several panes that provide alternative methods for the user to select the desired orientation for the distal end of the medical device. These panes include representations of the orientation of the arrow 150 which are constantly updated, so that use of one pane to change the desired direction of the medical device, causes all of the other panes to update, to facilitate the use of any of the panes to adjust the orientation of the arrow 150 representing the desired new orientation of the medical device.

Figure 8A:
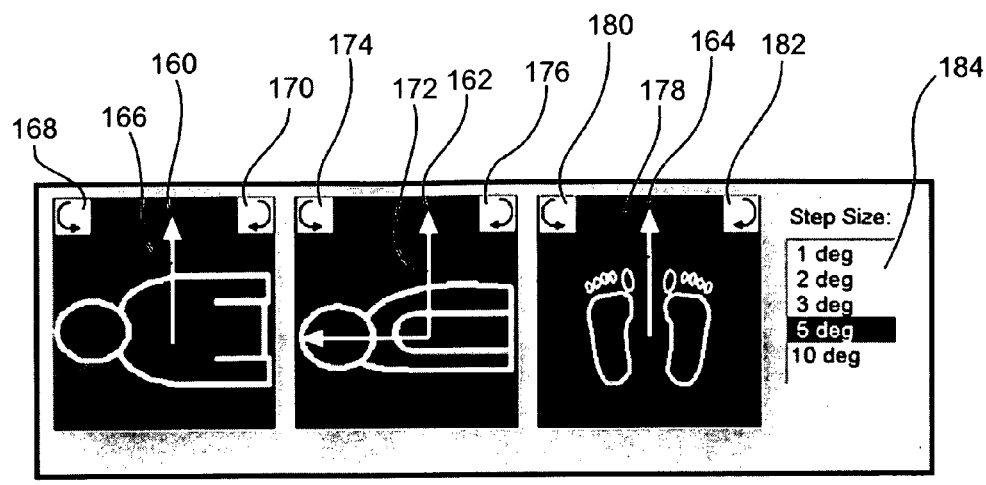
FIG. 8A is an enlarged view of the 2-D navigation pane of the first preferred embodiment of the interface of this invention.

One such pane to aid the user in selecting the desired orientation for the medical device is the 2-D anatomical pane 110, which allows the user to select the desired orientation of distal end of the medical device as indicated by the arrow 150 by adjusting the direction in one or more planes through the patient. As shown in FIG. 8A, the pane 110 allows the user to change the direction of the arrow 150 in at least one plane, and preferably at least two planes and more preferably at least the planes. These planes are preferably, but not necessarily, mutually perpendicular. While adjustment in two planes is sufficient to specify any direction, providing adjustment in three planes makes it easier for a user to select the desired direction for the arrow 150. In this first preferred embodiment, the arrow can be rotated in the coronal or frontal plane (i.e., about an anterior-posterior axis), the median or saggital plane (i.e., about a horizontal axis), and the horizontal or transverse plane (i.e., about a longitudinal axis).

As shown in FIG. 8A the pane 110 can have three graphic displays 160, 162 and 164, corresponding to the three planes of rotation. Graphic display 160 contains a graphic depiction of the coronal or frontal plane (i.e., an caricature image of a patient's body in the coronal or frontal plane), with an indicator 166 that indicates the orientation of the arrow in the coronal or frontal plane, and virtual buttons 168 and 170 for moving the indicator 166 (and thus the arrow 150) clockwise or counterclockwise in the coronal or frontal plane abut the anterior-posterior axis. In this first preferred embodiment, indicator 166 is actually a projection of the arrow 150 in the plane, and thus the length of the indicator 166 is indicative of the orientation. The virtual buttons 168 and 170 can be operated with a cursor for example with the mouse 74 or 82 or the keyboard 80, to point and click the button and move the indicator 166 and thus the arrow 150, in the desired direction. Display 162 contains a graphic depiction of the median or saggital plane (i.e., a caricature image of a patient's body in the median or saggital plane), with an indicator 172 indicating the direction of the arrow 150 in the median or saggital plane, and virtual buttons 174 and 176 for moving the indicator 172 (and thus the arrow 150) clockwise or counterclockwise in the coronal or frontal plane. In this first preferred embodiment, indicator 172 is actually a projection of the arrow 150 in the plane, and thus the length of the indicator 172 is indicative of the orientation. The virtual buttons 174 and 176 can be operated with a cursor for example with the mouse 74 or 82 or the keyboard 80, to point and click and move the indicator 172 and thus the arrow 150, in the desired direction. Display 164 contains a graphic depiction of the horizontal or transverse plane (i.e., a caricature image of a patient's body in the horizontal or transverse plane), with an indicator 178 indicating the direction of the arrow in the horizontal or transverse plane, and virtual buttons 180 and 182 for moving the indicator 178 (and thus the arrow 150) clockwise or counterclockwise in the horizontal or transverse plane. The virtual buttons 180 and 182 can be operated with a cursor for example with the mouse 58 or 66 or the keyboard 64, to point and click to move the indicator 178, and thus the arrow 150 in the desired direction.

The pane 110 also includes a menu 184 to select the increment of change in direction upon operating the buttons 168 and 170, 174 and 176, and 180 and 182. The user can select the incremental change from 1 degree, 2 degrees, 3 degrees, 5 degrees, 10 degrees with a cursor for example with the mouse 74 or 82 or the keyboard 80, to point and click to select the desired increment.

Figure 8B:
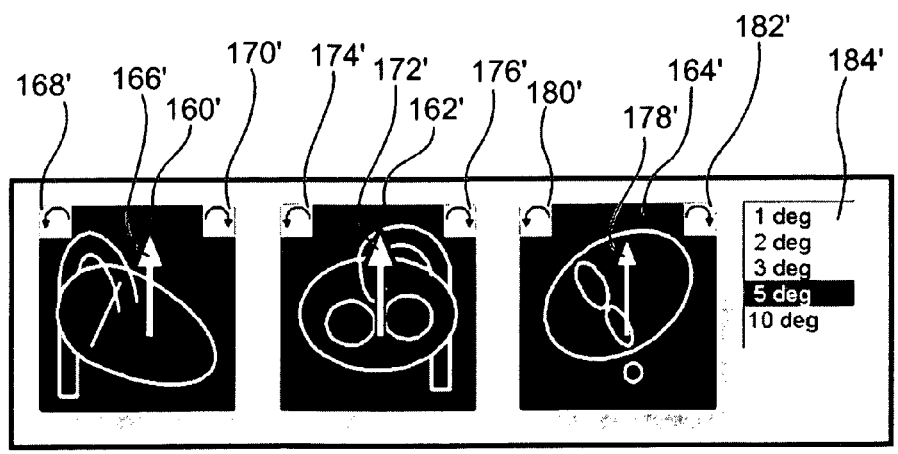
FIG. 8B is an enlarged view of an alternate embodiment of the 2-D navigation pane of FIG. 8A.

An alternate implementation of the pane 110' is shown FIG. 8B. In contrast to FIG. 8A where pane 110 allows movement of the arrow 150 relative to the coronal or frontal plane, the median or saggital plane, and the horizontal or transverse plane, in FIG. 8B the pane 110' allows movement of the arrow 150 relative to the right anterior oblique plane, the left anterior oblique plane, and the transverse plane. As shown in FIG. 8B the pane 110 can have three graphic displays 160', 162' and 164', corresponding to the three planes of rotation. Graphic display 160' contains a graphic depiction of the right anterior oblique plane (i.e., an caricature image of patient's body or part of the patient's body in the RAO plane), with an indicator 166' that indicates the orientation of the arrow in the coronal or frontal plane, and virtual buttons 168' and 170' for moving the indicator 166' (and thus the arrow 150) clockwise or counterclockwise in the left anterior oblique plane. In this first preferred embodiment, indicator 166' is actually a projection of the arrow 150 in the plane, and thus the length of the indicator 166' is indicative of the orientation. The virtual buttons 168' and 170' can be operated with a cursor for example with the mouse 74 or 82 or the keyboard 80, to point and click the button and move the indicator 166' and thus the arrow 150, in the desired direction. Display 172' contains a graphic depiction of the left anterior oblique plane (i.e., a caricature image of a patient's body or portion of the patient's body in the LAO plane), with an indicator 172' indicating the direction of the arrow 150 in the median or saggital plane, and virtual buttons 174' and 176' for moving the indicator 172' (and thus the arrow 150) clockwise or counterclockwise in the coronal or frontal plane. In this first preferred embodiment, indicator 172' is actually a projection of the arrow 150 in the plane, and thus the length of the indicator 172' is indicative of the orientation. The virtual buttons 174' and 176' can be operated with a cursor for example with the mouse 74 or 82 or the keyboard 80, to point and click and move the indicator 172' and thus the arrow 150, in the desired direction. Display 164' contains a graphic depiction of the horizontal or transverse plane (i.e., a caricature image of a patient's body or a portion of the patient's body in the horizontal or transverse plane), with an indicator 178' indicating the direction of the arrow in the horizontal or transverse plane, and virtual buttons 180' and 182' for moving the indicator 178' (and thus the arrow 150) clockwise or counterclockwise in the horizontal or transverse plane. The virtual buttons 180' and 182' can be operated with a cursor for example with the mouse 58 or 66 or the keyboard 64, to point and click to move the indicator 178', and thus the arrow 150 in the desired direction.

The pane 110' also includes a menu 184' to select the increment of change in direction upon operating the buttons 168' and 170', 174' and 176', and 180' and 182'. The user can select the incremental change from 1 degree, 2 degrees, 3 degrees, 5 degrees, 10 degrees with a cursor for example with the mouse 74 or 82 or the keyboard 80, to point and click to select the desired increment.

Figure 9:
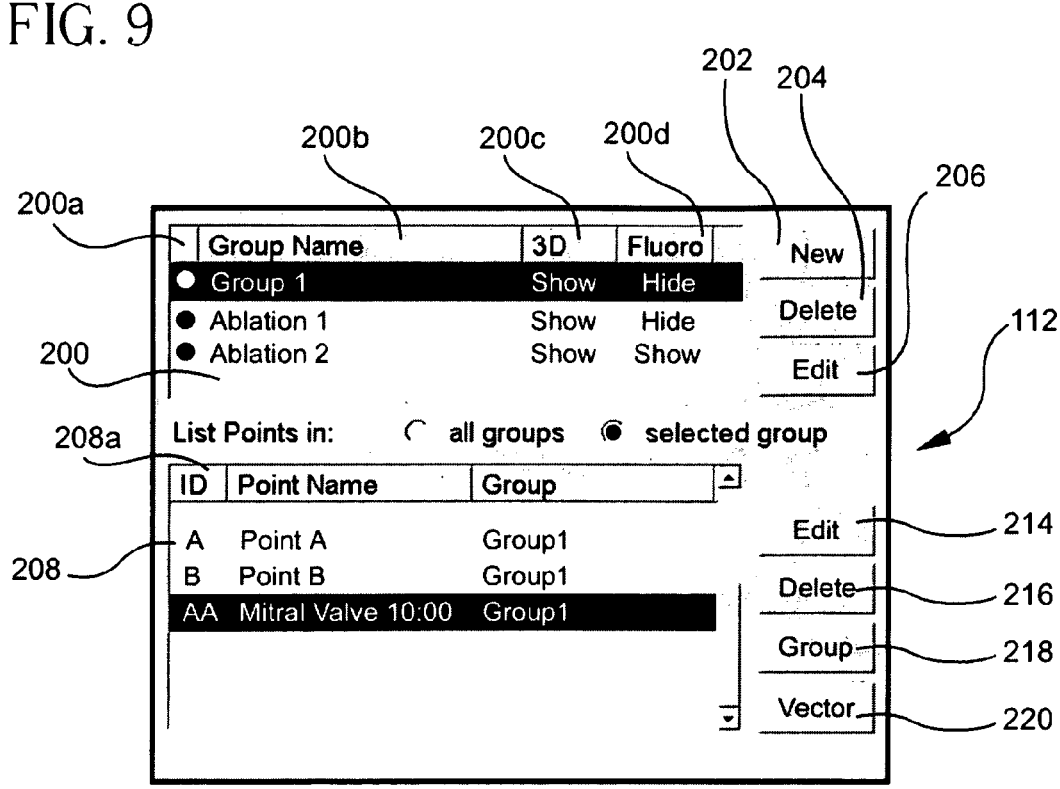
FIG. 9 is an enlarged view of the point navigation pane of the first preferred embodiment of the interface of this invention.
Figure 10:
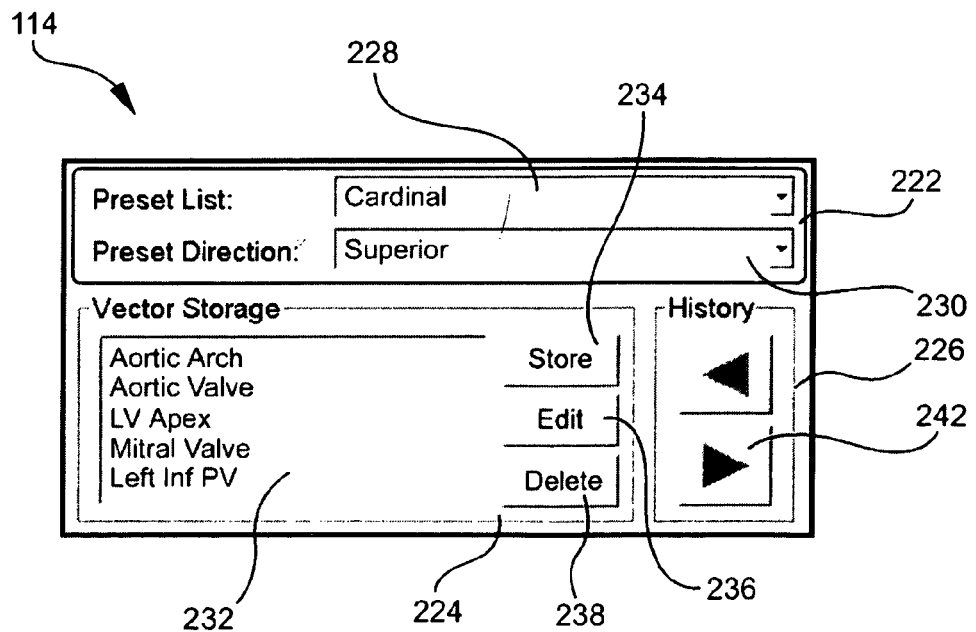
FIG. 10 is an enlarged view of the vector navigation pane of the first preferred embodiment of the interface of this invention.

Another pane to aid the user in selecting the desired orientation for the arrow 150 and thus for the medical device is a point navigation pane 112. As shown in FIG. 9, the point navigation pane 112 includes a group menu table 200 containing information about one or more groups of points the user identifies. The group menu table 200 includes a column 200a with a color indicator for indicating the color corresponding to the points in the group. All points in the group will be indicated with a mark in the indicated color. The menu table 200 further includes a column 200b entitled "Group Name" with the name of a stored group of points. The menu table 200 further includes a column 200c entitled "3D" which indicates whether the group of points is visible on the 3D display in pane 106 ("show") or not visible on the 3D display in the pane ("hide"). Finally, the table comprises a column 200 entitled "Fluro" which indicates whether the group of points is visible on the 3D display in pane 106 ("show") or not visible on the 3D display in the pane ("hide").

A "new" button 202, a "delete" button 204, and an "edit" button 206 are associated with the menu table 200. The buttons 202, 204, and 206 are preferably "virtual" buttons, i.e. portions of the display on which the user points the cursor and clicks, for example with mouse 74 or 82, or keyboard 82. The new button 202 can be operated by pointing and clicking with the cursor using the mouse 74 or 82 or keyboard 80, and allows the user to create a new group in the menu table 200. Operating the new button 202 opens a box that allows the user to select the color indicator in column 200a, select the name of the group in column 200b, select the display properties in column 200c between "show" and "hide" to determine whether the points will appear on the 3D panel 110, and select the display properties in column 200d, between "show" and "hide" to determine whether the points will appear on the fluoroscope displays (monitors 86, 88, and 90). The delete button 204 can be operated by pointing and clicking with the cursor using the 74 or 82, or keyboard 82, and allows the user to delete the group or groups that the user highlighted in the menu table 114, using the mouse 74 or 82, or keyboard 82. The edit button 206 can be operated by pointing and clicking with the cursor using the mouse 74 or 82, or keyboard 82, and allows the user to edit the group that the user highlighted in the menu table 200 using the 74 or 82, or keyboard 82. Operating the edit button 206 opens a box that allows the user to change the color indicator in column 200a, change the name of the group in column 200b, change the display properties in column 200c between "show" and "hide" to determine whether the points will appear on the 3D panel 110, and change the display properties in column 200d, between "show" and "hide" to determine whether the points will appear on the fluoroscope displays (monitors 86, 88, and 90).

The pane 112 also includes a point menu table 208. The menu table 208 includes a column 208a, entitled "id" for an identification code assigned by the system to a particular point (in the first preferred embodiment the system assigns an id from A to ZZ). The menu table 208 further includes a column 208b, entitled "point name" for the name of the point. Finally, the menu table 208 includes a third column 208c entitled "group" for the name of the group to which the point is assigned. A display control is provided adjacent the point menu table 208 for selection the points to display in the point menu table 208. As shown in FIG. 9, the display control can comprise radio buttons 210 and 212, which allow the user to specify "all groups" or "selected group", respectively, so that the user can identify whether to display the points in "all groups" or just the points a selected group "selected group" in the menu table 208.

An "edit" button 214, a "delete" button 216, a "group" button 218, and a "vector" button 220 are associated with the menu table 208. The buttons 214, 216, 218, and 220 are preferably "virtual" buttons on the display that can be operated by pointing the cursor and clicking, for example with mouse 74 or 82, or keyboard 80. The user can select a point on the menu table 200 by pointing with the cursor and clicking, using the muse 74 or 82, or the keyboard 80. The edit button 214 can be operated by pointing and clicking with the cursor using the mouse 74 or 82 or keyboard 80, and allows the user to edit the selected point. Operating the edit box opens a box that allows the user to change the name of the selected point in column 208b, and the group to which the point is column 208c. The delete button 216 can be operated by pointing and clicking with the cursor using the mouse 74 or 82 or keyboard 80, and allows the user to delete the selected point. The group button 218 can be operated by pointing and clicking with the cursor using the mouse 74 or 82 or keyboard 80, and allows the user to change the group to which the selected point is associated. The vector button 220 can be operated by pointing and clicking with the cursor using the mouse 74 or 82 or keyboard 80, and allows the user to set the orientation of the arrow 150 to the orientation associated with a point selected on the menu table 208 using the mouse 74 or 82 or keyboard 80. This automatically updates the display of arrow 150 in the other panes. Thus a user who wants to navigate back to a stored point can recall the direction associated with that point, facilitating the return to the point. However that direction may also be useful in navigating to another point.

Another such pane to aid the user in selecting the desired orientation for the medical device is a vector navigation pane 114. The vector navigation pane 114 allows the user to use predetermined directions, to store and use new directions, and to recall and use previously used directions. The vector navigation pane 114 includes a section 222 for recalling and using predetermined directions; a direction vector storage and recall section 224; and a direction history and recall section 226. The section 222 for recalling and using predetermined directions includes a "preset list" pick menu 228 for selecting a particular set of predetermined directions, and a "direction" pick menu 230 for selecting a particular direction from the selected set. A set of possible "preset list" and "direction" entries for the pick menus 228 and 230 is shown in Table 1. The user can select from the "preset list" and "direction" pick menus using the mouse 74 or 82 or keyboard 80.

TABLE 1

| Possible Preset Lists and Directions | |
|---|---|
| Cardinal | Superior |
| Cardinal | Inferior |
| Cardinal | Anterior |
| Cardinal | Posterior |
| Cardinal | Left |
| Cardinal | Right |
| Cardinal | RAO |
| Cardinal | LAO |
| Deflection | From 0 to 175° in 15° increments |

The direction vector storage and recall section 224 includes a vector menu table 232, and associated "store" button 234, "edit" button 236, "delete" button 238. The buttons 234, 236, and 238 are preferably virtual buttons, or portions of the display to which the cursor can be pointed and clicked, for example with the mouse 74 or 82, or the keyboard 80. The "store" button 234 can be operated by pointing and clicking with the cursor using the mouse 74 or 82 or keyboard 80, and allows the user to store the current direction under a user selected name on the vector menu table 232. Operating the store button 234 opens a box that allows the user to input a name. The user can selected a stored direction from the menu table 232 by pointing to the name with the cursor, and clicking, using the mouse 74 or 82, or keyboard 80. The "edit" button 236 can be operated by pointing and clicking with the cursor using the mouse 74 or 82 or keyboard 80, and allows the user to edit the name of a selected direction. The "delete" button 238 can be operated by pointing and clicking with the cursor using the mouse 74 or 82 or keyboard 80, and allows the user to delete a selected direction. The history section 226 includes virtual forward and back buttons 240 and 242. The forward and back buttons 240 and 242 can be operated by pointing the cursor and clicking using mouse 74 or 82 or keyboard 80. The buttons 240 and 242 allow the user to set the orientation of the arrow 150 to one of the previously selected directions, which are automatically stored. In the first preferred embodiment, the system automatically stores the last ten directions, and the user can scroll backward and forward through these directions with the buttons 240 and 242. The appearance of the buttons 240 and 242 changes (e.g. grays out) when the there is no further stored directions.

Figure 11:
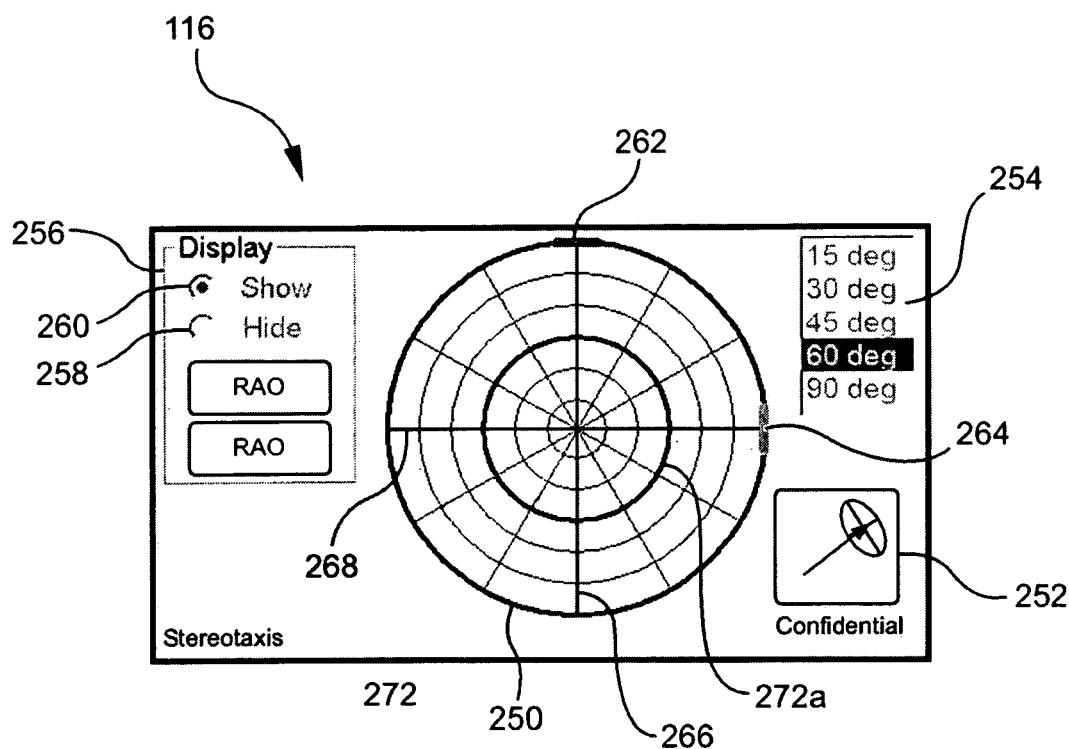
FIG. 11 is an enlarged view of the bull's eye navigation pane of the first preferred embodiment of the interface of this invention.
Figure 12:
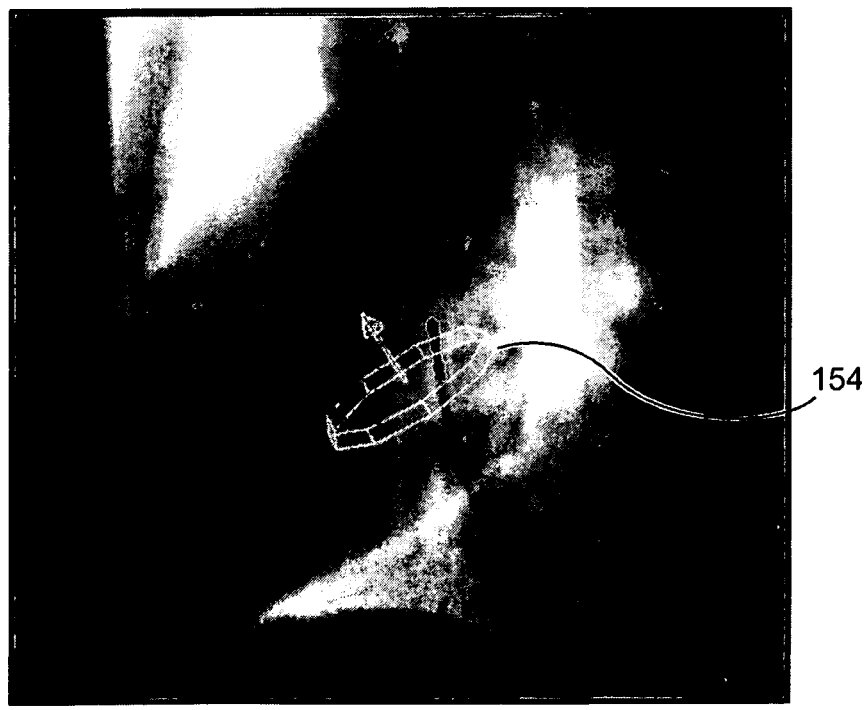
FIG. 12 is a view of an x-ray image showing the projection of the bull's eye screen thereon.
Figure 13:
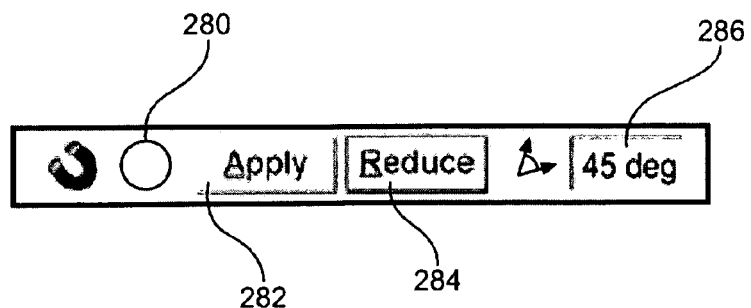
FIG. 13 is an enlarged view of the menu bar of the first preferred embodiment of the interface of this invention.

The bull's eye navigation pane 116 includes a circular screen 250, and an "apply" button 252. The pane 116 also includes a scale menu 254, which in the first preferred embodiment allows the user to select the scale of the screen 250 from 15, 20, 45, 60, and 90 degrees. The user can select the desired scale for the circular screen 250 by pointing the cursor and clicking, using the mouse 74 or 82 or keyboard 80. The pane 116 may also include a display control section 256 with "Hide" and "Show" radio buttons 258 and 260. These buttons determine whether the circular screen 250 is projected onto the other displays, specifically the 3D display of pane 106 and the fluoroscopic images from the imaging system displayed on the monitors 86, 88, and 90. FIG. 12 shows one of the biplane imaging displays with the screen 250 projected thereon. The display control section 256 also includes RAO (right anterior oblique) and LAO (left anterior oblique) selection buttons 262 and 264, which orient the screen 250 so that the top of the screen is up in whichever of the two views is selected. As shown in FIG. 11, markers 262 and 264 are provided on the circular screen 250, to help the user interpret the orientation of the circular screen 250 on the 3D pane 106 and the on the RAO and LAO views. The marker 262 might be blue and the marker 264 might be red.

The user can set the base direction the navigation pane 116 by operating the "apply" button 252 by pointing at the button with a cursor and clicking, using mouse 74 or 82 or keyboard 80. The sets the current direction as the direction though the center of the screen 250. The user can then specify a direction for the arrow 150 by selecting a point on the screen 250, by pointing with the cursor and clicking, using mouse 74 or 82, or keyboard 80. As shown in FIG. 11, the screen 250 has vertical and horizontal cross hairs 266 and 268, and a plurality of radially extending markers 270, at 30 degree intervals. There are a plurality of concentric circular markers 272 representing regular angular intervals (10 degree intervals in the first preferred embodiment), with specified intervals (30 degree intervals in the first preferred embodiment) indicated by bold markers 272a. The circular screen 272 actually represents a hemisphere of space. The screen allows the user to orient the arrow 150 at a number of points to draw radial and circular lines.

The toolbar 104 preferably also includes an indicator 280, an apply button 282, a reduce button 284, and an angle indicator 286. The indicator 280 indicates when the interface is connected to the magnetic navigation system. Of course if some other system for orienting the distal end of the medical device is used, a suitable indicator can be provided. The apply button 282 and the reduce button 284 are preferably virtual buttons which are operated by pointing the cursor and clicking, for example with mouse 74 or 82, or keyboard 80. Operating the apply button 282 causes the magnetic navigation system to apply a magnetic field to orient the distal end of the medical device in the orientation of the arrow 150. Operating the reduce button 284 causes the magnetic navigation system to "turn off" the magnetic field. The indicator 286 indicates the angular difference between the previously applied magnetic field and the orientation of arrow 150. Of course rather than discrete navigation, in which the arrow 150 is successively oriented and the magnetic field applied, the interface could be adapted to operate in a continuous navigation mode in which the field is automatically applied in the direction of arrow 150.

Operation

In operation the user can visualize the current direction of the device represented by arrow 154 and the desired new direction for the device represented by arrow 150, on the 3-D pane 106 or on the x-ray images on monitors 86, 88, and 90. The user can selected the orientation of the arrow 150 in a number of ways using panes 110, or 112, or 114, or 116.

The user can select the orientation of arrow 150 on pane 110 by clicking on buttons 168 and 170, 174 and 176, and 180 and 182, to move the arrow 150 in each of the coronal or frontal plane, the median or saggital plane, and the horizontal or transverse plane to move the arrow. Alternatively, the user can select the orientation of arrow 150 by using the pane 112. The user selects a point on the menu table 208 by pointing and clicking with the cursor, and then operating the vector button 220 by pointing and clicking with the cursor. This sets the orientation of arrow 150 to the orientation associated with point selected. Alternatively, the user can select the orientation of arrow 150 using the pane 114. The user can select a stored orientation by selecting a category on menu 228, and a direction on menu 230. The user can select a user-stored direction by selecting a direction vector from the menu table 232. The user can select a previously used direction by using the buttons 240 and 242 to recall one of the last previously used direction. Finally, the user can select an orientation by picking a point on a screen 250.

Once the direction of the arrow 150 is selected, the navigation system can be operated by operating the apply button 282. This can operate a magnetic navigation system to apply a field in the direction 150, or it can operate a magnetic navigation system to apply a field to cause the medical device to align in the direction 150, either by using feedback of the catheter position or by calculating or using a look-up table to account for the properties of medical device.

Figure 14:
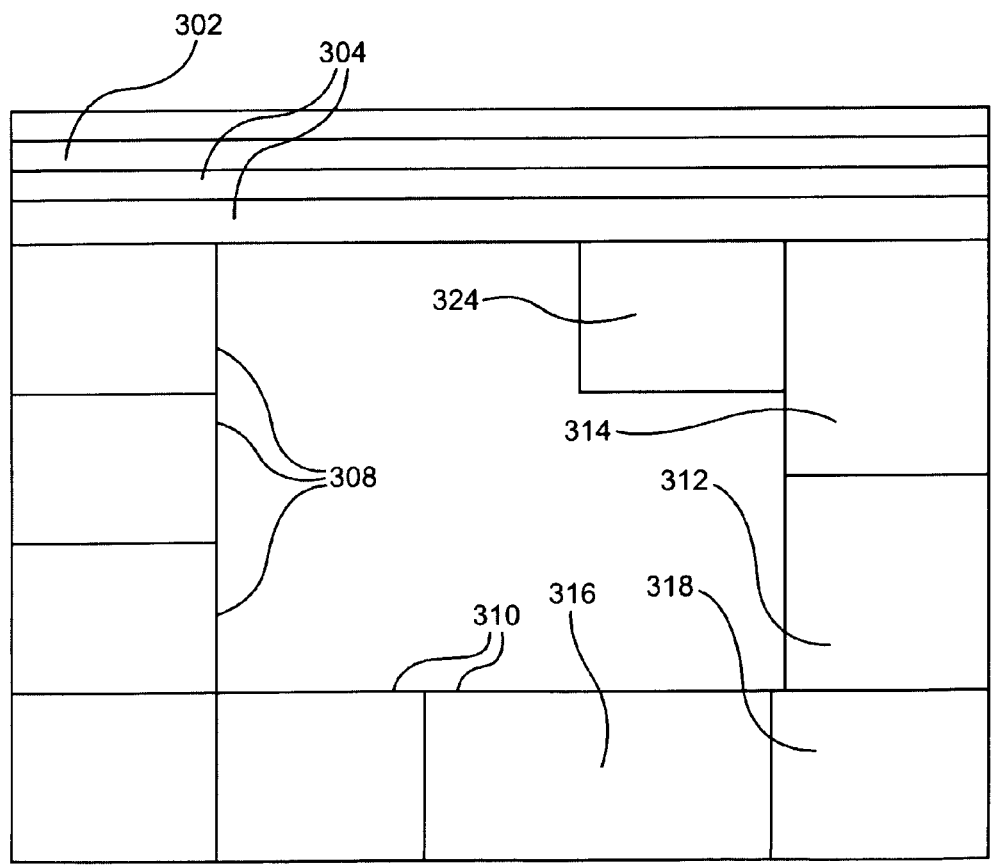
FIG. 14 is a schematic diagram of the display of a second preferred embodiment of the interface of this invention.

In second preferred embodiment, as shown in FIG. 14 the display 100' on the monitors 72 and 78, includes a menu bar 302, tool bars 304, a 3-D display pane 306, a 2-D anatomical control pane 308, a point navigation control pane 310, a vector navigation control pane 312, and a bull's eye navigation control pane 314, an advancer control pane 316, and a title block and device selection pane 318. Of course the display 100' could include additional panes or fewer panes or different panes. An example of a display in accordance with this invention is shown in FIG. 15.

Figure 15:
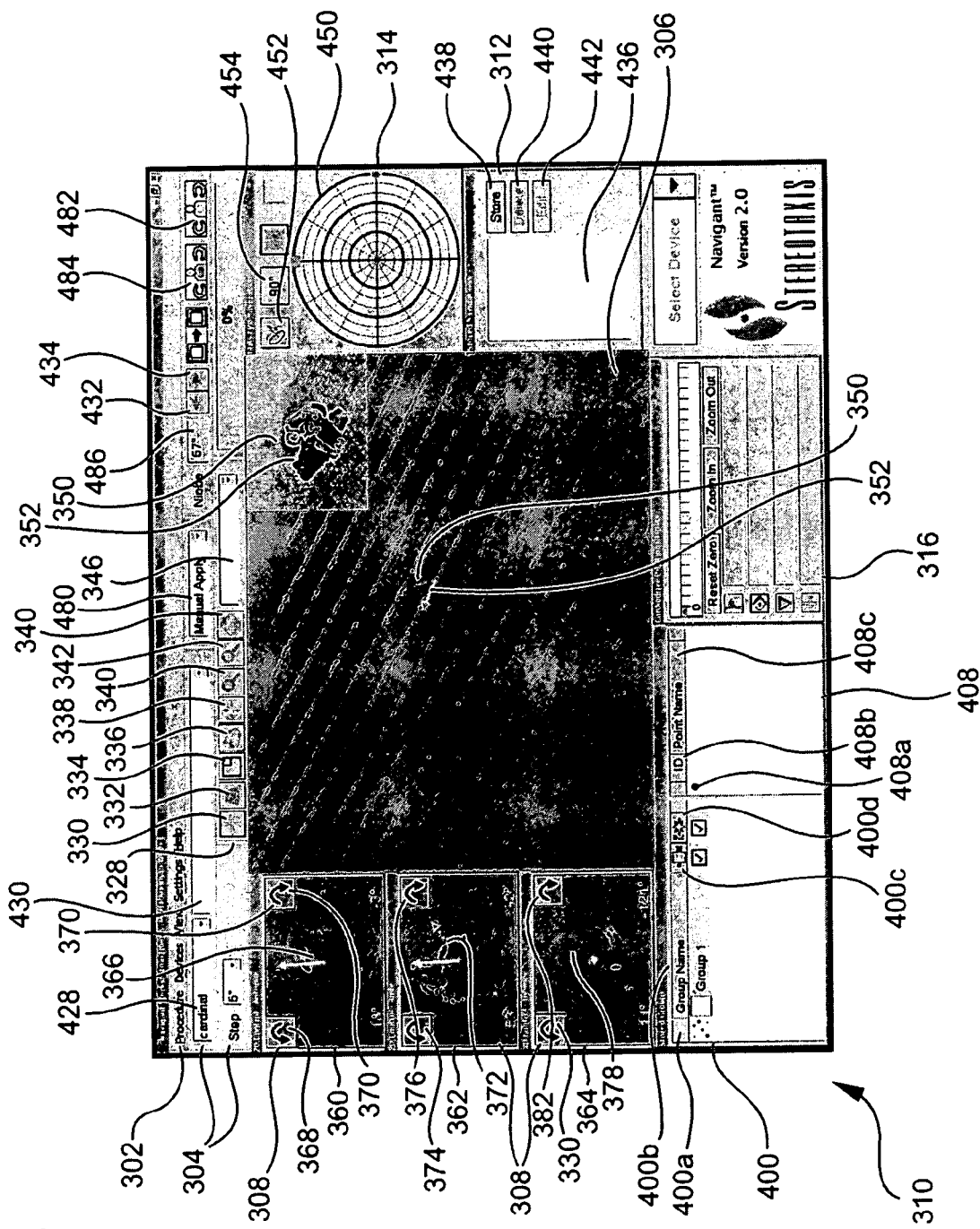
FIG. 15 is a view of the display of the second preferred embodiment of the interface of this invention.

A 3-D display pane 306 in accordance with this invention is shown in FIG. 15. The display preferably includes a three-dimensional representation of the patient orientation. As shown in FIG. 15 this representation may be a representation of a horizontal grid corresponding to the surface of the patient support 56. Alternatively, the may be a three dimensional representation of an idealized patient, or of the patient support 56. The pane 306 preferably also includes a subpane 324 that displays three dimensional representation of the operating region. In this preferred embodiment this representation is an transparent, three dimensional idealized representation of the portion of the patient's body in which the procedure is taking place, e.g. a human heart as shown in FIG. 15. To facilitate the user's interpretation of the image, the image may be displayed over a horizontal backing grid. Instead of an idealized representation of the procedure site, the image could be an actual preoperative image, or an actual current image. A coordinate system is optionally included in the representation to facilitate the user's understanding of the orientation.

The tool bar 304 includes a 3D tool bar 328 with controls for controlling the 3-D display pane 306. In this second preferred embodiment, these controls include a screen manipulation button 330, a grid button 332, a display selector button 334, a constellation button 336; a point centering button 338, a zoom in button 340, a zoom out button 342, and an image capture button 344. These buttons are preferably "virtual buttons", i.e., they are elements on the display which the user can operate by pointing a cursor and clicking.

A view selection menu bar 346 is also provided on the 3D tool bar 328. The view selection menu 346 has an arrow that can be operated to drop down a menu of views to display in the pane 306. These preferably include cranial, caudal, anterior, posterior, left and right, as well as one or more user defined views. Of course other standard views could be provided depending upon the procedures for which the interface is used.

The screen manipulation button 330 can be actuated (for example by right clicking) to display a plurality of screen manipulation options for the cursor. For example, the user can select among a plurality of cursor modes to translate the image on the display 306, to rotate the image on the display, etc., by clicking and dragging the image. The appearance of the cursor on the display 306 preferably changes to cue the user as to the particularly screen manipulation mode in effect. In the translation mode, the cursor might change in appearance, for example to a shape corresponding to the icon on the button 330. In this mode the view point can be changed by grabbing the image by clicking when the cursor is on the image, and dragging the cursor to move the image and thus the viewpoint in any direction. The cursor can be moved using mouse 74 or 82. This preferably also causes a corresponding translation of the view point of the image in the subpane 324.

The grid button 332 can be clicked to show and hide the grid lines on the display 306.

The display selector button 334 allows the user to select the format of the display 306. The user can click on the button to cause a menu of icons depicting various formats to drop down. The user then simply selects the desired format, for example including the subpane 324 (as shown) or removing the subpane 324.

The display constellations button 336 can be operated to toggle between a display in which points on the display 306 are shown as part of a group or constellation (e.g. FIG. 19) by pointing the cursor to the button and clicking, for example with mouse 74 or 82.

The point center button 338 can be operated to enter the point selection mode by pointing the cursor to the button and clicking, for example with mouse 74 or 82. In the point center mode the cursor might change in appearance, for example to a shape corresponding to the shape on the button 338. In this mode the view point for the image can be centered upon a selected point by moving the cursor over a point on image and clicking, for example with mouse 74 or 82.

The zoom in button 340 allows the user to click to enlarge the image on the display 306, and the zoom out button 342 allows the user to click to reduce the image on the display 306 The zoom in button 340 and the zoom out button 342 can be operated to enter the magnification or zoom mode by pointing the cursor to the button and clicking for example with mouse 74 or 82. In the zoom mode the cursor might change in appearance, for example to a shape corresponding to the magnifying glass icon with a "+" for zoom in, and a "–" for zoom out. In this mode the magnification of the image can be accomplished by grabbing the image by pointing the cursor and clicking, and dragging the cursor downwardly and/or to the right to increase the magnification, or upwardly or to the left to decrease the magnification. Changing the size of the patient reference image 306 preferably also does not change the size of the procedure site reference image. 324

The image capture button 344 can be operated to enter the image capture mode by pointing the cursor to the button, and clicking, for example with mouse 74 or 82. This opens a box that allows the user to save the image on the pane 306 for future reference.

The interface preferably displays a visual indicator of the desired orientation for the distal end of the medical device. In this preferred embodiment, this indicator is an arrow 350, whose shaft is aligned with the desired orientation, with a large conical head pointing in the desired direction. The arrow 350 is preferably a distinctive color, e.g. green. The interface preferably also displays a visual indicator of the current orientation of the distal end of the medical device. In this preferred embodiment, this indicator is an arrow 352, whose shaft is aligned with the current orientation of the distal end of the medical device, with a larger conical head pointing in the desired direction. The arrow 352 is preferably a distinctive color, different from the arrow 350, e.g. yellow.

A localization system could be provided for determining the current position and orientation of the distal end of the medical device. An image representative of the distal end of the medical device can then be generated and displayed in the pane 306. There are numerous method for localizing the distal end of the medical device, for example transmitting magnetic signals between one or more reference locations and the medical device, x-ray image processing, ultrasound localization, or electric potential localization.

In the preferred embodiment, the interface is adapted for use with a magnetic navigation system that operates by generating a magnetic field of selected direction in the operating region, which causes a magnetically responsive element associated with the distal end of the medical device to generally align with the applied field. Because of the physical properties of the catheter, limitations in the strength of the applied field, and the conditions in the procedure site, the distal end of the medical device may not align precisely with the applied magnetic field. While the difference between the applied magnetic field and the actual direction of the distal end of the medical device can be accounted for through modeling or a look-up table, in the preferred embodiment the arrow 350 representing the desired orientation may represent the desired direction of the applied magnetic field, rather than the desired direction of the medical device itself. Similarly, the arrow 352 representing the current orientation may represent the direction of the magnetic field to currently being applied, rather than the actual direction of the device itself. However, the differences between the actual direction of the medical device and the applied magnetic field can be characterized by equation or an empirically determined look-up table, or localization of the device can be provided so that even when used with a magnetic navigation system, the arrow 350 represents the actual desired orientation of the medical device, and arrow 352 represents the actual current direction.

As in the first preferred embodiment, in the second preferred embodiment, the interface includes displays of the fluoroscopic images of the operating region, with the arrow 350 superposed thereon. For example, as shown in FIGS. 6A and 6B, the imaging system 68 can provide biplanar images of the operating region, and the arrow 350 on each image. These images could be displayed on monitors 86 an 88 in the procedure room 50, and on monitor 90 in the control room 52.

Preferably, the user can change the direction of the arrow 150 on these images by rotating and translating the arrow as described above.

While the orientation of the distal end of the medical device can be manipulated directly on the pane 306, the display 100' of the interface preferably includes at least one pane to aid the user in selecting the desired orientation for the medical device, and thus of the arrow 350. In this preferred embodiment there are several panes that provide alternative methods for the user to select the desired orientation for the distal end of the medical device. These panes include representations of the orientation of the arrow 350 which are constantly updated, so that use of one pane to change the desired direction of the medical device, causes all of the other panes to update, to facilitate the use of any of the panes to adjust the orientation of the arrow 350 representing the desired new orientation of the medical device.

One such pane to aid the user in selecting the desired orientation for the medical device is the 2-D anatomical pane 308, which allows the user to select the desired orientation of distal end of the medical device as indicated by the arrow 350 by adjusting the direction in one or more planes through the patient. As shown in FIG. 15, the pane 310 allows the user to change the direction of the arrow 350 in at least one plane, and preferably at least two planes and more preferably at least the planes. These planes are preferably, but not necessarily, mutually perpendicular. While adjustment in two planes is sufficient to specify any direction, providing adjustment in three planes makes it easier for a user to select the desired direction for the arrow 350. In this preferred embodiment, the arrow 350 can be rotated in the coronal or frontal plane (i.e., about an anterior-posterior axis), the median or saggital plane (i.e., about a horizontal axis), and the horizontal or transverse plane (i.e., about a longitudinal axis).

Figure 16:
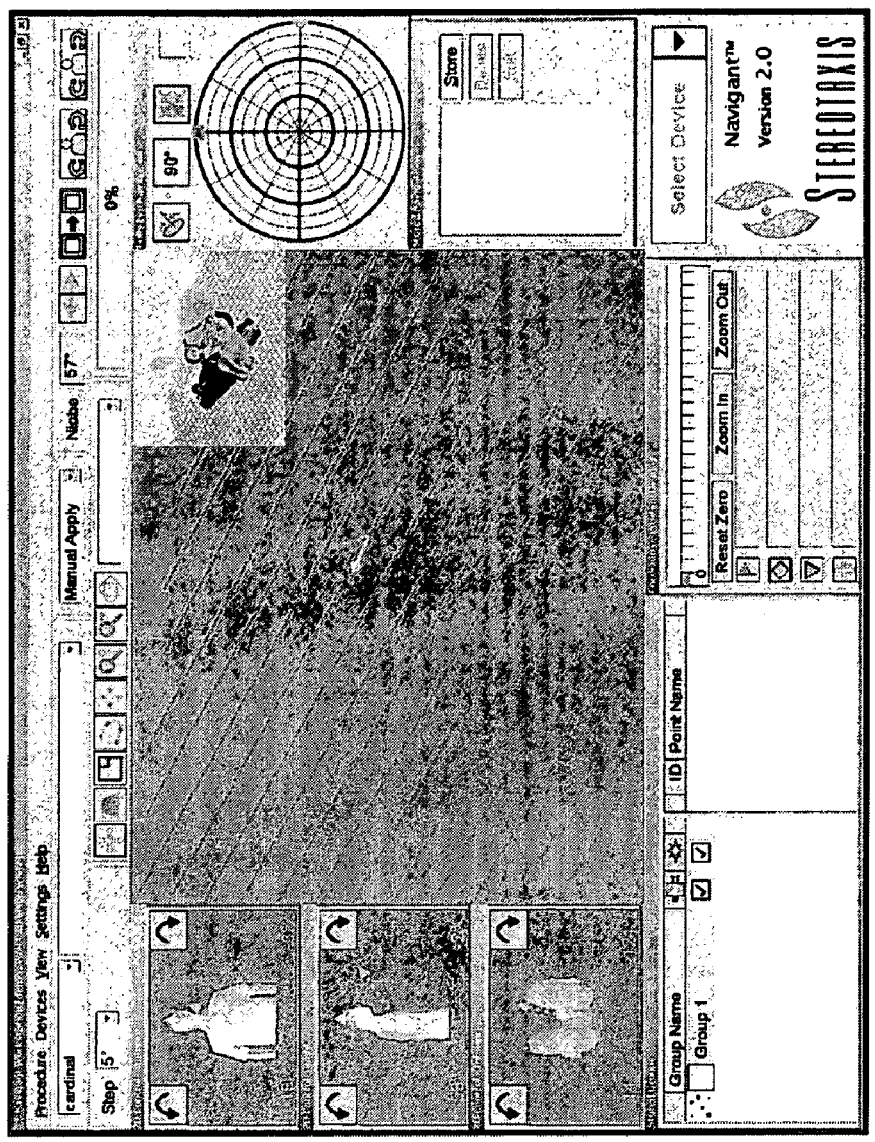
FIG. 16 is a view of the display of the second preferred embodiment of the interface of this invention, showing an alternate image in pane 308.

As shown in FIGS. 15-19 the pane 308 can have three graphic displays 360, 362 and 364, corresponding to the three planes of rotation. As shown in FIGS. 15 and 16, the user can preferably select between an anatomy view (FIG. 15) or a whole body view (FIG. 16). Graphic display 360 contains a graphic depiction of the coronal or frontal plane (e.g. a caricature image of the organ and/or operation region or a caricature image of a patient's body, in the coronal or frontal plane), with an indicator 366 that indicates the orientation of the arrow in the coronal or frontal plane, and virtual buttons 368 and 370 for moving the indicator 366 (and thus the arrow 350) clockwise or counterclockwise in the coronal or frontal plane abut the anterior-posterior axis. In this preferred embodiment, indicator 366 is actually a projection of the arrow 350 in the plane, and thus the length of the indicator 366 is indicative of the orientation. The virtual buttons 368 and 370 can be operated with a cursor for example with the mouse 74 or 82 or the keyboard 80, to point and click the button and move the indicator 366 and thus the arrow 350, in the desired direction. Display 362 contains a graphic depiction of the median or saggital plane (i.e., a caricature image of a patient's body in the median or saggital plane), with an indicator 372 indicating the direction of the arrow 350 in the median or saggital plane, and virtual buttons 374 and 376 for moving the indicator 372 (and thus the arrow 350) clockwise or counterclockwise in the coronal or frontal plane. In this preferred embodiment, indicator 372 is actually a projection of the arrow 350 in the plane, and thus the length of the indicator 372 is indicative of the orientation. The virtual buttons 374 and 376 can be operated with a cursor for example with the mouse 74 or 82 or the keyboard 80, to point and click and move the indicator 372 and thus the arrow 350, in the desired direction. Display 364 contains a graphic depiction of the horizontal or transverse plane (i.e., a caricature image of a patient's body in the horizontal or transverse plane), with an indicator 378 indicating the direction of the arrow in the horizontal or transverse plane, and virtual buttons 380 and 382 for moving the indicator 378 (and thus the arrow 350) clockwise or counterclockwise in the horizontal or transverse plane. The virtual buttons 380 and 382 can be operated with a cursor for example with the mouse 58 or 66 or the keyboard 64, to point and click to move the indicator 278, and thus the arrow 250 in the desired direction.

The pane 308 also includes a menu 384 to select the increment of change in direction upon operating the buttons 368 and 370, 374 and 376, and 380 and 382. The user can select the incremental change from 1 degree, 2 degrees, 3 degrees, 5 degrees, 10 degrees with a cursor for example with the mouse 74 or 82 or the keyboard 80, to point and click to select the desired increment.

Instead of using controls 368 and 370, 374 and 376, and 380 and 382, to incrementally move the indicators 366, 372. and 378, the user can simply point and click on the three graphic displays 360, 362 and 364 to move the indicator to the selected point. Moving the indicators either with controls 368 and 370, 374 and 376, and 380 and 382, or by selecting points on the displays 366, 372, and 378, the user can selected the direction of arrow 350.

Figure 19:
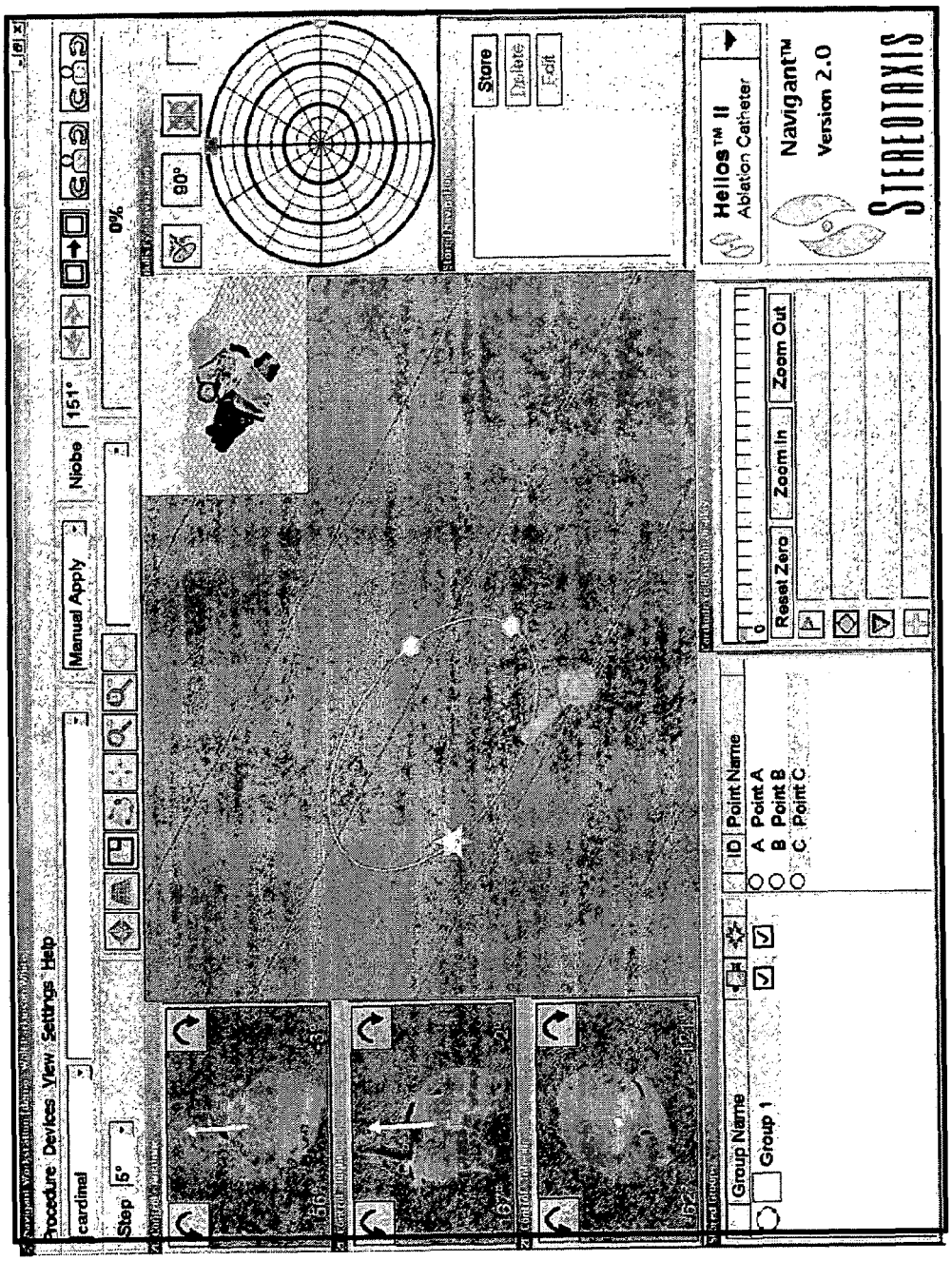
FIG. 19 is a view of the display of the second preferred embodiment of the interface of this invention, showing an elliptical constellation of points and a possible path of a medical device to the constellation.
Figure 20:
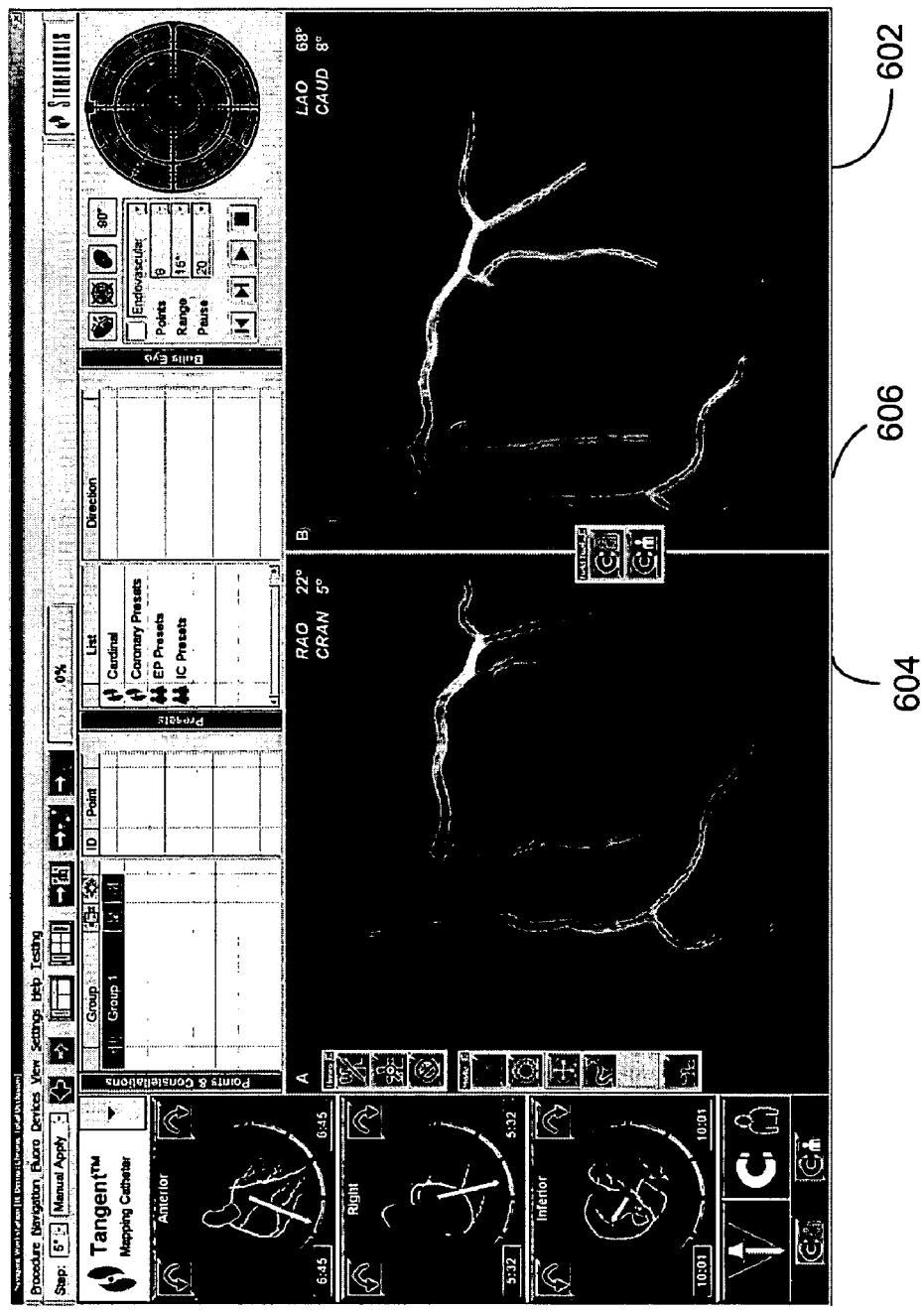
FIG. 20 is a view of a display of a third preferred embodiment of an interface in accordance with the principles of this invention, with two main panes.
Figure 21:
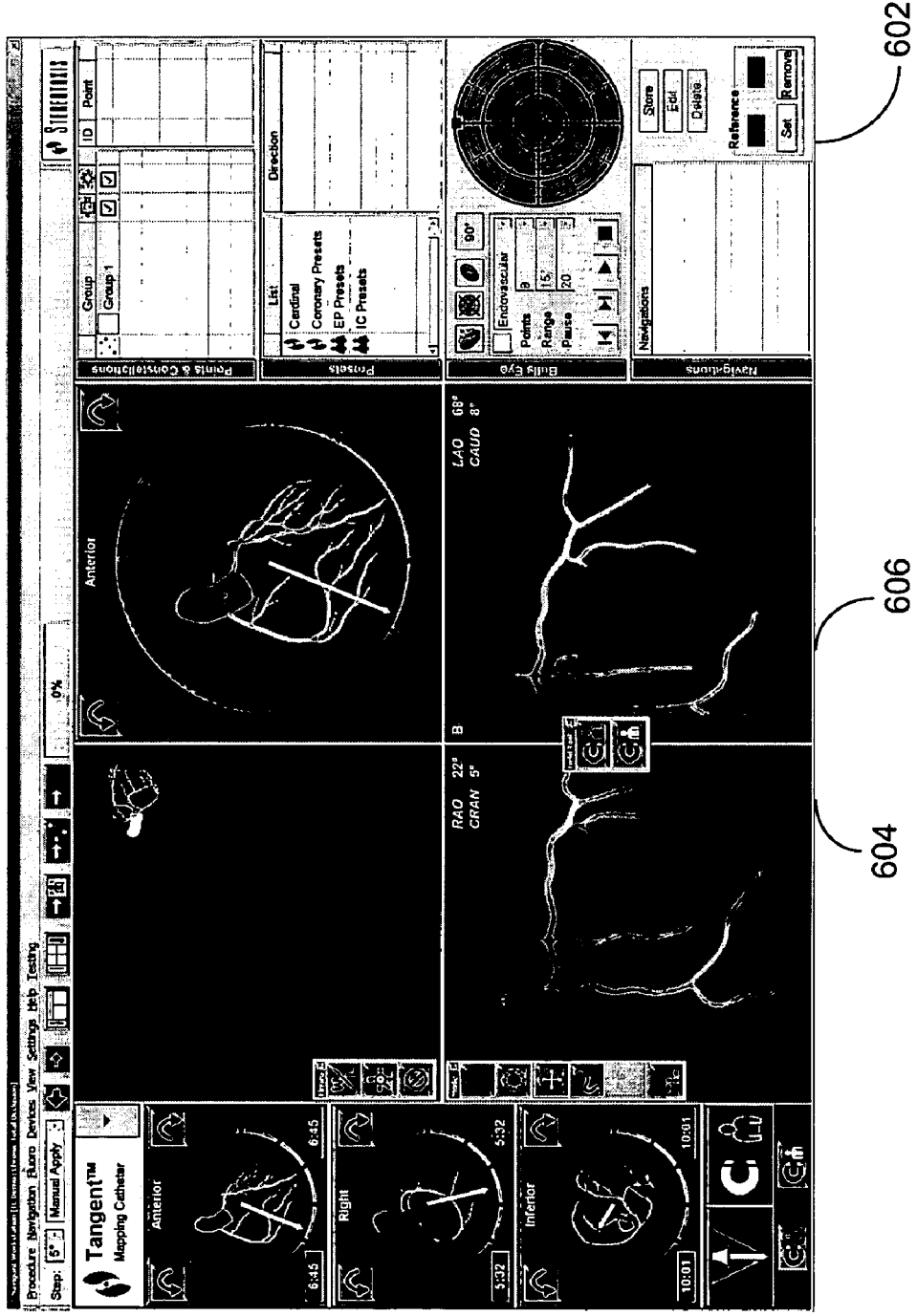
FIG. 21 is a view of a display of a third preferred embodiment of an interface of the third embodiment, with four main panes.

Another pane to aid the user in selecting the desired orientation for the arrow 350, and thus for the medical device, is point navigation pane 310. As shown in FIG. 15, the point navigation pane 310 includes a group menu table 400 containing information about one or more groups of points the user identifies. The group menu table 400 includes a column 400*a* for an icon for identifying the arrangement of the group (a group of points can be thought of as defining a shape, such as a circle, ellipse, or spline much the same way that stars for constellations of shapes). An icon representing unorganized points is shown in FIG. 15, a icon representing an ellipse "constellation" is shown in FIG. 19. Other types of arrangements of points in a group, for example points on fitted curve, and points on a spline, can be identified with different icons in the column 400*a*. A column 400*b*, with the heading "Group Name" includes a color/shape identifier and a name for the group, e.g. "Group 1". In this second preferred embodiment, a square of a color identifying the group is displayed in column 400*b*, but the group could be identified in some other manner. All points in a group will be indicated with a mark in the indicated color, as described in more detail below. The group menu table 400 further includes a column 400*c* for a pick box for each group for indicating whether the group should be shown on the bi-plane fluoroscopic imaging screens (on monitors 86, 88, and 90), and a column 400*d* for a pick box for each group for indicating whether the group should be shown on the 3D display in pane 306.

The identified of points, groups of points, and constellations of points within a group allows the user to simply identify a point or points and have the interface determine the field direction to reach the point or points The pane 310 also includes a point menu table 408. The menu table 408 includes a column 408*a*, for an identification symbol that indicates (preferably using color) the group to which the point belongs, a column 408*b* entitled "ID" that contains a code assigned by the system to a particular point (in this second preferred embodiment the system assigns an ID sequentially from A to ZZ). The menu table 208 further includes a column 208*c*, entitled "Point Name" for a user specified name of the point. The user can select a group by pointing the cursor on a group in the group menu table 400, which causes the point menu table 408 to display each of the points in the selected group.

As a further aid to the user in selecting the desired orientation for the medical device, vector navigation pick menus 428 and 430 are provided on the toolbars 304. The pick menu 428 displays a "preset list" pick menu for selecting a particular set of predetermined directions, and the pick menu 430 displays a "direction" pick menu for selecting a particular direction from the set selected in window 428. A set of possible "preset list" and "direction" entries for the pick menus 428 and 430 is shown in Table 2. The user can select from the "preset list" and "direction" pick menus using the mouse 74 or 82 or keyboard 80.

TABLE 2

Possible Preset Lists and Directions

| | |
|---|---|
| Cardinal | Superior |
| Cardinal | Inferior |
| Cardinal | Anterior |
| Cardinal | Posterior |
| Cardinal | Left |
| Cardinal | Right |
| Cardinal | RAO |
| Cardinal | LAO |
| Deflection | Increasing deflection from 0 to 175° in 15° increments |

Vector history buttons 432 and 434 are also provided on one of the tool bars 304 to aid the user in selecting the desired orientation for the medical device. The buttons 432 and 434 allow the user to move backwardly and forwardly through an automatically stored list of applied magnetic field directions, in order to reapply a previously applied magnetic field. The buttons 432 and 434 allow the user to set the orientation of the arrow 350 to one of the previously selected directions, which are automatically stored. In the preferred embodiment, the system automatically stores the last ten directions, and the user can scroll backward and forward through these directions with the buttons 432 and 434. The appearance of the buttons 432 and 434 preferably changes (e.g. grays out) when the there is no further stored directions.

The interface can also include a vector storage and recall pane 312 to store, recall, and use custom directions. The direction vector storage and recall pane 312 includes a vector menu table 436, and associated "store" button 438, "delete: button 440, and "edit" button 442. The buttons 438, 440, and 442 are preferably virtual buttons, or portions of the display to which the cursor can be pointed and clicked, for example with the mouse 74 or 82, or the keyboard 80. The "store" button 438 can be operated by pointing and clicking with the cursor using the mouse 74 or 82 or keyboard 80, and allows the user to store the current direction under a user selected name on the vector menu table 436. Operating the store button 438 allows the user to input a name for the stored direction. The user can selected a previously stored direction from the menu table 436 by pointing to the name with the cursor, and clicking, using the mouse 74 or 82, or keyboard 80. The "edit" button 442 can be operated by pointing and clicking with the cursor using the mouse 74 or 82 or keyboard 80, and allows the user to edit the name of a selected direction. The "delete" button 440 can be operated by pointing and clicking with the cursor using the mouse 74 or 82 or keyboard 80, and allows the user to delete a selected direction.

Figure 17:
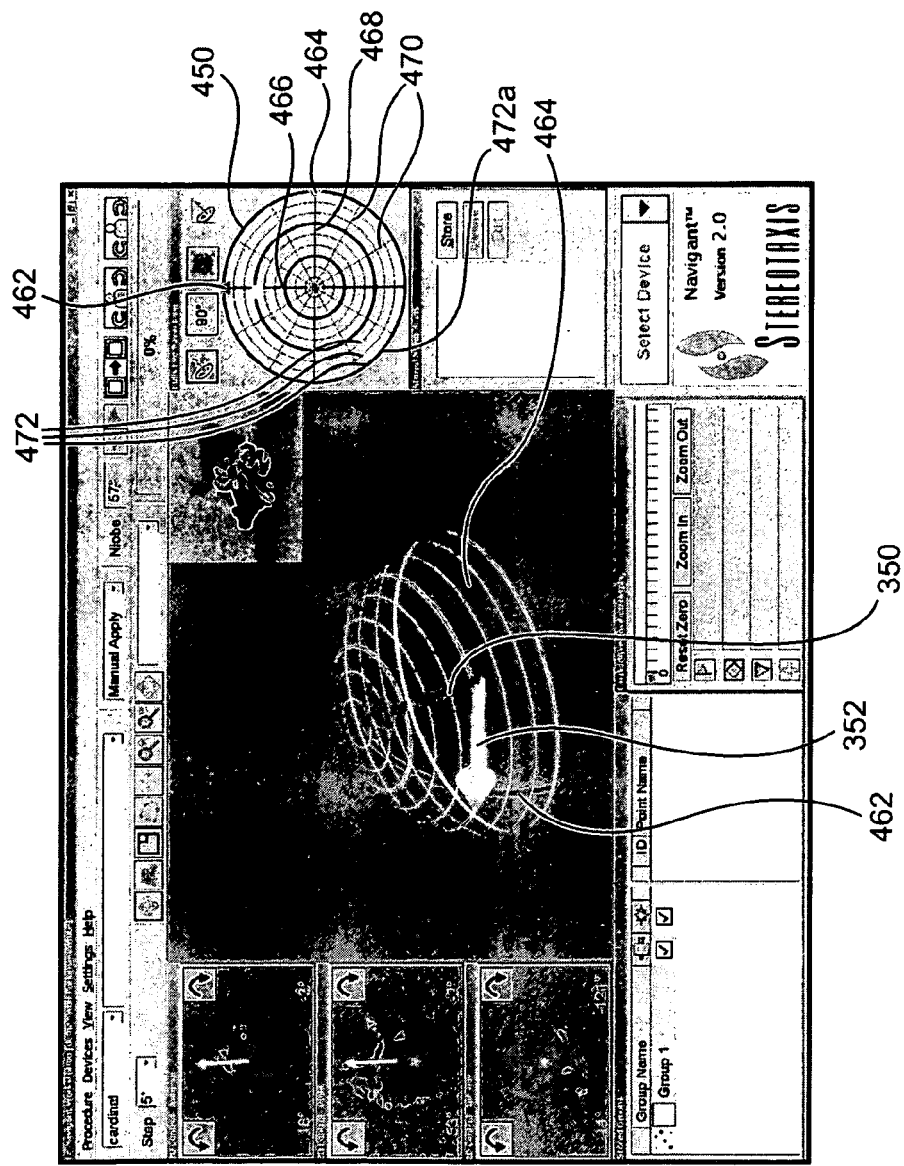
FIG. 17 is a view of the display of the second preferred embodiment of the interface of this invention, showing the use of target navigation pane 314.
Figure 18:
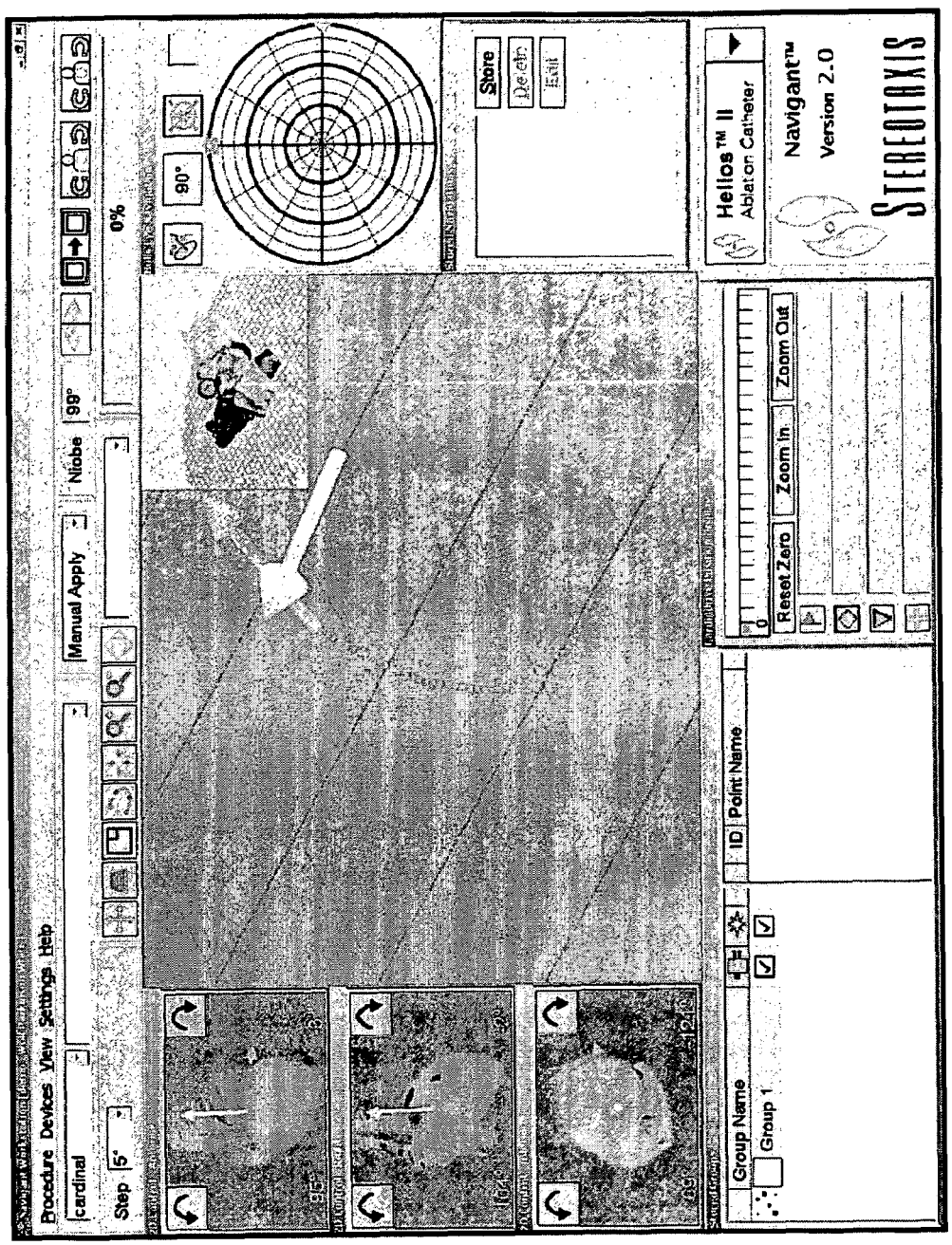
FIG. 18 is a view of the display of the second preferred embodiment of the interface of this invention, showing a possible path of a medical device.

The bull's eye navigation pane 314 includes a circular screen 450, and an "apply" button 452. The pane 314 also includes a scale menu 454, which in the preferred embodiment allows the user to select the scale of the screen 450 from 15, 20, 45, 60, 90, and 120 degrees. The user can select the desired scale for the circular screen 250 by pointing the cursor at the scale menu 454, to display a list of scales, and selecting and clicking on the desired scale, using the mouse 74 or 82 or keyboard 80. FIG. 17 shows the circular screen 450 on the display pane 306. As shown in FIG. 17, markers 462 and 464 are provided on the circular screen 450, to help the user interpret the orientation of the circular screen 450 on the 3D pane 306 and the on the RAO and LAO views. The marker 262 might be blue and the marker 264 might be red.

The user can set the base direction the navigation pane 116 by operating the "apply" button 452 by pointing at the button with a cursor and clicking, using mouse 74 or 82 or keyboard 80. This sets the current direction as the direction though the center of the screen 450. The user can then specify a direction for the arrow 350 by selecting a point on the screen 450, by pointing with the cursor and clicking, using mouse 74 or 82, or keyboard 80. As shown in FIG. 17, the screen 450 has vertical and horizontal cross hairs 466 and 468, and a plurality of radially extending markers 470, at 30 degree intervals. There are a plurality of concentric circular markers 472 representing regular angular intervals (10 degree intervals in the preferred embodiment), with specified intervals (30 degree intervals in the preferred embodiment) indicated by bold markers 472*a*. The circular screen 450 actually represents a hemisphere of space, and is represented as such with hemisphere 450' on display 306 in FIG. 17. The hemisphere 450' includes markers 462' and 464' corresponding to the markers 462 and 464 on circular screen 450. The screen 450 allows the user to orient the arrow 350 at a number of points to draw radial and circular lines.

The toolbar 304 preferably also includes an indicator 480, an apply button 482, a reduce button 484, and an angle indicator 486. The indicator 480 allows the user to select among a "manual apply" mode, in which the user must affirmatively apply the selected field, an "automatic" mode in which the selected field direction is automatically applied, and a "locked" mode in which the field cannot be applied without changing the mode to either "manual apply" or "automatic". The apply button 482 and the reduce button 484 are preferably virtual buttons which are operated by pointing the cursor and clicking, for example with mouse 74 or 82, or keyboard 80. Operating the apply button 482 when the interface is not in the automatic or locked modes causes the magnetic navigation system to apply a magnetic field to orient the distal end of the medical device in the orientation of the arrow 350. Operating the reduce button 484 causes the magnetic navigation system to "turn off" the magnetic field. The indicator 486 indicates the angular difference between the previously applied magnetic field (arrow 352) and the desired new orientation (arrow 350). Of course rather than discrete navigation, in which the arrow 350 is successively oriented and the magnetic field applied, the interface could be adapted to operate in a continuous navigation or automatic mode in which the field is automatically applied in the direction of arrow 350.

The interface also includes an advancer control pane 316. The advancer control pane 316 displays the length of extension of the medical device being navigated. The pane 316 has three buttons: a reset zero button 490, a zoom in button 492, and a zoom out button 494. The pane 316 also has three user settable flags 496, 498 and 500, and one system settable flag 502. The user can use the reset zero button 490 to reset the current extension of the medical device as the zero position. The user can advance and retract the medical device using the zoom in and zoom out buttons 494 and 496. The extension of the medical device from its zero position is displayed as a colored bar on the scale 504. The user can set three flags to mark desired locations by operating the virtual buttons 496, 498, and 500. Operating any one of the buttons causes the corresponding flag to appear on the scale 504, and allows the user to name the flag for future reference. In modes where the system automatically calculates the applied magnetic field and extension to reach a particular target, the system displays the path of the device a dashed line, the required field as a green arrow, and the required extension by positioning the system flag 502 on the scale 504. This aids the user in extending or retracting the medical device to the proper position to reach the target.

The interface also includes an information block 318, displaying the version of the software, and including a pick window 506 to allow the user to select the particular type of device being navigated. The properties of the device are then used in calculating and displaying the configuration of the device to reach a selected point, and determining the required magnetic field and device extension to reach the desired point.

Operation

In operation the user can visualize the current direction of the device represented by arrow 352 and the desired new direction for the device represented by arrow 350, on the 3-D pane 306 or on the x-ray images on monitors 86, 88, and 90. The user can selected the orientation of the arrow 350 in a number of ways using panes 308, or 310, or 314, using the menus 328 and 330 on the tool bars 304, or simply selecting a point in the three dimensional display, and allowing the system to calculate the field and direction to reach a selected point 16. See FIG. 18.

The user can select the orientation of arrow 350 (representing the magnetic field to apply) in a variety of ways. On pane 308 the user clicks on buttons 368 and 370, 374 and 376, and 380 and 382, to move the arrow 350 in each of the coronal or frontal plane, the median or saggital plane, and the horizontal or transverse plane to move the arrow. Alternatively, the user can select the orientation of arrow 350 by using the pane 312. The user selects a point on the menu table 408 by pointing and clicking with the cursor to set the orientation of arrow 350 to the orientation associated with point selected. Alternatively, the user can select the orientation of arrow 350 using the pane 312. The user can select a stored orientation by selecting a category on menu 428, and a direction on menu 430. The user can select a user-stored direction by selecting a direction vector from the menu table 436. The user can select a previously used direction by using the buttons 432 and 434 to recall one of the last previously used direction. Finally, the user can select an orientation by picking a point on a screen 450 in pane 314.

Once the direction of the arrow 350 is selected, the navigation system can be operated by operating the apply button 482. This can operate a magnetic navigation system to apply a field in the direction 350, or it can operate a magnetic navigation system to apply a field to cause the medical device to align in the direction 350, either by using feedback of the catheter position or by calculating or using a look-up table to account for the properties of medical device.

A third embodiment of an interface is illustrated in FIGS. 20-26. The interface is adapted for controlling a magnetic navigation system that applies a magnetic field in a selected direction to an operating region in a subject to magnetically orient a medical device in the operating region. The interface comprises a display 602 on which at least one image of the operating region is displayed, and in this preferred embodiment the display has panes 604 and 606 for displaying images of the operating region from two different planes, to facilitate identifying points in three dimensional space in the operating region. The interface further comprises an input device, such as a mouse (not shown) for identifying points in the operating region on the at least one image on the display, for example by moving a cursor or other indicator over the display, and "clicking" on the selected point. Of course the interface could be any other device for identifying points on the display, including joysticks, touch screen displays, light pens, etc. By identifying a point on the image on each of the panes 604 and 606, a user can uniquely identify a point in three-dimensions in the operating region.

Figure 24A:
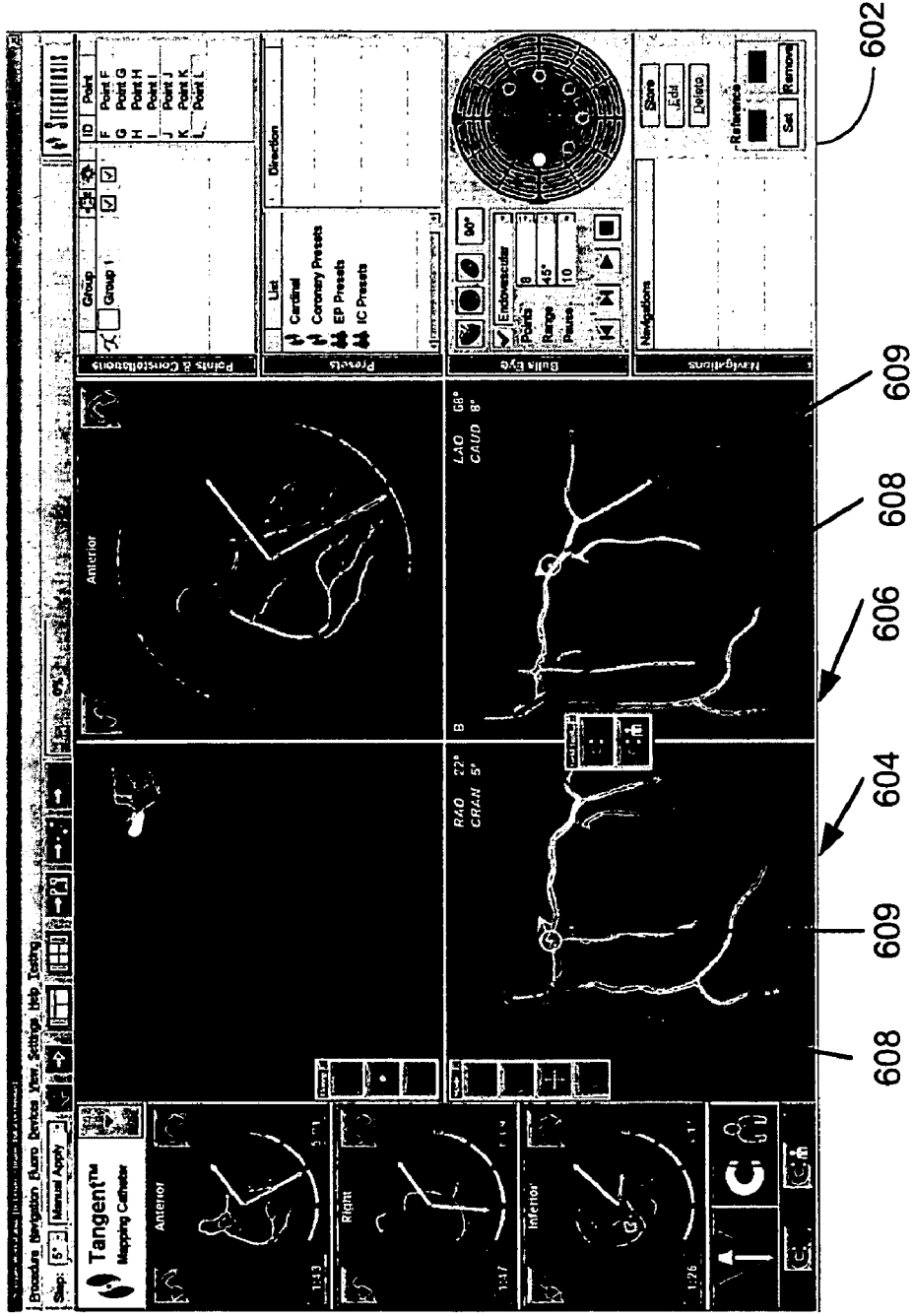
FIG. 24A is a view of a display of the third preferred embodiment, with biplanar images in the main panes, showing the specification of a navigation field at an application point.
Figure 24B:
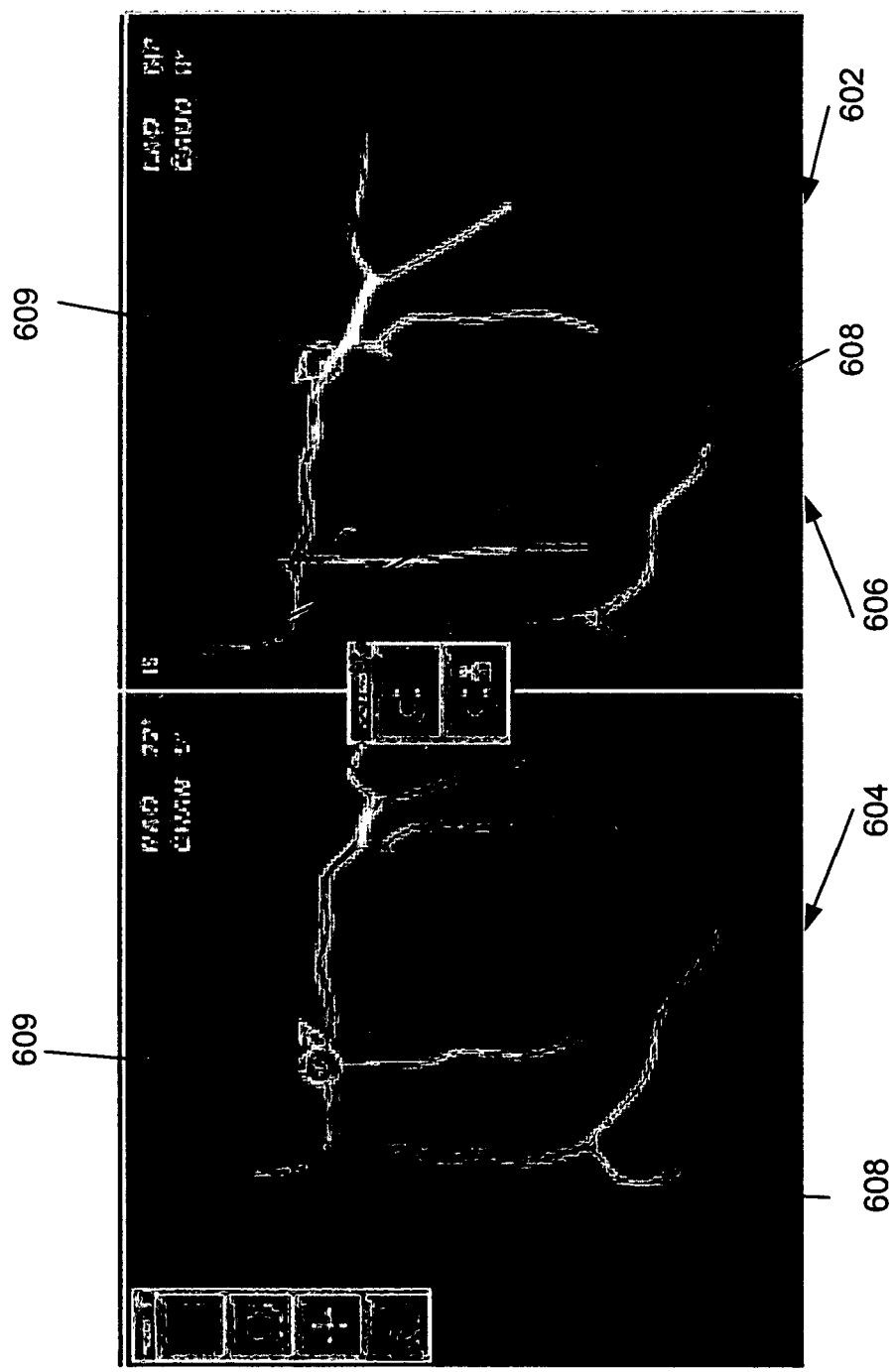
FIG. 24B is an enlarged view of the biplanar images in the main pane of FIG. 24A.
Figure 25A:
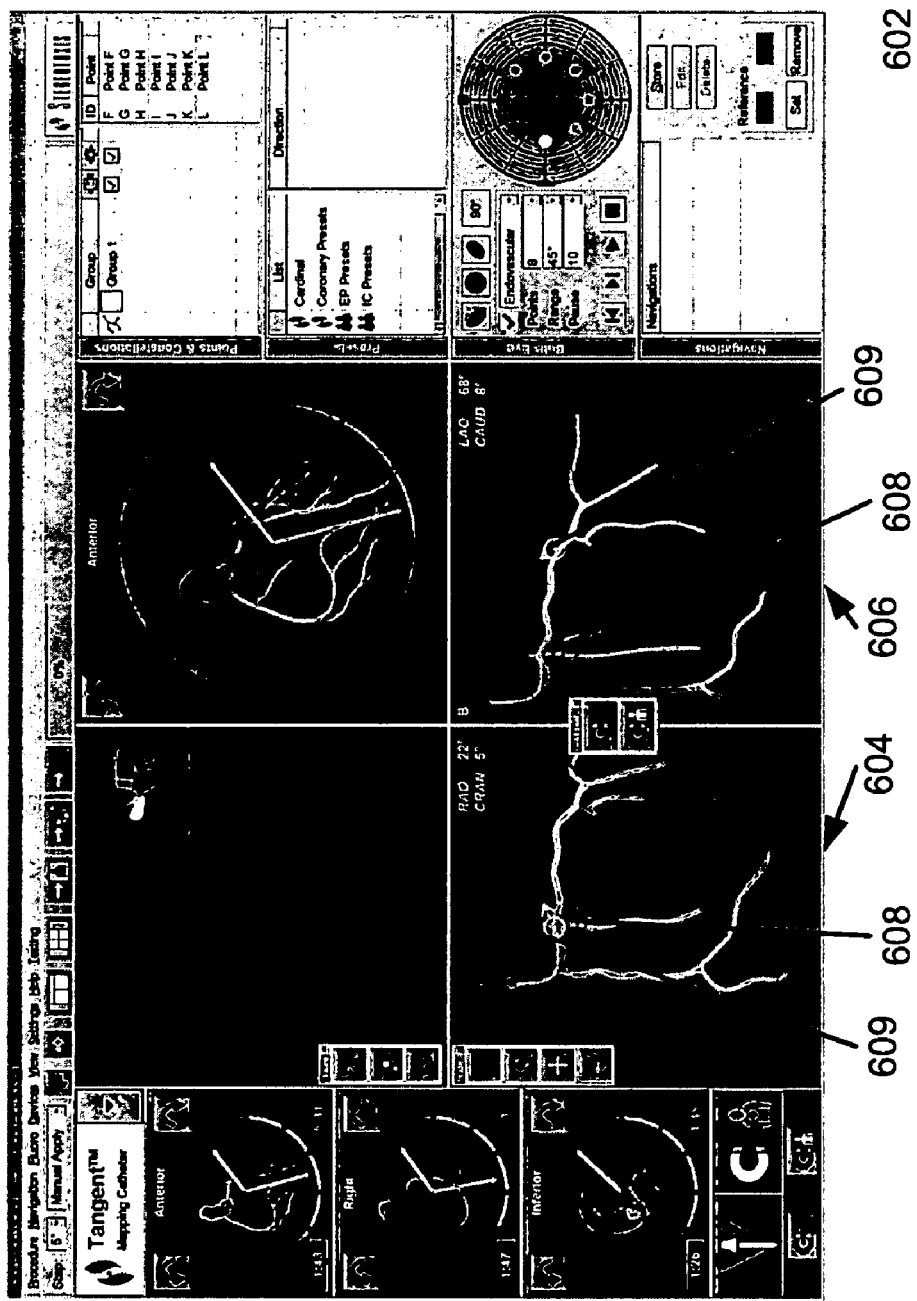
FIG. 25A is a view of a display of the third preferred embodiment, with biplanar images in the main panes, showing the specification of a navigation field at an application point.
Figure 25B:
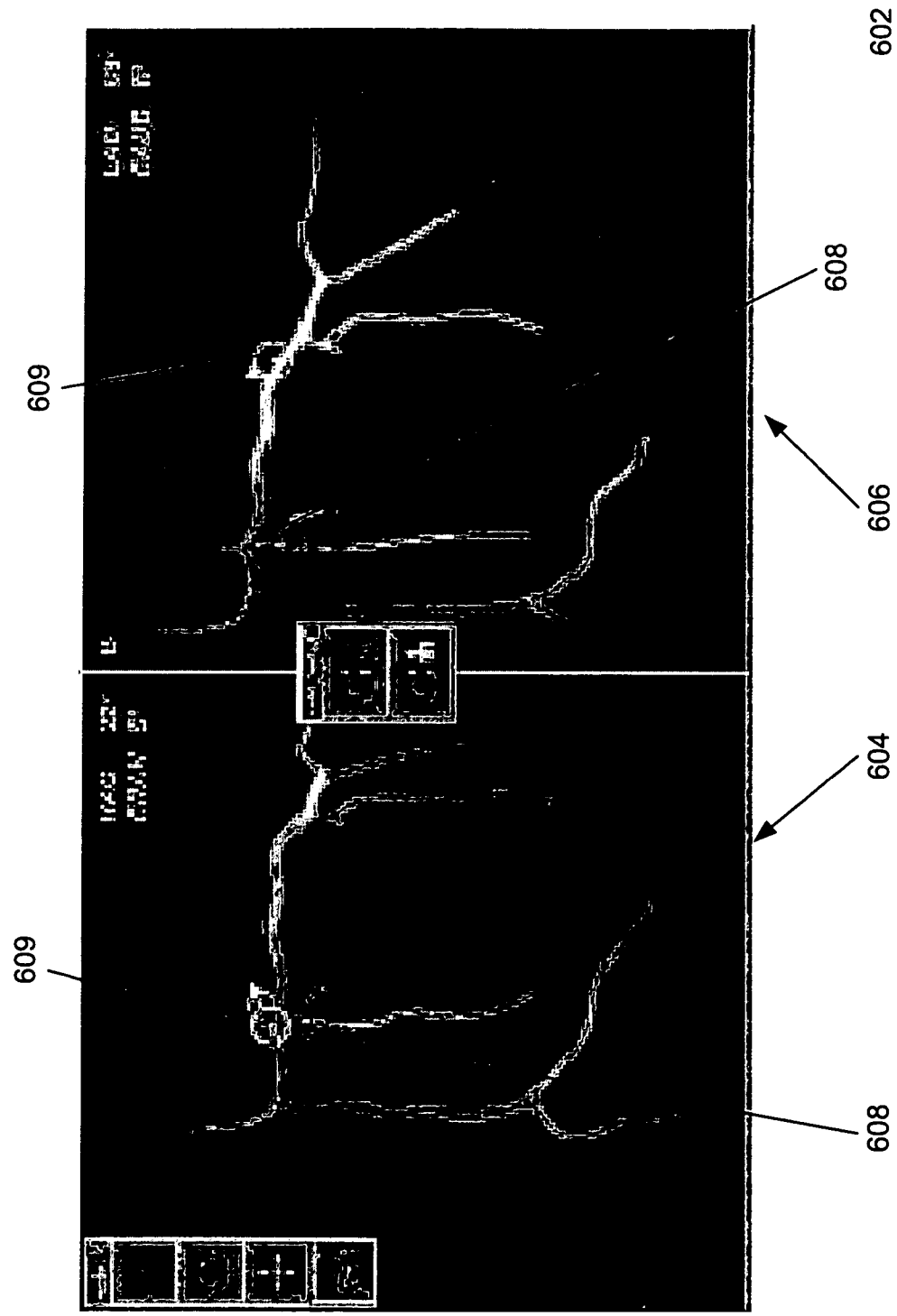
FIG. 25B is an enlarged view of the biplanar images in the main pane of FIG. 25A.

The interface includes a processor that, after the user selects a point in the operating region, determining an application point in the operating region which is on a predetermined branched path through the subject's vasculature and which is closest to the identified point. The interface then determines (e.g., by calculation or use of a reference table) the direction that is tangent to the predetermined branched path at the application point. As shown in FIGS. 24 and 25, this direction can be displayed by indicators 608, which may be color coded to distinguish them from indicators 609 of the previously applied direction. The interface, preferably through the processor, then causes the magnetic navigation system to apply a magnetic field at the application point, in a direction tangent to the predetermined path at the application point.

Figure 22A:
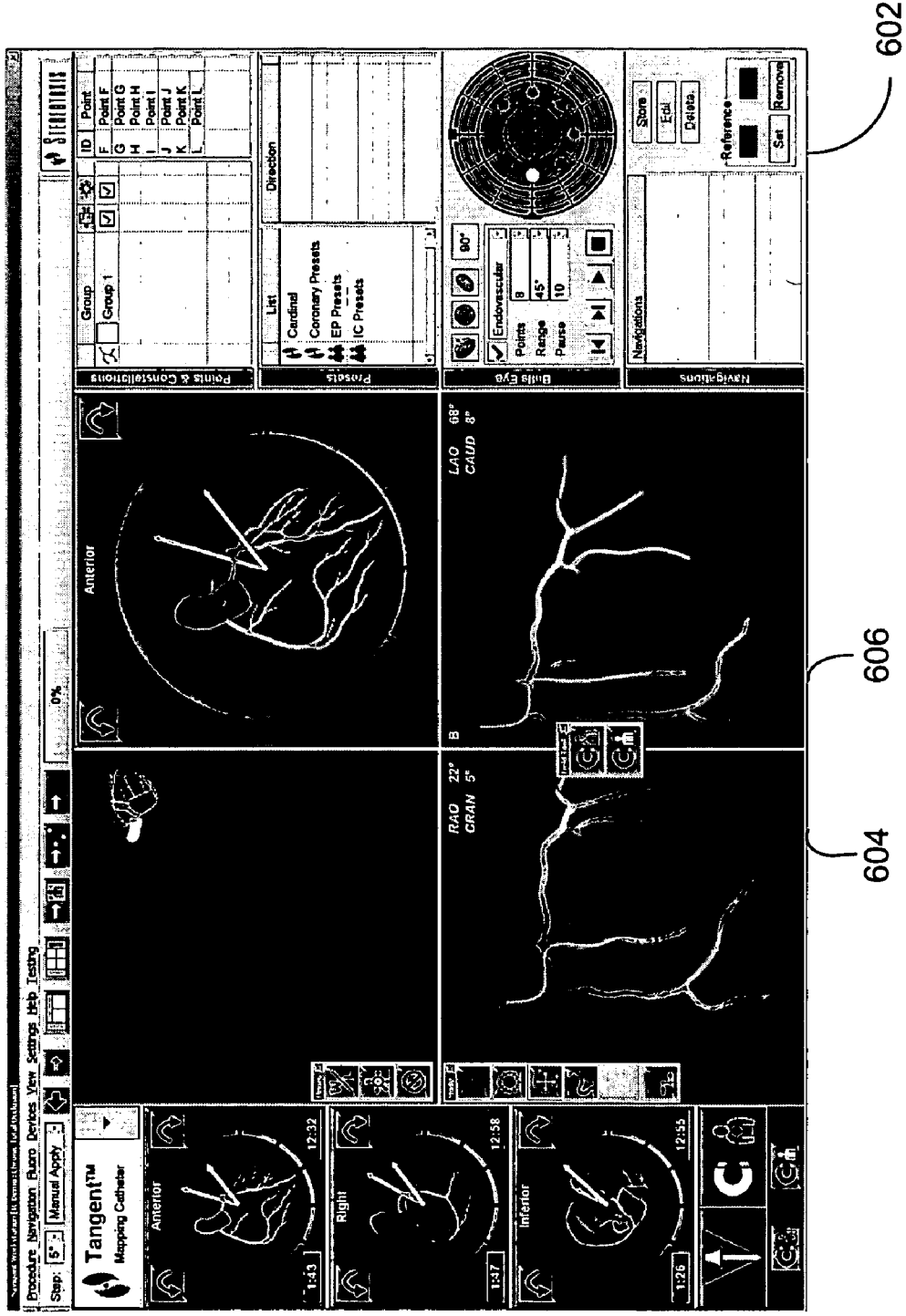
FIG. 22A is a view of a display of the third preferred embodiment, with biplanar images in the main panes, showing the selection of a point in creating a predetermined branched path.
Figure 22B:
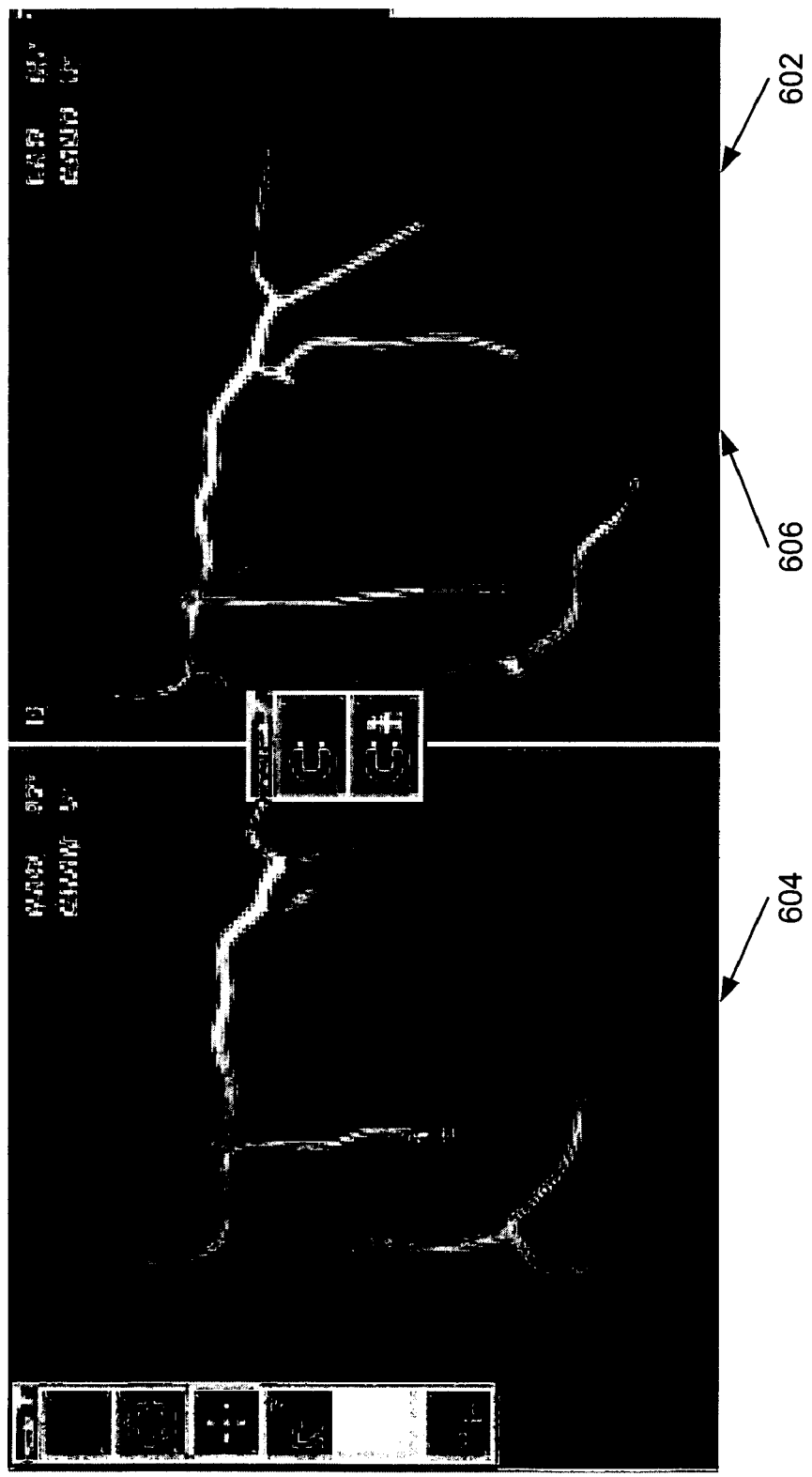
FIG. 22B is an enlarged view of the biplanar images in the main panes.
Figure 23A:
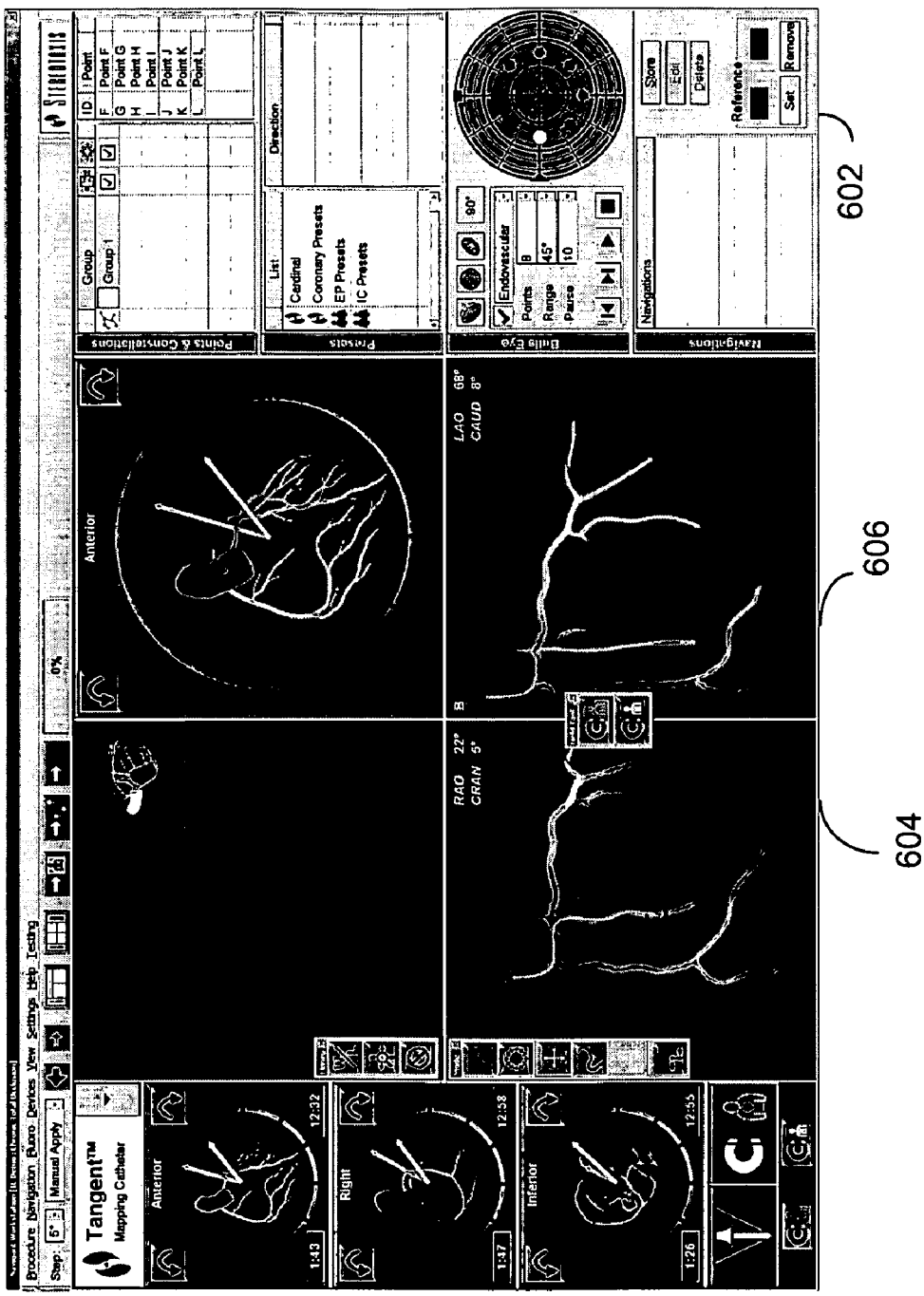
FIG. 23A is a view of a display of the third preferred embodiment, with biplanar images in the main panes, showing the completion of a predetermined branched path.
Figure 23B:
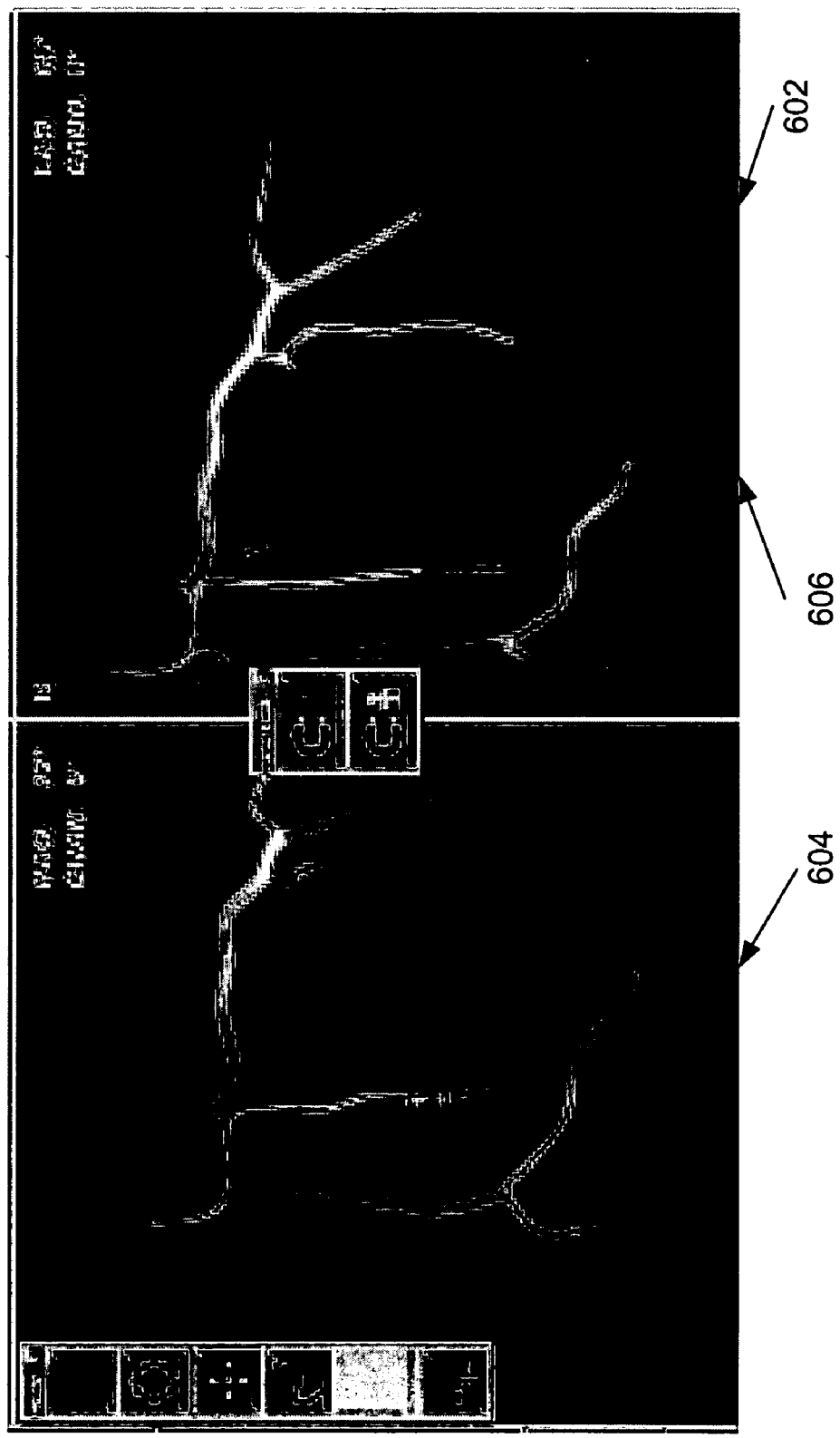
FIG. 23B is an enlarged view of the biplanar images in the main pane of FIG. 23A.
Figure 26A:
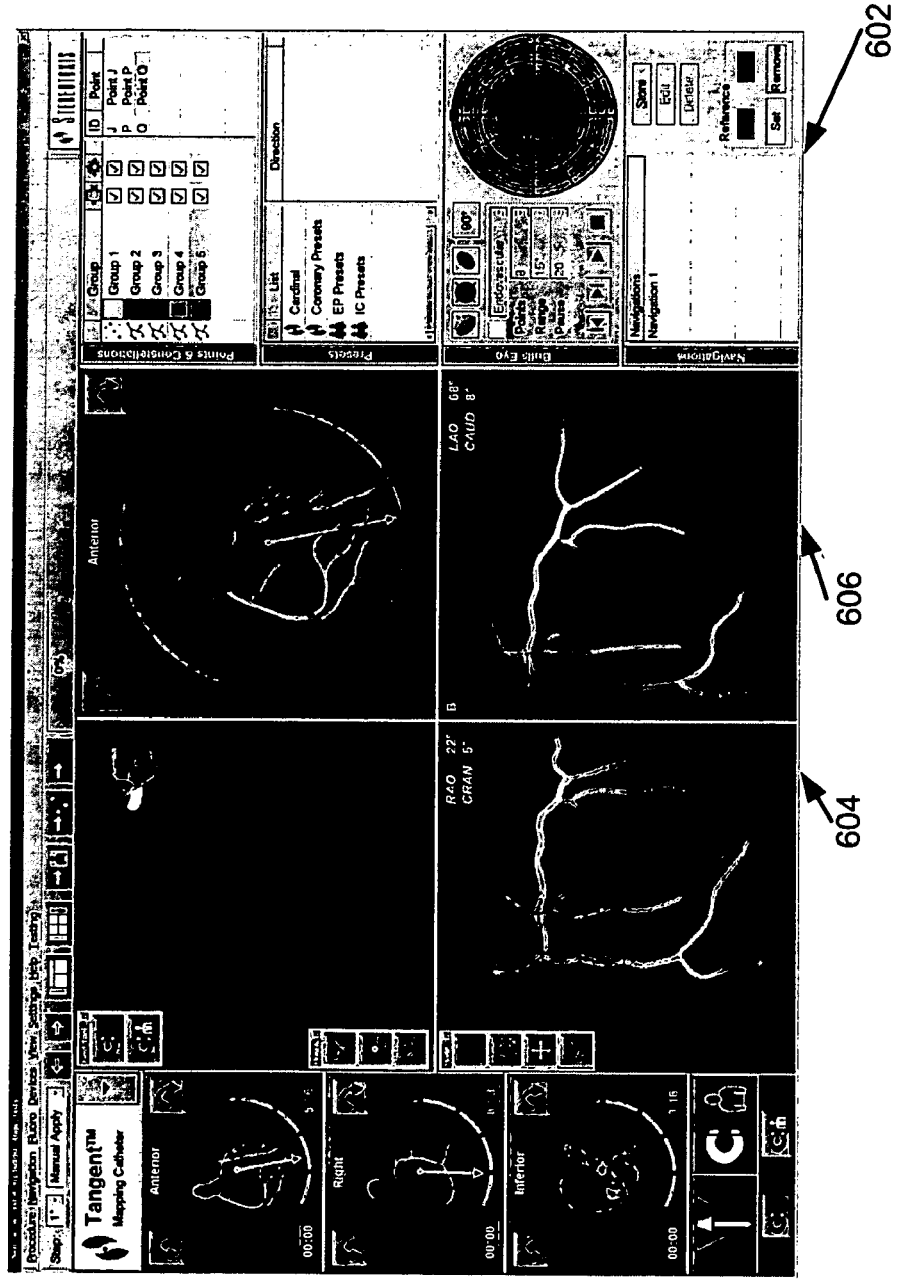
FIG. 26A is a view of a display of the third preferred embodiment, with biplanar images in the main panes, showing the exemplary branched path.
Figure 26B:
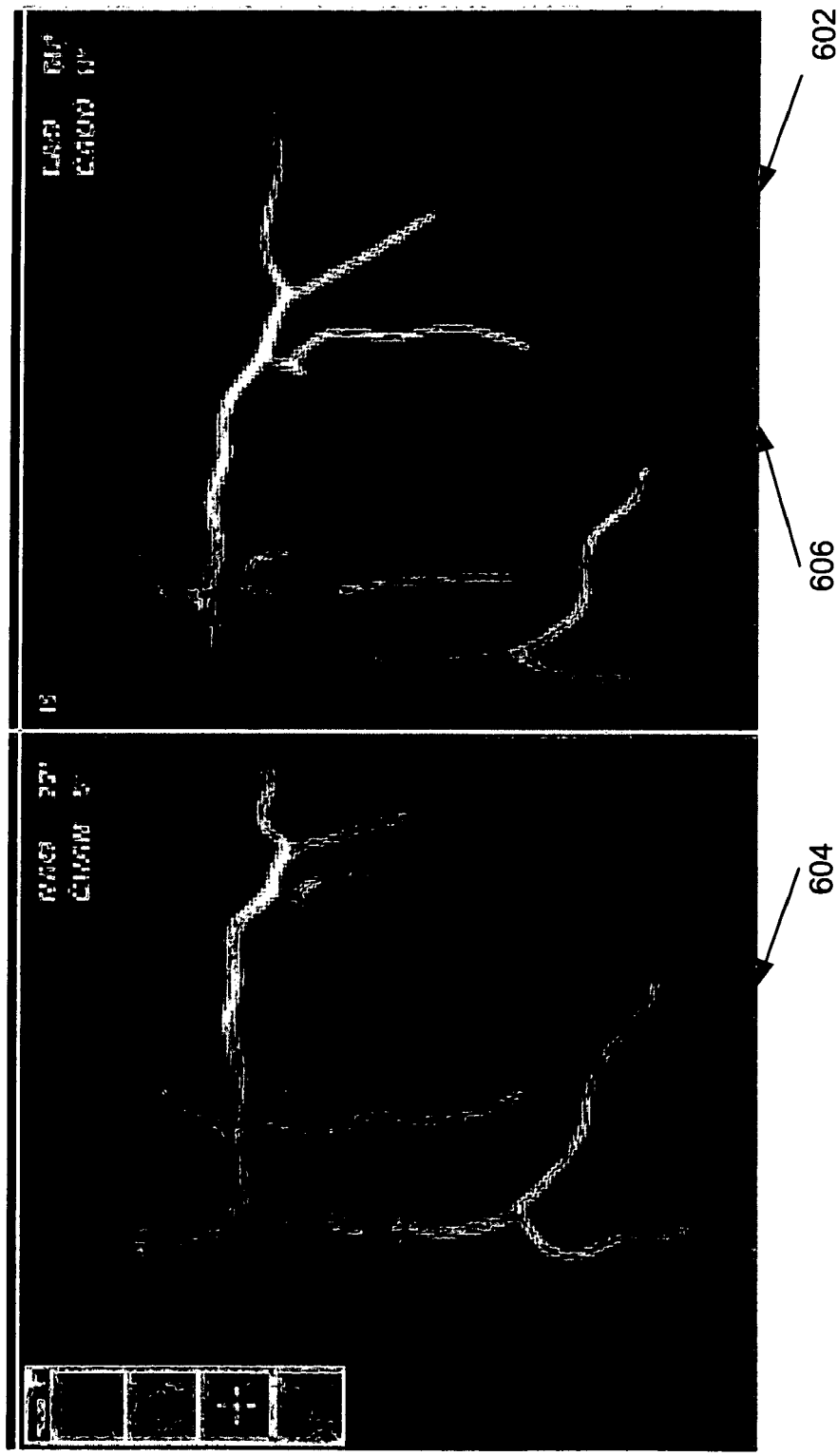
FIG. 26B is an enlarged view of the biplanar images in the main pane of FIG. 26A.

As shown in FIGS. 22 and 23, the predetermined branched path can be manually determined prior to beginning the procedure. A user can use the interface to identify a plurality of points on the vasculature in the operating region, uniquely identifying each point in three dimensional space by identifying it on the two panes 604 and 606, using the input device (see FIG. 22). After points have been identified along the vasculature, the processor can automatically connect the points to form the predetermined branched path by connecting each point with its next nearest neighbors (see FIG. 23). The processor then can overlay or superimpose the predetermined branched path over the images of the operating region on the panes 604 and 606, so that the user can verify the accuracy of the branched path, and make adjustments if necessary. As shown in FIG. 26, each branch can be displayed in a different color to help the user visualize the operating region. This is particularly helpful when viewing the operating region in two planes on the panes 604 and 606. Where the vasculature curves, or is branched, the points must be identified fairly closely together, while wherein the vasculature in straight and unbranched, the user does not have to identify as many points. Alternatively, the predetermined branched path can be determined through image processing, which can be assisted by the injection of contrast medium, if necessary.

Thus the processor creates the predetermined branched path through the vasculature in an operating region in a subject's vasculature, by accepting the identification of a plurality of points on the subject's vasculature on at least one image of the operating region; and connecting each point with its nearest neighboring point to form the branched path through the vasculature.

The interface thus can be used to operate a magnetic navigation system to apply a magnetic field in a selected direction in an operating region in a subject, to magnetically orient a medical device in the operating region. The user first identifies a plurality of points along the subject's vasculature in an image of the operating region in the subject. The user then connecting each point to the closest adjacent point to create a network of navigable paths through the subject's vasculature. This can be done manually, but is preferably done automatically by a computer processor. The user then identifies a point where on the image of the operating region, where the user wants to navigate. The computer processor can then determine an application point that is on the previously determined network of navigable paths, closest to the selected point. The computer processor also determines the direction tangent to the network of navigable paths at the application point. The interface then causes the magnetic navigation system to apply magnetic field at the application point in a direction tangent to the navigable path at the application point.

The interface accepts the identification of a selected point on an image of the operating region, determines an application point on a predetermined navigable path through the subject's vasculature in the operating region corresponding that is closest to the selected point; and applies a magnetic field at the application point in a direction tangent to the navigable path at the application point. A magnetic navigation system incorporating the interface may have one or more stationary electromagnetic coils, or one or more movable electromagnets and/or permanent magnets. The interface selectively powers the stationary electromagnets, selectively powers and moves the moveable electromagnets, or selectively moves the permanent magnets to apply the appropriate magnetic field at the operating point in the selected direction.

Another control of the interface of the third embodiment is illustrated in FIG. 27. This control operates a magnetic navigation system that applies a magnetic field in a selected direction to an operating region in a subject to magnetically orient a medical device in the operating region. The interface facilitates the specification of the direction of the magnetic field to be applied by the magnetic navigation system, and includes a display pane 610 on which a representation 612 of the current orientation of the medical device (or the currently applied magnetic field) is displayed. In this preferred embodiment the representation 612 is a dot 614 at the center of a circular grid 616 comprising a plurality of concentric circles 618 representing angular deflections from the axis of the medical device. The display pane 610 also includes a selector 620 for selecting one of a plurality of predetermined patterns of new orientations. The interface includes a input device for selecting one of the plurality of patterns of new orientations. This input device may be a mouse and/or a keyboard for operating the selector. Of course, some other input device, such as a joystick, touch screen, etc. could be used for selecting a pattern, The selector 620 includes a pick box 622 for selecting the type of pattern. In this preferred embodiment there are preferably at least two types of patterns, a circular pattern generally concentric about the current position of the medical device, and a spiral pattern originating at the current position of the medical device. The selector preferably also includes a pick box 624 for selecting the number of new positions in the pattern. The selector preferably also includes a pick box 626 for selecting the angular displacement of the pattern from the current position. The selector may also include a pick box 628 for selecting the delay between movement among the positions in the pattern. Lastly, the selector 620 can include a previous position virtual button 630, a next position virtual button 632, a play virtual button 634, and a stop virtual button 636.

The user selects the type of pattern in pick box 622, the number of new positions in the pattern in pick box 624, the angular displacement of the pattern in pick box 626, and if desired a delay time in pick box 628. The selected pattern is displayed on the circular grid 616 as a plurality of dots 638. The user can then operate the magnetic navigation system by clicking on the virtual buttons 630, 632, 634, and 636. Operating button 630 causes the interface to operate the magnetic navigation system to the previous position in the pattern. Operating virtual button 632 causes the interface to operate the magnetic navigation system to the next position in the pattern. Operating the virtual button 634 causes the interface to operate the magnetic navigation system to successively move to each position in the pattern. Operating the virtual button 634 stops automatic operation of the interface.

Figure 27A:
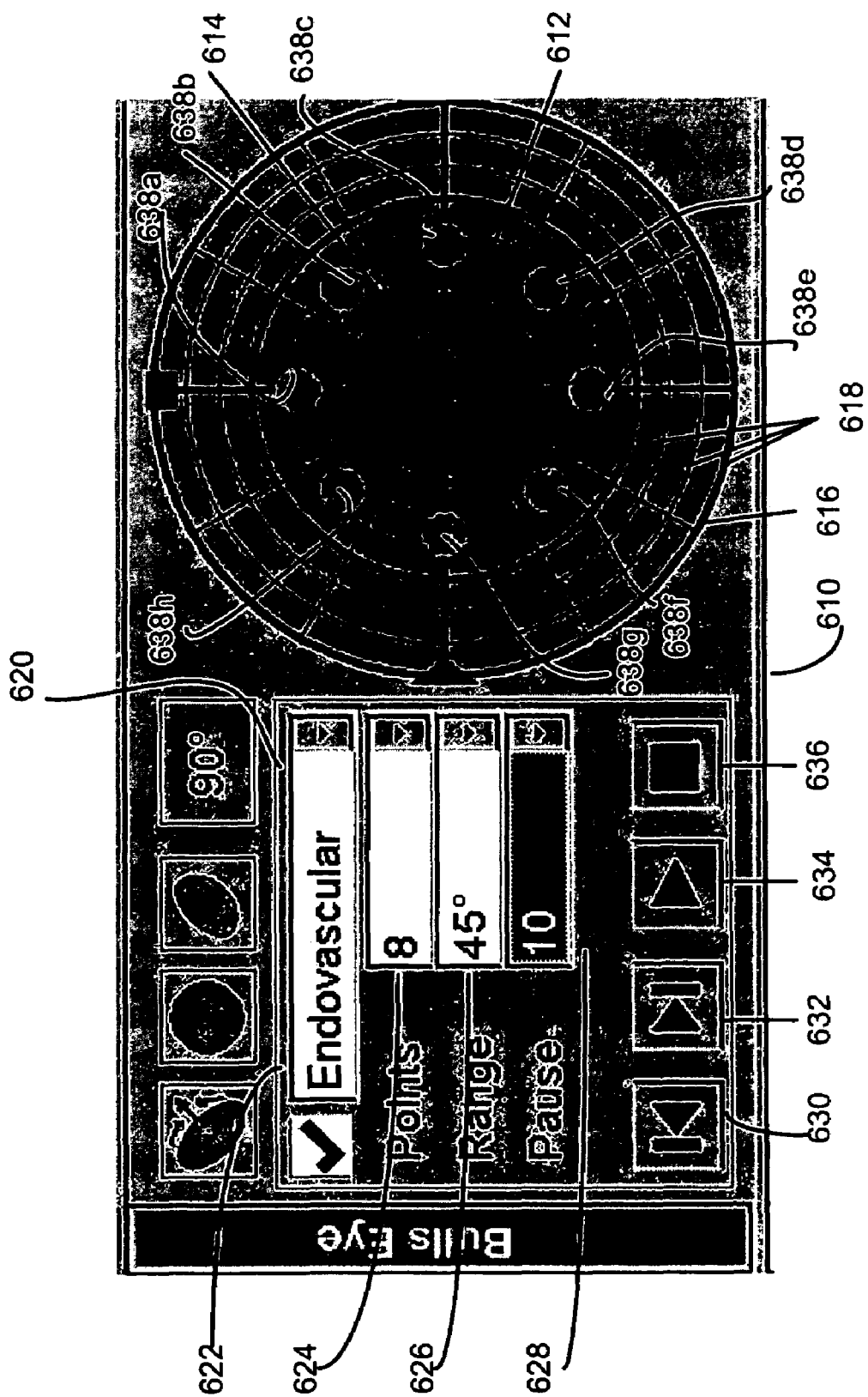
FIG. 27A is an enlarged view of a pattern navigation control pane of the third preferred embodiment of this invention.
Figure 27B:
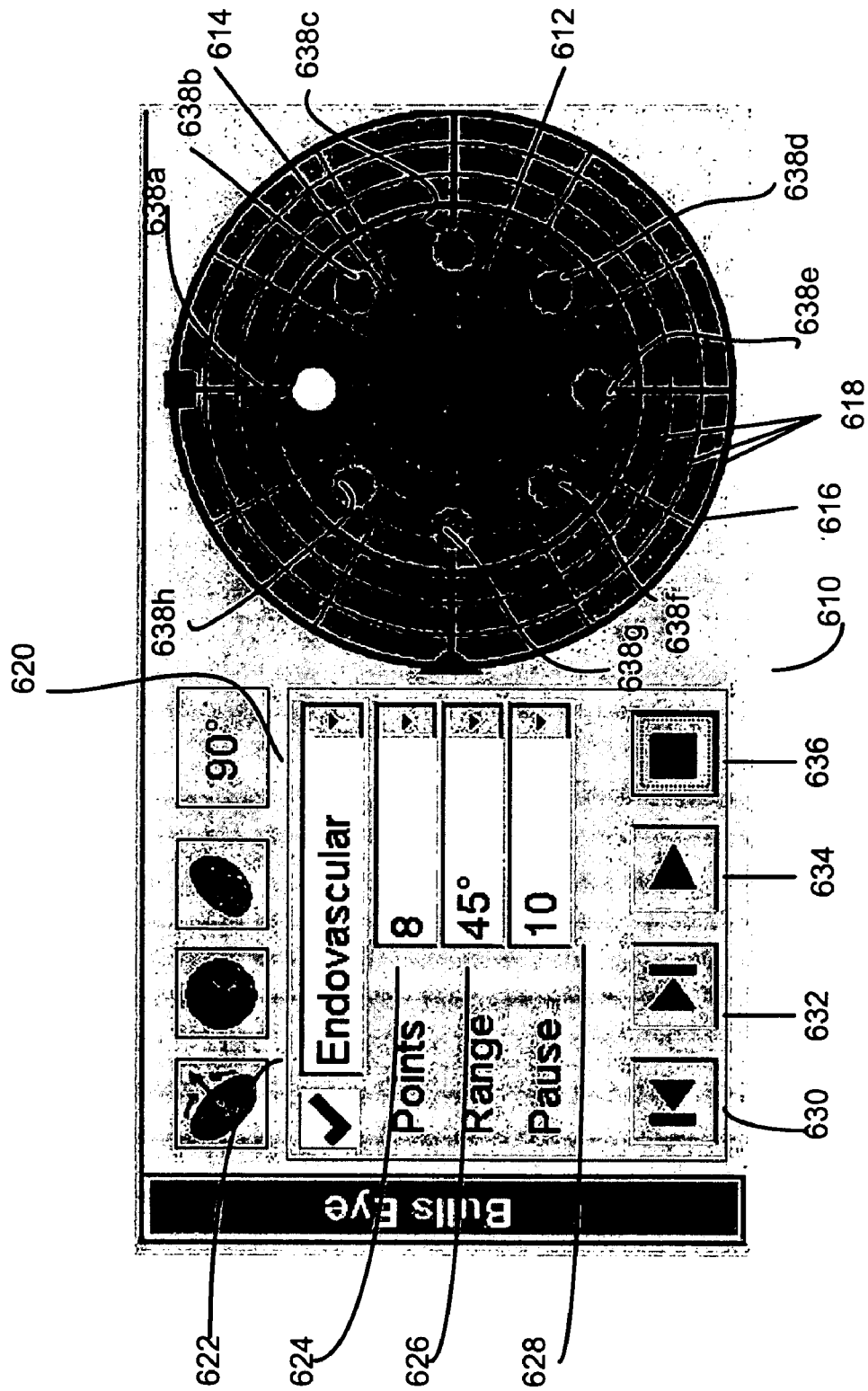
FIG. 27B is an enlarged view of the pattern navigation control pane after navigation of the medical device to the first new position in the pattern.
Figure 27C:
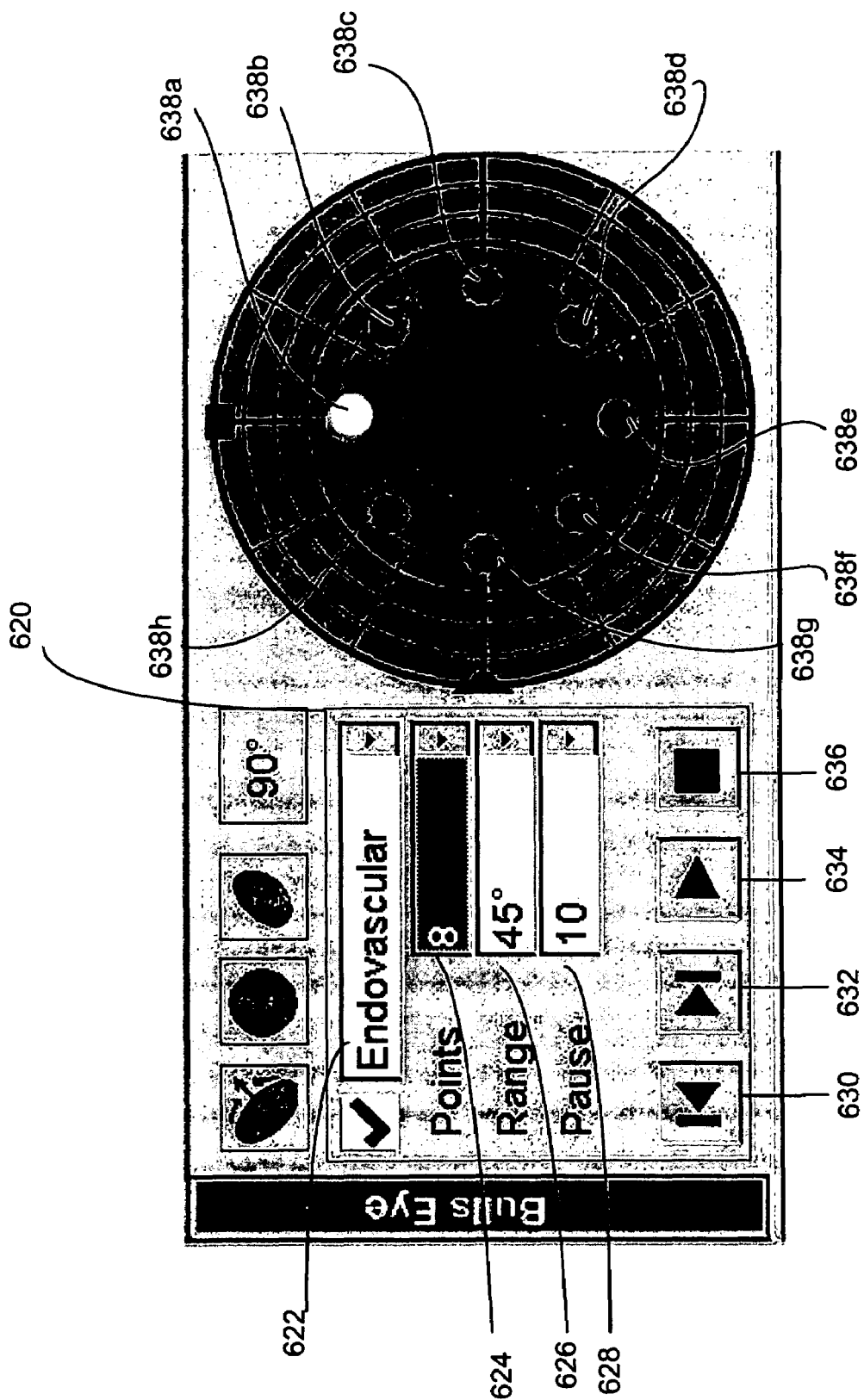
FIG. 27C is an enlarged view of the pattern navigation control pane as the medical device is moved from the first new position in the pattern to the second new position.
Figure 27D:
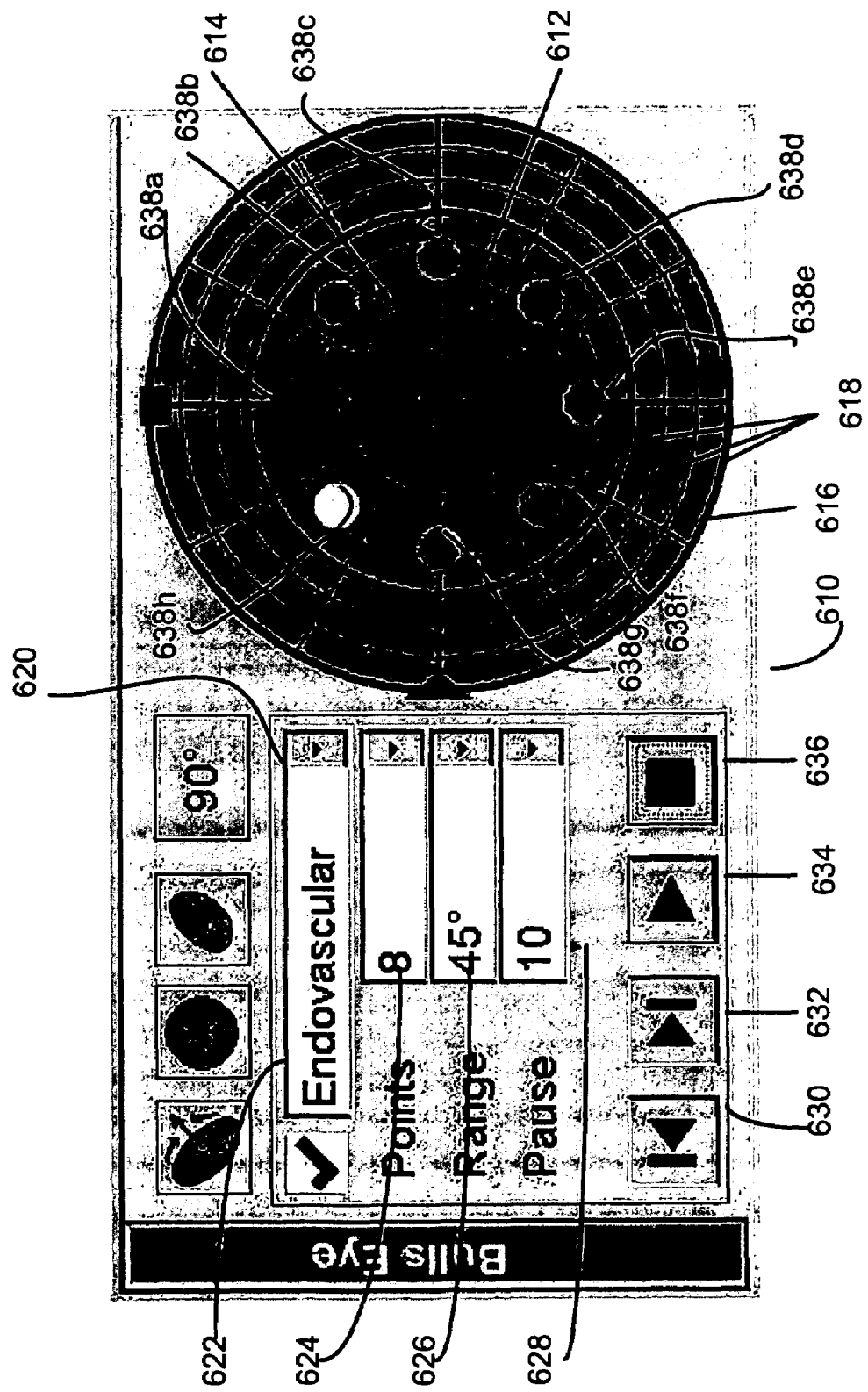
FIG. 27D is an enlarged view of the pattern navigation control pane after navigation of the medical device to the second new position in the pattern.

The colors of the representations of the new positions 638 in the pattern preferably indicate the status of each position. For example, as shown in FIG. 27B, the dots 638*b*-638*h* are a first color (e.g. light grey), indicating that the medical device has not yet been operated to those positions. The dot 638*a* is a second color (e.g. yellow), indicating it is the current position of the medical device. As shown in FIG. 27C the dots 638*b*-638*h* are in a first color, the dot 638*a* is a second color and a dot of a third color (e.g. green) indicating the movement of the field appears behind dot 638A. As shown in FIG. 27D, dot 638*a* is a fourth color (e.g. dark grey) indicating that the medical device has already been navigated to the position, the dot 638*h* is not the second color, indicating it is the current position of the medical device, and dots 638*b*-638*g* are the first color, indicating that the medical device still has not been navigated to these positions.

This pattern navigation, and automated pattern navigation, make it easy to navigate the medical device for selected procedures. For example in mapping procedures, wherein it is desirable to move a mapping catheter to trace an electrical signal, automated movement in a circular or spiral or other pattern facilitates the mapping procedure. Similarly, in ablation procedures, where the user needs to move the tip of an ablation catheter to form a closed loop of ablation, automated movement in a circular or other pattern facilitates the ablation procedure.

In operation the user can use the interface to operate a magnetic navigation system to apply a magnetic field in a selected direction in an operating region in a subject, to magnetically orient a medical device in the operating region. The user selects one of a plurality of predetermined patterns of new positions for the medical device using the selector 320 and an input/output device, such as a mouse. The user then simply manually operates the magnetic navigation system to successively orient the medical device in each new position of the pattern by operating virtual button 632 or initiate the system automatically moving from position to position after the predetermined delay by operating virtual button 634.

A magnetic navigation system incorporating the interface may have one or more stationary electromagnetic coils, or one or more movable electromagnets and/or permanent magnets. The interface selectively powers the stationary electromagnets, selectively powers and moves the moveable electromagnets, or selectively moves the permanent magnets to apply the appropriate magnetic field at the operating point in the selected direction.

Figure 28:
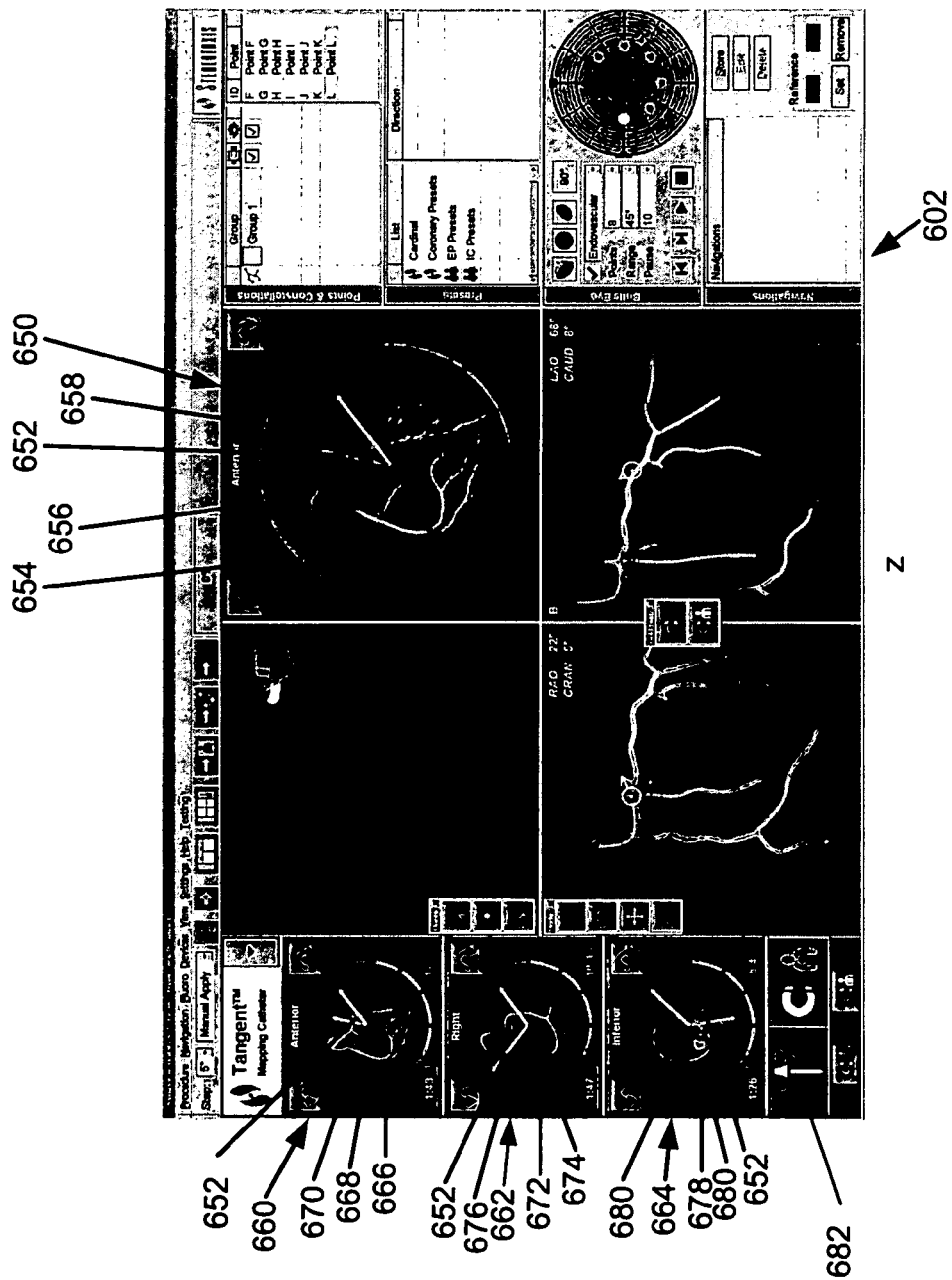
FIG. 28 is a view of a display of a third preferred embodiment of an interface in accordance with the principles of this invention, showing another control for specifying the direction of the magnetic field to be applied.
Figure 29:
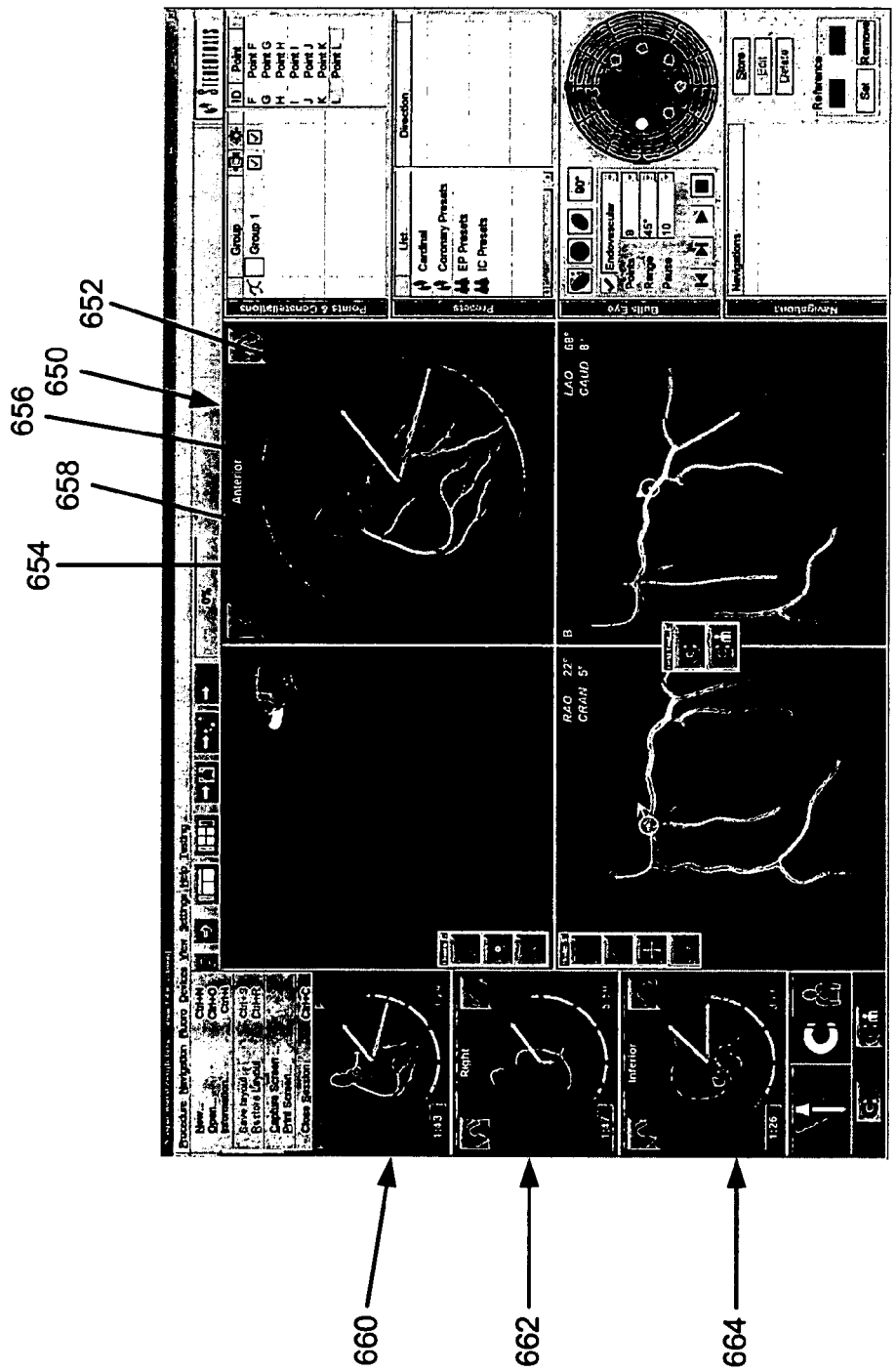
FIG. 29 is a view of a display of a third preferred embodiment of an interface in accordance with the principles of this invention, showing another control for specifying the direction of the magnetic field to be applied.
Figure 30A:
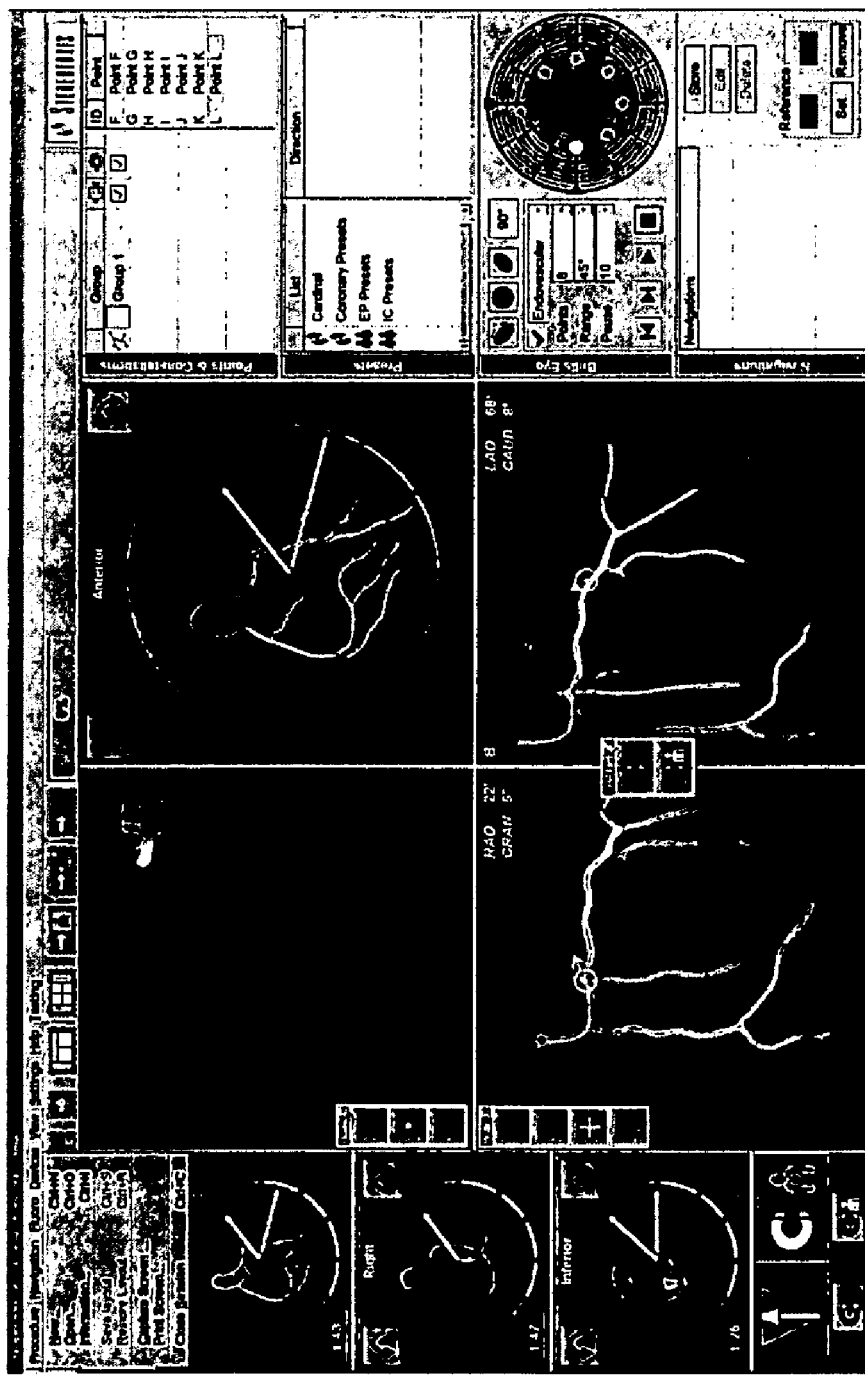
FIG. 30A is a view of a display of a third preferred embodiment of an interface in accordance with the principles of this invention, showing an orientation element.
Figure 30B:
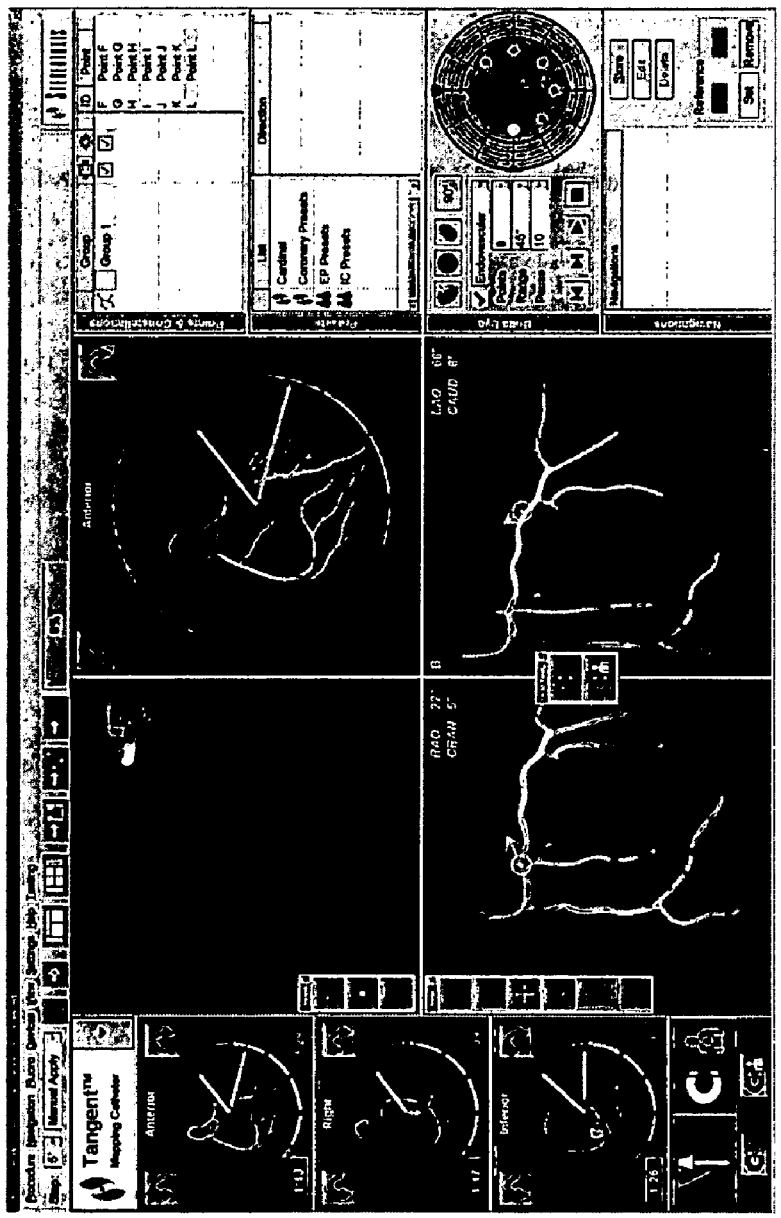
FIG. 30B is a view of a display of a third preferred embodiment of an interface in accordance with the principles of this invention, showing an orientation element.
Figure 30C:
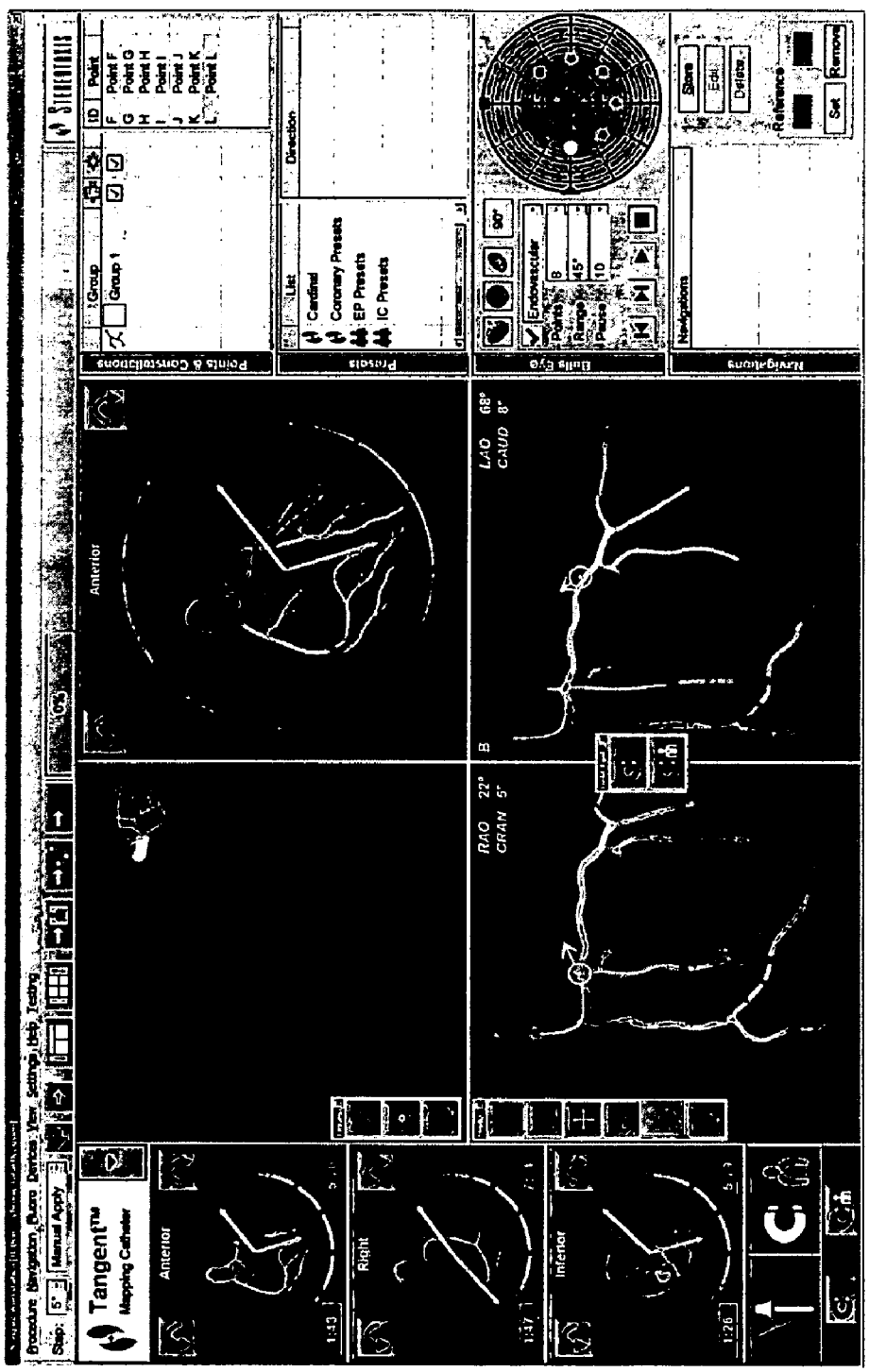
FIG. 30C is a view of a display of a third preferred embodiment of an interface in accordance with the principles of this invention, showing an orientation element.
Figure 31:
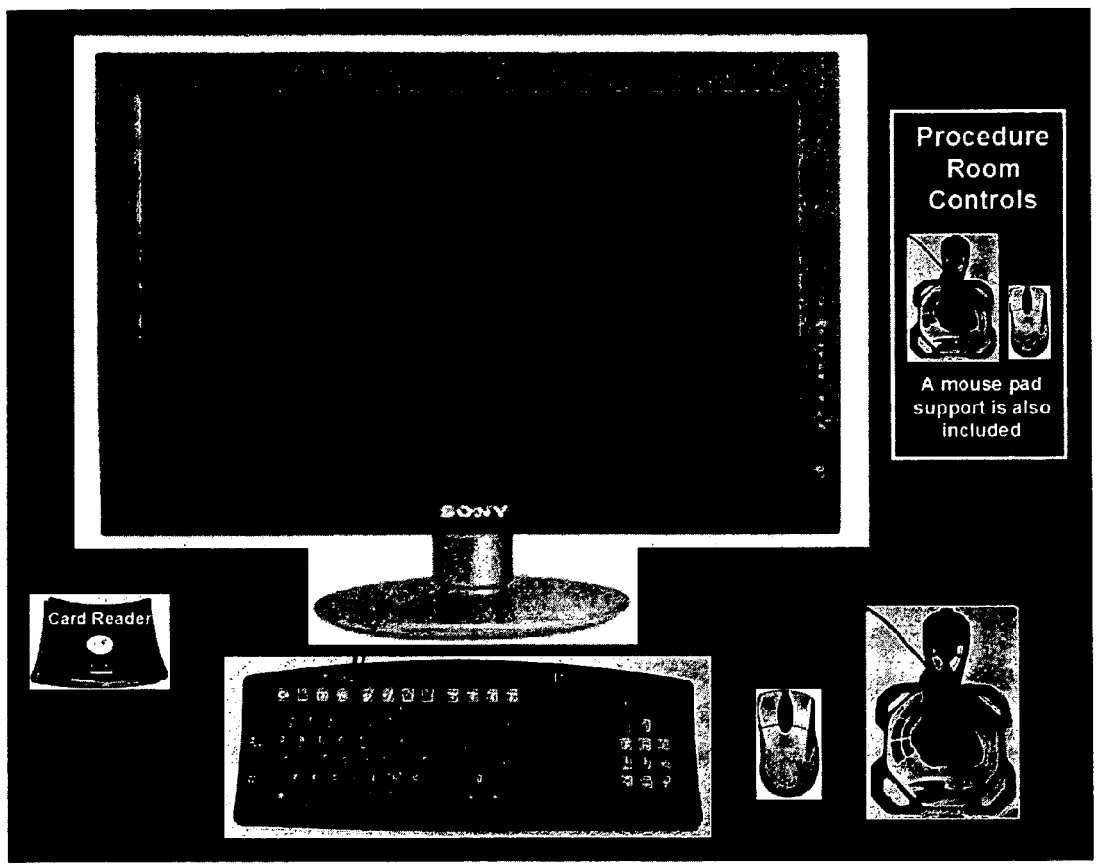
FIG. 31 is a schematic view of the hardware for operating the user interface used in a fourth preferred embodiment of this invention.

Another control of the interface of the third embodiment is illustrated in FIGS. 28 and 29. The control operates a magnetic navigation system that applies a magnetic field in a selected direction to an operating region in a subject to magnetically orient a medical device in the operating region. The control facilitates the specification for the direction in which to orient the medical device/apply a magnetic field.

The control comprises a display pane 650 including an indicator 652 for indicating the desired direction of the medical device and/or applied magnet field on a display. This indicator may be an arrow or other element capable of indicating a three-dimensional direction on a two-dimensional display. The display pane 650 includes at least first and second active areas 654 and 656 for separately controlling the indicator 652. An input device for controls a cursor or other indicator on the display pane to click and drag within one of the two active areas, to change the orientation of the indicator 652. Clicking and dragging in the first active area 654 rotates the indicator 652 about an axis perpendicular to the plane of the display, and clicking and dragging in the second active area 656 flattens in the indicator into the plane of the display, and rotates it about an axis perpendicular to the plane of the display. The input device is preferably a mouse, but could also be a joystick, space ball, touch screen or other device.

The indicator 652 is preferably surrounded by a closed shape, and wherein the first active area 654 outside the closed shape, and wherein the second active area 656 is inside the closed shape. In the preferred embodiment the closed shape is a circle 658 which bounds the maximum extension of the indicator 652. The circle preferably has a plurality of indicia around its circumference, and preferably twelve equally spaced indicia oriented like a clock face, for convenient reference by the users.

In a preferred implementation, there are preferably multiple panes showing the orientation of the indicator 652 from different perspectives. As shown in FIGS. 28 and 29, panes 660, 662, and 664 can be provided to provide an image of the indicator from three mutually perpendicular perspectives. Each of the panes allows for rotation of the indicator about an axis perpendicular to its particular plane. This, as described above, allows the user to adjust the orientation of the indicator 652.

The indicator 652 in pane 660 is surrounded by a circular frame 666, defining a first active area 668 outside the frame, and a second active area 670 inside the frame. Clicking and dragging in first active area 668 causes the indicator to rotate about an axis perpendicular to the plane of pane 652, while clicking and dragging in second active area 670 causes the indicator to drop into the plane of the pane 660, and rotate in that plane about an axis perpendicular to the plane of the pane 660.

The indicator 652 in pane 662 is surrounded by a circular frame 672, defining a first active area 674 outside the frame, and a second active area 676 inside the frame. Clicking and dragging in first active area 674 causes the indicator to rotate about an axis perpendicular to the plane of pane 652, while clicking and dragging in second active area 676 causes the indicator to drop into the plane of the pane 662, and rotate in that plane about an axis perpendicular to the plane of the pane 662.

The indicator 652 in pane 664 is surrounded by a circular frame 678, defining a first active area 680 outside the frame, and a second active area 682 inside the frame. Clicking and dragging in first active area 680 causes the indicator to rotate about an axis perpendicular to the plane of pane 664, while clicking and dragging in second active area 680 causes the indicator to drop into the plane of the pane 664, and rotate in that plane about an axis perpendicular to the plane of the pane 664.

In operation the interface is used to control a magnetic navigation system to apply a magnetic field in a selected direction in an operating region in a subject to magnetically orient a medical device in the operating region. The user selects the direction in which to apply a magnetic field by clicking and dragging on one of first and second active areas of a display to rotate an indicator indicating the desired direction. Clicking and dragging on the first active area rotating the indicator about an axis perpendicular to the plane of the display, and clicking and dragging on the second active area collapsing the indicator into the plane of the display, and rotating it about an axis perpendicular to the plane of the display. The user then operates the interface to cause the interface to apply a magnetic field to the operating region in the direction indicated by the indicator.

As shown in FIG. 3 this last control mode of navigation can be applied to specifying the field on the other panes. In this plane mode, a clock like circle is superposed over the indicator of the desired new direction. The indicator can be moved about an axis perpendicular to the clock face by clicking and dragging outside the clock face, or it can be moved in the plane of the clock face, also about an axis perpendicular to the clock face, by clicking and dragging inside the clock face.

A fourth embodiment of an interface in accordance with the principles of this invention is illustrated in FIGS. 32-48.

Figure 32:
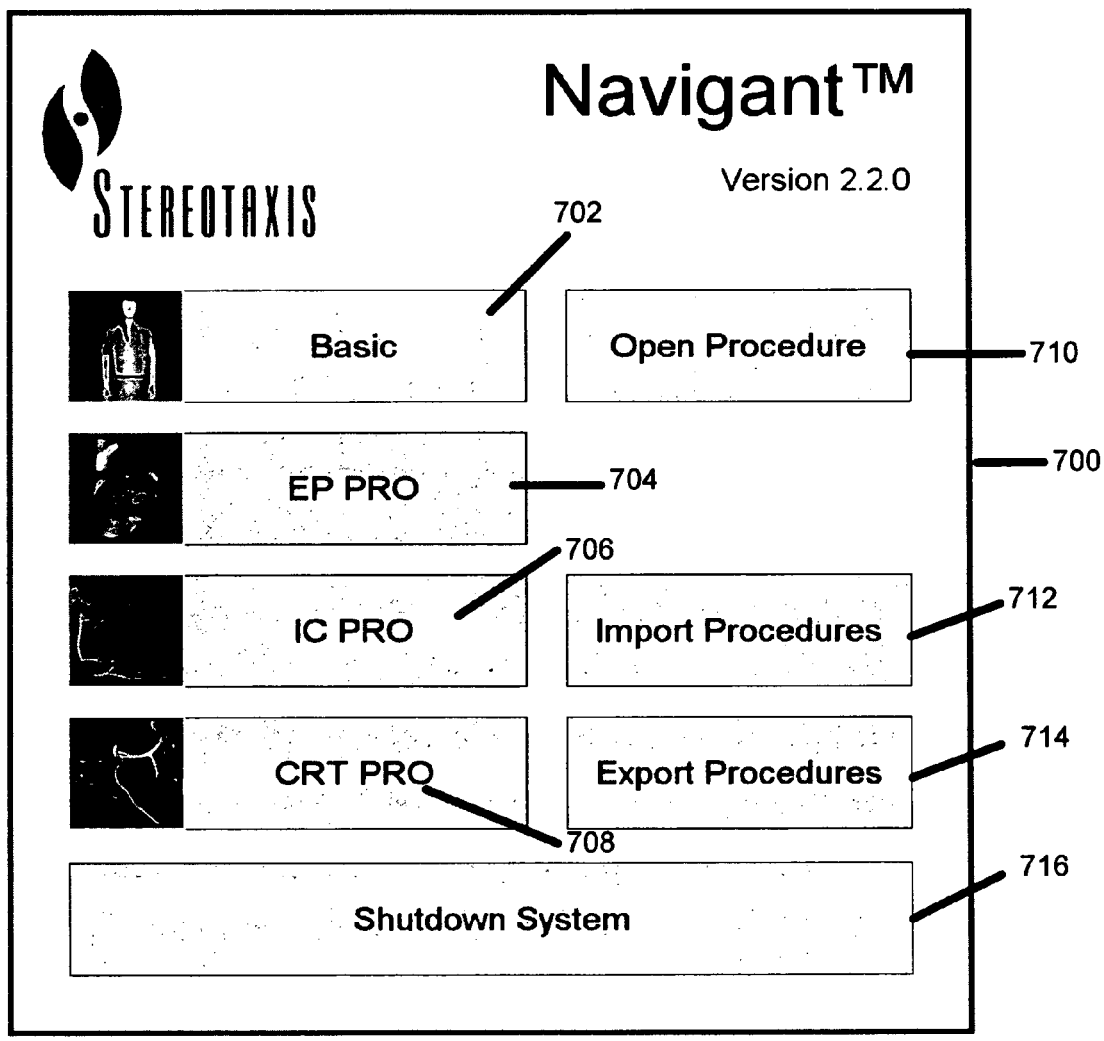
FIG. 32 is view of the main menu control screen of the fourth preferred embodiment of a user interface in accordance with the principles of the present invention.

One possible embodiment of a main menu for display on the monitors 72 and 80 is indicated generally as 700 in FIG. 32. The menu 700 has virtual buttons which the user can select and click using either the mouse 74 or 84, or using the joystick 76 or 86. In this preferred embodiment there are buttons 702 for operating the interface in the basic mode, button 704 for using the interface in an EP procedure; button 106 for using the interface in and IC procedure, and a button 708 for using the interface during a CRT procedure. The menu preferably also has buttons 710 for opening a previous procedure, a button 112 for importing a previous procedure, and a button 714 for exporting a previous procedure, and a button 716 for shutting down the system.

Figure 33:
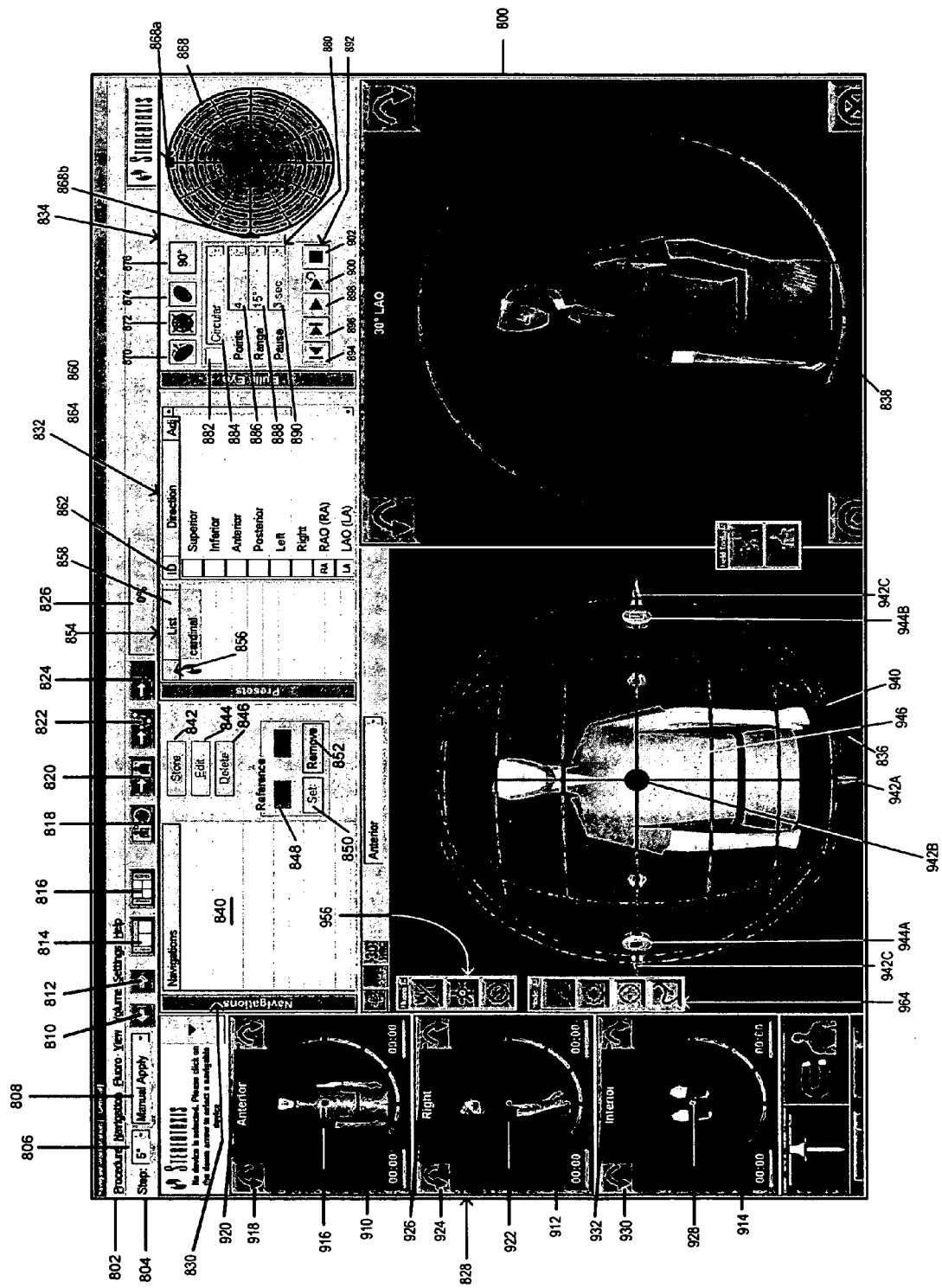
FIG. 33 is a view of a display from the basic mode of the fourth preferred embodiment of a user interface.
Figure 34A:
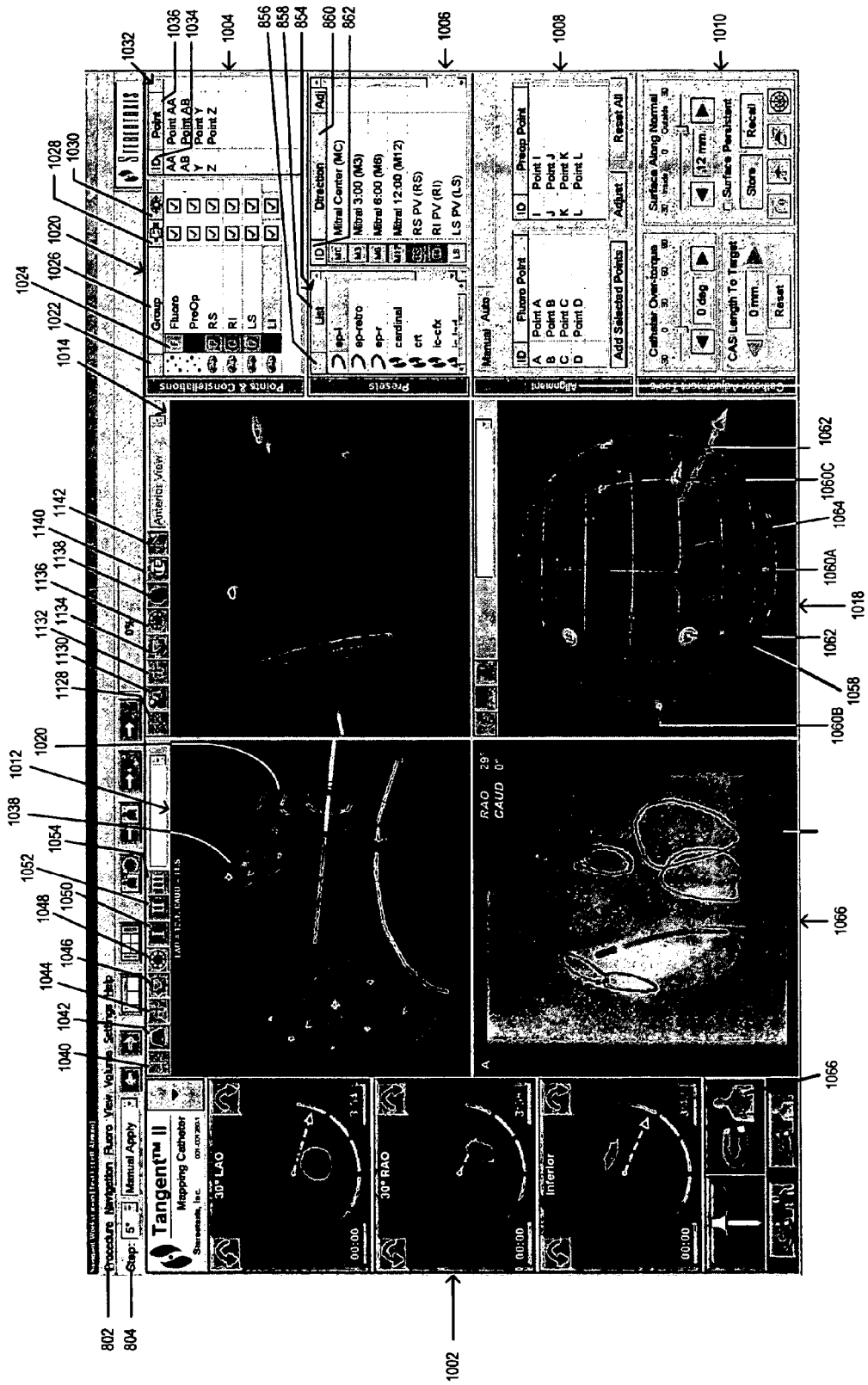
FIG. 34A is a view of a display from the EP mode of the fourth preferred embodiment of a user interface, in the right atrium mode.

To enter the basic navigation mode of the interface, a user points the cursor at the "basic" button 702, and clicking with the mouse or joystick. This action causes the basic navigation display, indicated generally as 800 in FIG. 33, to be displayed on the monitors. As shown in FIG. 33, the display 800 preferably includes a menu bar 802, which is preferably common to all screens, and which in this preferred embodiment has categories "Procedure", "Navigation", "Fluro", "View", "Volume", "Settings", and "Help". The display 800 preferably also includes a menu bar 804, which is preferably common to all screens, and which in this preferred embodiment has a step selector box 806, for selecting the increment size for changes in the direction of the applied magnetic field, and a magnetic navigation selector box 808, for selecting between a "Manual Apply" mode in which the magnetic field must be manually applied after the magnetic field direction is selected, and an "Automatic" mode in which a magnetic field is automatically applied in the selected direction without further action by the user. There are also format selection buttons 814 and 816, for selecting the format of the display. In this preferred embodiment there are two formats, the first, selectable with button 814 has two display panes surrounded by control panes at the left side and the top (for example as shown in FIG. 33), and the second, selectable with button 816, has four display panes surrounded by control panes at the left and right sides (for example as shown in FIG. 34A). The user can select the type of display pane or control pane to display by right clicking in a particular area to display a menu, and selecting the particular type of display pane desired.

An x-ray button 818 can be operated to drop down a menu to select an x-ray image to display in an active x-ray image pane on the display. An x-ray transfer button 820 can be operated to transfer new x-ray images from an x-ray imaging system to the interface, so that the new image can be selected when x-ray button 818 is operated.

A store point button 822 can be operated to store the current location of the distal end of the medical device being navigated with the user interface, using the Points & Constellation Pane as described below. Similarly a store vector button 824 can be operated to store the current direction of the device (or in this preferred embodiment the current magnetic field direction applied to the device by the magnetic navigation system. There is a vector window 826 for displaying the status of the applied magnetic field. As a newly selected magnetic field is applied, an indicator in the window 826 increases from 0% to 100% until the selected field is applied.

The display 800 also includes various user-selected panes for displaying the current orientation of the medical device and for specifying a new desired location or orientation of the medical device. As shown in FIG. 33, these panes can include a 2D field specification pane 828, a navigations pane 830, a presets pane 832, and a bulls eye pane 834. As described above, each of these panes can be replaced by right clicking on the pane to display a list of available alternative panes which can be selected. In this preferred embodiment, these panes can include a bull's eye pane, a points & constellations pane, a catheter adjustment pane, an alignment pane, and 2-D anatomical navigation pane. Of course the display 800 could include additional panes or fewer panes or different panes, including the various panes disclosed in the various other embodiments of this invention.

As also shown in FIG. 33, these panes also include two large panes, which can be an object navigation pane 836 and a field specification pane 838, which displays one of the subpanes of the 2-D field specification pane 828. As described above, each of these panes can be replaced by right clicking on the pane to display a list of available alternative panes which can be selected. In this preferred embodiment, these panes can include an object navigation pane, a 3D sync pane, a preoperative image pane, and an x-ray pane. Of course the display 800 could include additional panes or fewer panes or different panes, including the various panes disclosed in the various other embodiments of this invention.

The "Navigations" pane 830 includes a list 840 for entering a name or description of a stored direction; a store button 842 for storing the current direction (similar to button 824, described above); an edit button 844 for editing the name or description of a previously stored navigation; a delete button 846 for deleting a previously stored navigation; and a reference box 848 with a set button 850 and a remove button 852 for setting the color and id for a stored direction.

The "Presets" pane 832 allows the user to quickly select directions from one or more sets of standard directions. The "Presets" pane 832 has a list subpane 854, with an icon column 856, a list column 858 for the name of one or more sets of standard or preset directions. The "Presets" pane 832 also includes a directions subpane 860, which displays the directions that are part of a selected set on the list 858. The directions subpane 860 includes an ID column 862 and a description column 864. The ID column 862 contains a reference and a color code for each direction in the set, and the description column 864 contains a name or description of each direction in the set.

The Bull's Eye pane 834 comprises a generally circular display screen 868, and a plurality of buttons, including a set center button 870, a show/hide button 872, switch orientation button 874, and scale menu 876. In the preferred embodiment, the set center button 870 centers the bull's eye grid on the current magnetic field direction, so that it is concentric with the indicator of the current magnetic field direction. In other embodiments of the user interface for use with other navigation systems, this button could center the bull's eye screen on the current direction of the medical device instead of the current magnetic field direction. The show/hide button 872 toggles between a show mode in which the bulls eye grid is shown in the display panes in the interface, and a hide mode in which the bulls eye display is not shown in the display panes.

The switch orientation button 874 changes the orientation of the bull's eye grid between the standard proximal to distal view and a distal to proximal view 876. The display screen 868 preferably has indicators for indicating the orientation of the display screen and the corresponding bull's eye grid. For example, as shown in FIG. 33, an indicator 868a, which may be color coded (e.g. blue) is shown at the top of the circular display screen 868, and a corresponding indicator is shown on the bulls eye grid in the display panes, in the superior (up direction). A second indicator 868b, which also may be color coded (e.g. red) is shown at the left side of the circular display screen 868, and a corresponding indicator is shown on the bull's eye grid in the display panes. The indicators 868a and 868b help the user to understand the relationship between the display screen 868 and the bull's eye grid in the user interface. The switch orientation button 868 allows the user to switch the direction of the direction of the display screen 868 and the corresponding bull's eye grid in the display panes, from a perspective looking toward the distal end of the device, and the thus the indicator 868b is on the left side of the display screen 868 and the corresponding bull's eye grid, and a perspective looking toward the proximal end of the device, and thus the indicator 868b is on the right side of the display screen, and the corresponding bull's eye grid, reflecting the fact that the left side looking distally is the right side looking proximally.

The scale orientation menu 876 allows the user to set the scale of the display 838 and the bull's eye grid. In this preferred embodiment, the user can right click on the menu 876, and select from one of several preset scales, preferably including 15°, 30°, 45°, 60° and 90°. The Bull's eye navigation pane can otherwise be used like the bull's eye navigation pane 610 shown in FIG. 27, and described above. Thus, the Bull's Eye pane 834 preferably also includes a pattern navigation box 880 for selecting a pattern of points and for manually or automatically navigating to the points in the selected pattern. This pattern navigation box 880 includes a box 882 for activating pattern navigation, a selection box 884 for selecting the shape of the pattern, a points selection box 886 for selecting the number of points in the pattern, a range selection box 888 for selecting the angular range of the pattern from the center point; and a pause selection box 890 for selecting the duration of the pause between each navigation to a point in the automated pattern navigation mode. A control bar 892 has a first button 894 for returning to the first point in the pattern, a last button 896 for moving to the last point in the pattern, an advance button 898 for advancing to the next point in the pattern, and a autoadvance button 900 for automatically advancing through successive points, and a stop button 902 for stopping the automatic advancement.

The interface preferably displays a visual indicator of the desired orientation for the distal end of the medical device, such as the arrow 150, whose shaft is aligned with the desired orientation, with a large conical head pointing in the desired direction. The arrow 150 is preferably a distinctive color such as green. The interface preferably also displays a visual indicator of the current orientation of the distal end of the medical device, such as arrow 152, whose shaft is aligned with the current orientation of the distal end of the medical device, with a larger conical head pointing in the desired direction. The arrow 152 is preferably a distinctive color such as yellow.

A localization system can be provided for determining the current position and orientation of the distal end of the medical device. An image representative of the distal end of the medical device can then be generated and displayed. There are numerous method for localizing the distal end of the medical device, for example transmitting magnetic or rf signals between the medical device and one or more reference locations, x-ray image processing, ultrasound localization, or electric potential localization.

In this preferred embodiment, the interface is adapted for use with a magnetic navigation system that operates by generating a magnetic field of selected direction in the operating region, which causes a magnetically responsive element associated with the distal end of the medical device to generally align with the applied magnetic field. Because of the physical properties of the medical device, limitations in the strength of the applied field, and the conditions in the procedure site, the distal end of the medical device may not align precisely with the applied magnetic field. While the difference between the applied magnetic field and the actual direction of the distal end of the medical device can be accounted for through modeling or a look-up table, in this preferred embodiment the arrow 150 representing the desired orientation may represent the desired direction of the applied magnetic field, rather than the desired direction of the medical device itself. Similarly, the arrow 152 representing the current orientation may represent the direction of the magnetic field currently being applied, rather than the actual direction of the device itself. However, the differences between the actual direction of the medical device and the applied magnetic field can be characterized by equation or an empirically determined look-up table, or localization of the device can be provided so that even when used with a magnetic navigation system, the arrow 150 represents the actual desired orientation of the medical device, and arrow 152 represents the actual current direction.

Other panes facilitate the visualization and selection of directions. One such pane to aid the user in selecting the desired orientation for the medical device is the 2-D anatomical pane 828, which allows the user to select the desired direction (as indicated by the arrow 150) by adjusting the direction of the arrow 150 in one or more planes through the operating region in the subject. As shown in FIG. 33, the pane 828 allows the user to change the direction of the arrow 150 in at least one plane, and preferably at least two planes and more preferably at least the planes. These planes are preferably, but not necessarily, mutually perpendicular. While adjustment in two planes is sufficient to specify any direction, providing adjustment in three planes makes it easier for a user to select the desired direction for the arrow 150. In this fourth preferred embodiment, the arrow 150 can be rotated in the coronal or frontal plane (i.e., about an anterior-posterior axis), the median or saggital plane (i.e., about a horizontal axis), and the horizontal or transverse plane (i.e., about a longitudinal axis).

As shown in FIG. 33 the pane 828 can have three subpanes 910, 912 and 914, corresponding to the three planes of rotation. Subpane 910 contains a graphic depiction of the coronal or frontal plane (i.e., a caricature image of a subject's body in the coronal or frontal plane), with an indicator 916 that indicates the orientation of the arrow in the coronal or frontal plane, and virtual buttons 918 and 920 for moving the indicator 916 (and thus the arrow 150) clockwise or counterclockwise in the coronal or frontal plane abut the anterior-posterior axis. In this fourth preferred embodiment, indicator 916 is actually a projection of the arrow 150 in the plane, and thus the length of the indicator 916 is indicative of the orientation. The virtual buttons 918 and 920 can be operated with a cursor for example with the mouse 74 or 82 or the keyboard 80, to point and click the button and move the indicator 916 and thus the arrow 150, in the desired direction.

Subpane 912 contains a graphic depiction of the median or saggital plane (i.e., a caricature image of a subject's body in the median or saggital plane), with an indicator 922 indicating the direction of the arrow 150 in the median or saggital plane, and virtual buttons 924 and 926 for moving the indicator 922 (and thus the arrow 150) clockwise or counterclockwise in the coronal or frontal plane. In this first preferred embodiment, indicator 922 is actually a projection of the arrow 150 in the plane, and thus the length of the indicator 922 is indicative of the orientation. The virtual buttons 924 and 926 can be operated with a cursor for example with the mouse 74 or 82 or the keyboard 80, to point and click and move the indicator 922 and thus the arrow 150, in the desired direction.

The pane 914 contains a graphic depiction of the horizontal or transverse plane (i.e., a caricature image of a subject's body in the horizontal or transverse plane), with an indicator 928 indicating the direction of the arrow in the horizontal or transverse plane, and virtual buttons 930 and 932 for moving the indicator 178 (and thus the arrow 150) clockwise or counterclockwise in the horizontal or transverse plane. The virtual buttons 930 and 932 can be operated with a cursor for example with the mouse 58 or 66 or the keyboard 64, to point and click to move the indicator 928, and thus the arrow 150 in the desired direction.

As described above, the menu bar 804 contains a step selector box 806 to select the increment of change in direction upon operating the buttons 918 and 920, 924 and 926, and 930 and 932. The user can preferably select the incremental change from several preset increments: 1 degree, 2 degrees, 3 degrees, 5 degrees, 10 degrees with a cursor for example with the mouse 74 or 82 or the keyboard 80, to point and click to select the desired increment.

The object navigation pane 836 has a representation 940 of a three-dimensional object. This three dimensional object is preferably a sphere, but it could be some other shape such as an ellipse or a cube. There are preferably indicators on the surface of the three dimensional object to indicate the corresponding directions in the operating region in the subject. In this preferred embodiment, these indicators include cones 942 for identifying the directions of major anatomical axes in the subject. As shown in FIG. 33, there are a pair of cones 942A identifying the superior-inferior axis, a pair of cones 942B identifying the anterior-posterior axis, and a pair of cones 942C identifying the left-lateral right-lateral axis. Each of the pairs of cones 942A, 942B, and 942C, are preferably displayed in a unique color. There are preferably a plurality of latitude lines and longitude lines on the surface of the three-dimensional object. In this preferred embodiment, the latitude lines and longitude lines for each axis are color coordinated with the color of the cones, and preferably can be selectively displayed or hidden.

The indicators can also include direction indicators 944 for identifying other selected directions in the operating region in the subject on the surface of the three dimensional object. As shown in FIG. 33, these indicators 944 can include an indicator 944A indicating the RAO direction and an indicator 944B indicating the LAO direction. The cone pairs 942A, 942B, and 942C, and the indicators 944A and 944B, indicate the preset cardinal directions as set forth on the Presets pane 832.

The indicators can also include a representation of at least a portion of the subject, such as representation 946. This representation can be an idealized representation of a subject. Alternatively, this representation could be created from actual image data of the subject. Of course the representation could also be a representation of an internal body structure. This representation could either be an idealized representation of the internal body structure, or it could be a representation created with imaging data from the subject. Each point on the surface of the representation 940 of the object corresponds to a direction in the operating region. The user clicks on a location on the surface of the representation 940 of the object to identify the desired direction of orientation in the operating region. The indicators 942 and 944, and the representation 946 help the user identify the point on the surface of the representation of the object 940 that corresponds to the desired direction.

The object navigation pane 836 has a rotation button 948, a spherical/hemispherical button 950, a 3D sync button 952, and a view selection window 954. The rotation button 948 toggles between a rotation mode in which the cursor can be manipulated by a control device such as mouse, joystick, or keyboard to grab and rotate the representation 940 of the object, and a selection mode in which the cursor can be manipulated by a control device such as a mouse, joystick, or keyboard, to select a point of the surface of the representation 940 of the object.

The spherical/hemispherical button 950 toggles between an external view of the representation 940 of the object, and an internal view of the representation of the object, which is preferably taken from a vertical plane through the center of rotation of the object.

The 3D sync button 952 preferably synchronizes rotation of a 3D representation of the operating region with the rotation of the representation 940 of the object in the object navigation pane 838.

A floating "Fluro" tool bar 956 can be made to appear on the interface display, and has a contrast/brightness button 958, a pan button 960, and a vector show/hide button 962. The contrast/brightness button 958 displays a menus allowing the user to adjust the contrast and the brightness of the fluoro display pane (which is not shown if FIG. 33). The pan button 960 allows the user to pan over the x-ray image displayed in the fluoro display pane. The vector show/hide button 962 can be operated by the user to selectively show or hide the direction vectors, e.g. the current direction vector 150 and the desired new direction vector 152.

A floating "Mode" window 964 can also be made to appear on the interface display, and has a vector mode button 966, an x-ray mode button 968, a target mode button 968, an a vessel navigation mode button 972. The vector mode button 966 causes the active display panes to enter the vector mode in which the directions are displayed and specified on the panes. The x-ray mode button 968 permits field adjustments to be made in the plane of the selected reference X-ray window. The target mode button 968 causes the active display panes to enter the target mode, where target points are identified rather than navigation directions. The vessel navigation button can be used to set the local tangent at a location along a vessel constellation (defined by an automatic spline curve fitting to a group of fluoro-localized points along a vessel) by double-clicking at that location on the vessel constellation in the 3D window.

A display from the EP mode of the fourth preferred embodiment of a user interface is indicated as 1000 in FIG. 34. The display is reached by clicking on button 704 on the menu 700. The display 1000 comprises a 2D field specification pane 1002, similar to pane 828 described above. The display 1000 also comprises a "Points & Constellation" pane 1004, a "Presets" pane 1006 similar to "Presets" pane 832 described above, an "Alignment" pane 1008, and a "Catheter Adjustment Tools" pane 1110. The display 1000 also includes a 3-D view pane 1012, an anatomical model pane 1014, an x-ray display pane 1016, and an object navigation pane 1018 similar to the object navigation pane 836.

Using the various navigation tools of the interface, the user can navigate the distal end of a medical device to selected points in the operating region, and assemble these points in groups or constellations. The user can use the "Points & Constellations" pane 1004 to select how these points are displayed in the various panes of the user interface. As shown in FIG. 34, the "Points & Constellations" pane 1004 has a subpane 1020 with a column 1022 for selecting how the point or constellation is displayed on the panels of the display 1000; a column 1024 for indicating a color code for displaying the point or group of points, and a code for indicating from which panes the points were created, a column 1026 for displaying a name of the point or group of points; a column 1028 for selecting whether to display the point or group of points on an x-ray display pane 1016, and a column 1030 for selecting whether to display the point or group of points on the 3D display 1012. When a particular point or group of points on the subpane 1020 is selected, the member points are displayed in subpane 1032, which has a column 1034 for an ID of the point and a column 1036 for a name of the point.

The column 1022 allows the user to select how the points in a group are displayed in the 3-D pane 1012. The user can select (for example by right clicking with the mouse or some similar command) to display the points as a group. The user can also select to display a group of points as a computer generated spline (a closed loop that best fits the point or points selected. (See FIG. 35). The user can also select to display a group of points as a computer generated planar disk, such as disks 1038 in pane 1012, which are particularly well suited for displaying ostium or openings in a surface that have been identified by a plurality of points. The interface generates a closed loop of active points 1036 from a set of selected points, and generates a disk of active points surrounding the loop in the same general plane. (See FIG. 36). The user can easily select a point on the loop 1036 or on the disk 1038, and the interface allows the user to make the medical device to point toward the selected point. The user can also select to display the points as a surface patch 1039, comprising a surface between the points in the group. (See FIG. 37).

Figure 34B:
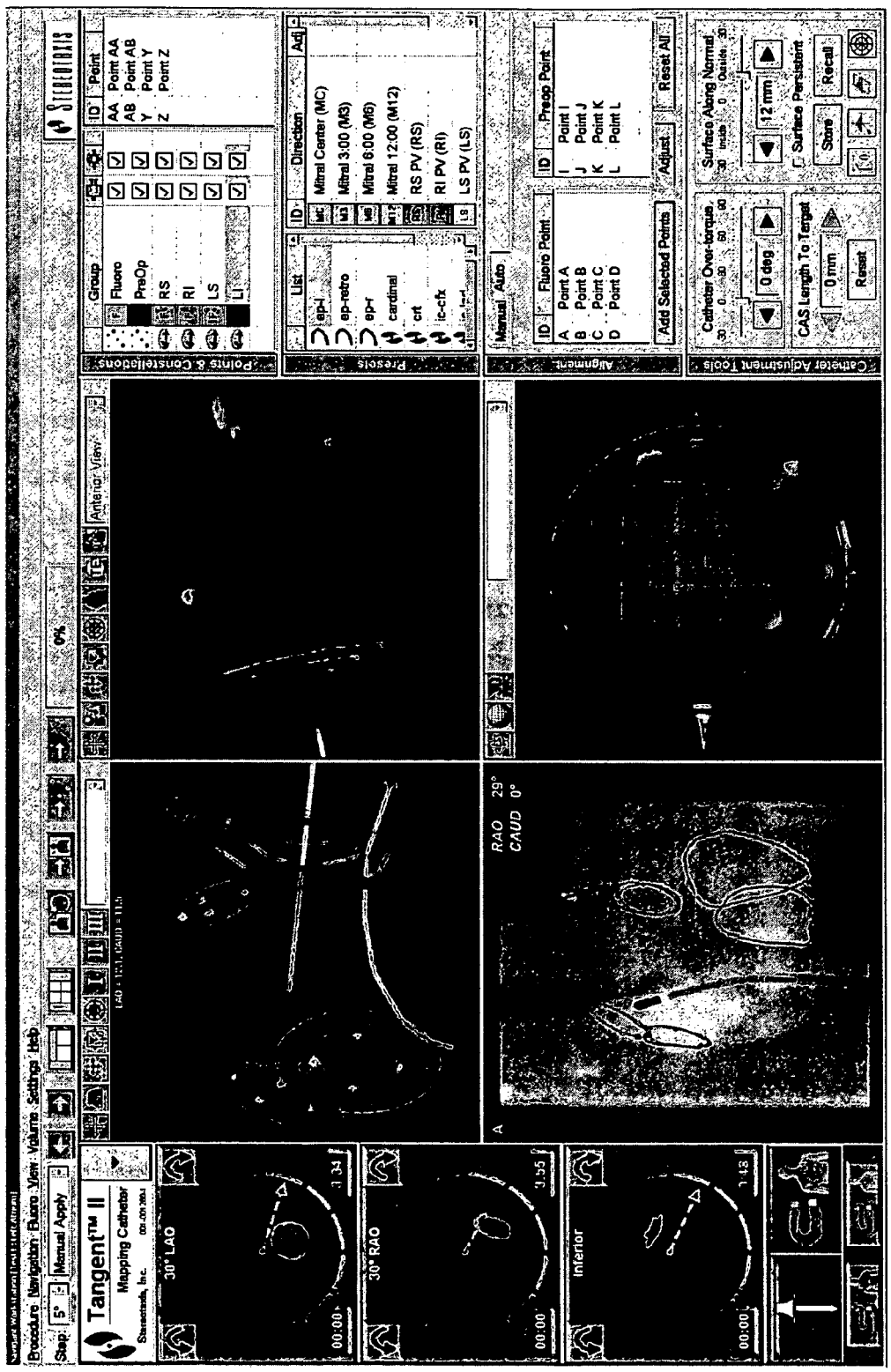
FIG. 34B is a view of an alternative to the display of FIG. 34A.
Figure 35:
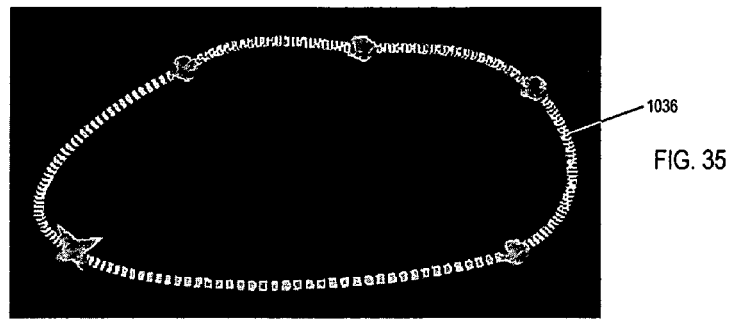
FIG. 35 is a view of a closed spline indicator used in the spherical object navigation mode of the preferred embodiment of the present invention.
Figure 36:
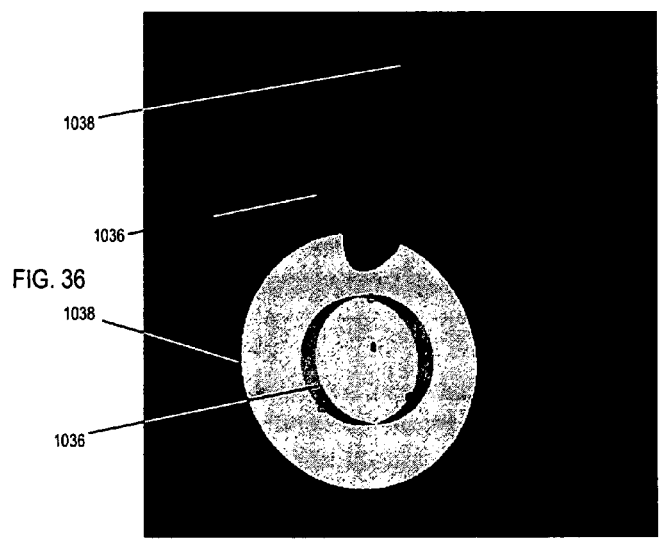
FIG. 36 is a view of an ostium indicator used in the spherical object navigation mode of the preferred embodiment of the present invention.
Figure 37:
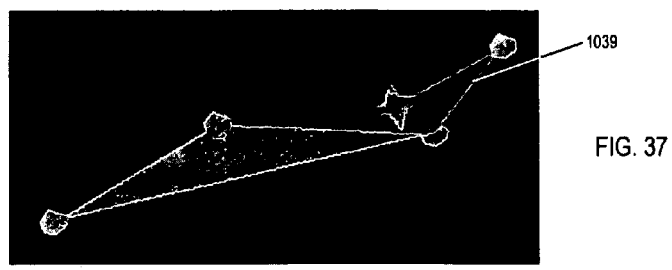
FIG. 37 is a view of a surface constellation indicator used in the spherical navigation mode of the preferred embodiment of the present invention

The user can also cause the points to be displayed in the x-ray image pane 1016, by checking the appropriate box in column 1028 of the subpane 1032 As shown in FIGS. 34A and 34B, the groups are indicated as splines superposed over the x-ray image in the pane 1016, in the color indicated in column 1024 for the group to which each point belongs.

The pane 1012 has a pan button 1040, a 3D grid show/hide button 1042, a point selection button 1044, a direction selection button 1046, a bulls eye button 1048, a first user defined view_button 1050, a second user defined view button 1052, a third user defined view button 1054, and a view selection window 1056. The pan button 1040 allows the user to select a mode in which the movement of the cursor, for example with the mouse, joystick, or keyboard, allows the user to pan across the view in the pane 1012. The point selection button 1044 allows the user to select a point in the pane 1012. The direction selection button 1046 allows the user to select a direction in the pane 1012. The bulls eye button 1048 causes the bull's eye grid to be displayed on the pane 1012. The first, second, and third user defined view buttons 1050, 1052, and 1054 allows the user to save up to three separate user defined views, so that the user can quickly and easily return to those views. The view selection window 1056 allows the user to select one of several standard views in the pane 1012.

The object navigation pane 1018 is similar to the object navigation pane 836 on display 800, and includes a representation 1058 of a three dimensional object. As described above with respect to object 940, the three dimensional object depicted by representation 1058 is preferably a sphere, but it could be some other shape such as an ellipse or a cube. There are preferably indicators on the surface of the representation 1058 of the three dimensional object to indicate the corresponding directions in the operating region in the subject. In this preferred embodiment, these indicators include cones 1060 for identifying the directions of major anatomical axes in the subject. As shown in FIGS. 34A and 34B, there are a pair of cones 1060A identifying the superior-inferior axis, a pair of cones 1060B identifying the anterior-posterior axis, and a pair of cones 1060C identifying the left-lateral right-lateral axis. Each of the pairs of cones 1060A, 1060B, and 1060C, are preferably displayed in a unique color. There are preferably a plurality of latitude lines and longitude lines on the surface of the three-dimensional shape. In this preferred embodiment, the latitude lines and longitude lines for each axis are color coordinated with the color of the cones, and preferably can be selectively displayed or hidden.

The indicators can also include direction indicators 1062 for identifying other selected directions in the operating region in the subject on the surface of the three dimensional object. As shown in FIGS. 34A and 34B, these indicators 1062 can include an indicators for the various preset directions for the selected set of directions in "Presets" pane 1006. The "Presets" pane 1006 is similar to the "Presets" pane 832 described above. The cone pairs 1060A, 1060B, and 1060C, and the indicators 1062 help the user select the appropriate point on the surface of the representation 1058 of the object to properly identify the desired corresponding direction in the operating region in the subject.

The indicators can also include a representation of at least a portion of the subject, such as representation 1064. This representation 1064 can be an idealized representation of the internal body structures in the operating region in the subject. Alternatively, this representation 1064 could be created from actual image data of the operating region in the subject. Of course the representation could also be a representation of an external body structure, as described above with respect to pane 836 of display 800.

The object navigation pane 1018 is particularly adapted for direction based navigation, rather than point based navigation, although it could be used in point based navigation. Each point on the surface of the representation 1058 of the object corresponds to a direction in the operating region. The user simply manipulates a cursor to the desired position and clicks on the location on the surface of the representation of the object to identify the desired direction in the operating region in the subject. The indicators 1060 and 1062, and the representation 1064 help the user identify the point on the surface of the representation 1058 of the object that corresponds to the desired direction.

Other directional markers are preferably provided on the surface of the object 1058. For example, the various system-specified and user-specified preset directions can be stored by the interface. The "Presets" pane 1006 is similar to Presets pane 832, and corresponding parts are identified with corresponding reference numerals. The "Presets" pane has a "List" subpane 854, and a "Directions" subpane 860. The list subpane 854 has a column 856 for icons indicating the type of set of directions, and a name column 858 for indicating the name of the direction. For a selected set of directions on the List subpane 854, the "Directions" subpane 860 displays the various directions that comprise the set. The "Directions" subpane 860 has an ID column 862 which displays an ID code and a color code for each direction, These directions are in turn displayed on the object 1058 using indicators 1062 with corresponding ID codes and colors. These indicators 1062 help the user select a point on the surface of the object 1058 that corresponds to the desired direction in the operating region, including picking one of the preset directions.

The interface is preferably provided with a variety of present directions that users can employ to orient the medical device. For example standard directions from the center of the operating region, or from a particular entrance of an operating region, to common procedure destinations for typical anatomies can be determined, and these directions stored, so that when a user desires to navigate to one of these common destinations, the user merely needs to select from among the standard directions. For example, as shown in FIGS. 34A and 34B, standardized directions to the center of the mitral center, the 3 o'clock position on the mitral valve, the six o'clock position on the mitral valve, and the 12 o'clock position are all indicated by markers on the object 1058. These marks are color coordinated with the ID column 862 in the "Directions" subpane 860, and each is identified with the code appearing in the ID column 862.

The user can select a direction by pointing a cursor and clicking on the surface at the point corresponding to the desired direction. In this preferred embodiment which includes a magnetic navigation system, the magnetic navigation system is then applied, for example by clicking on the apply magnetic field button 1066. Depending upon how the system is set up, the system may either apply a magnetic field in the selected direction, or it may apply a magnetic field that will cause the device to point in the desired direction. Alternatively, in the continuous mode, the magnetic navigation system can automatically act to orient the device in the desired direction. When used with non-magnetic navigation system, the selected direction can be input to the control of the non-magnetic navigation system, which can then orient the medical device in the desired direction.

The pane 1018 includes an orientation button 1068, a full-sphere/half-sphere button 1070, a 3D sync button 1072, and a window 1074. The orientation button 1068 causes the display to enter the pivot mode where the user can uses the controls (e.g. the cursor under the control of the mouse or joystick), to rotate the object 1058. The object 1058 preferably pivots about its center, but it could pivot about some other point, if desired. The full-sphere/half-sphere button 1070 toggles between a full-sphere view in which the entire object 1058 is visible (for example, FIG. 34A), and a half-sphere view in which the front half of the object 1058 is removed, and the rear half is visible from the inside (for example FIG. 34B). The 3D sync button 1072 synchronizes the object navigation pane 1018 with the 3D display pane 1012, so that rotation of the representation of the object 1058 rotates that 3d display pane 1012. The window 1074 allows the user to select among one of several standard views.

Figure 38:
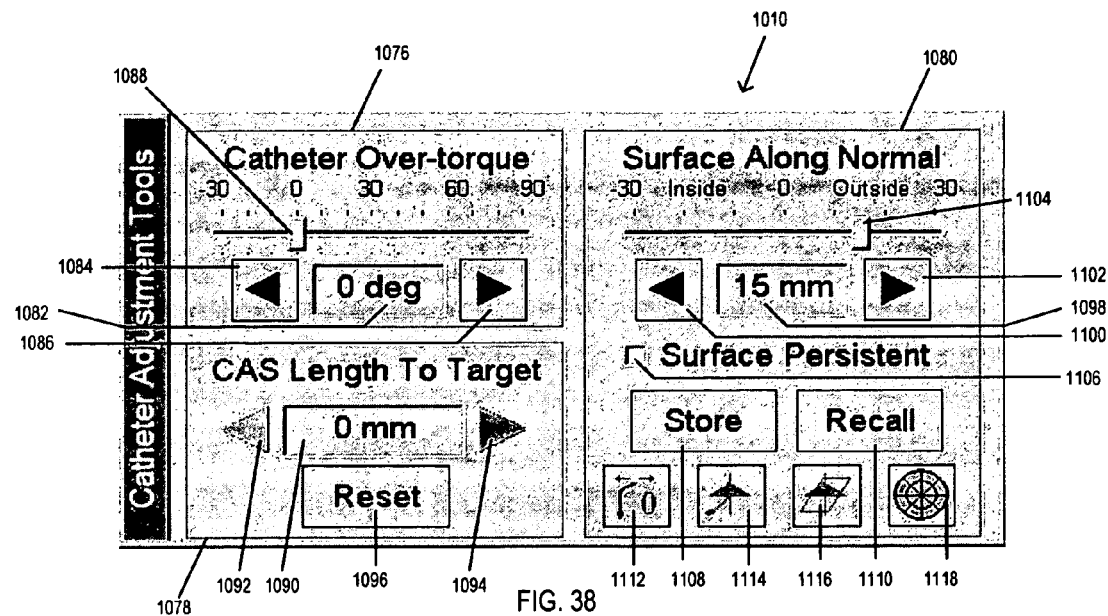
FIG. 38 is a view of a control pane for a catheter adjustment mode of the user interface of the preferred embodiment.
Figure 39:
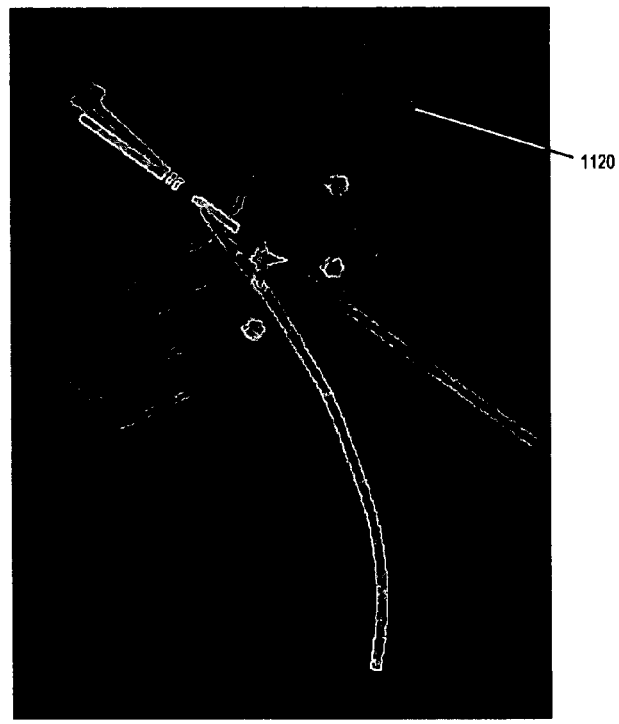
FIG. 39 is a view of a pane for a catheter adjustment mode of the user interface of the preferred embodiment.

The interface can also employ a Catheter Adjustment Tool pane 1010, which has an angle adjustment box 1076, and a position adjustment box 1078, and a position adjustment box 1080. As shown in FIG. 38, in the angle adjustment box 1076, the user can specify an angle of catheter over-torque, i.e., an angular adjustment beyond what is necessary to contact the surface, to increase the contact force between the catheter and an anatomical structure in the operating region. The box 1076 includes an indicator window 1082 for displaying the angle of over-torque, and increase and decrease buttons 1084 and 1086 for increasing and decreasing the angle of over-torque, and a slide control 1088 for alternatively specifying the angle of overtorque. A button 1112 can be provided to reset the over-torque to zero.

The position adjustment box 1080 includes controls for displaying and operating a distance adjustment tool. The box is used in conjunction with a display of a representation 1081 of the distal end of the medical to adjust the configuration of the representation of the distal end of a medical device to a desired configuration, and then cause the actual medical device to conform to the configuration of the representation of the medical device. The representation 1081 is preferably derived from a computational model of the actual medical device, as is discussed in U.S. patent application Ser. No. 10/448,273, filed May 29, 2003, for Remote Control of Medical Devices Using a Virtual Device Interface, U.S. Patent Application 20040068173 published Apr. 8, 2004, the entire disclosure of which is incorporated herein by reference.

The box 1080 includes a button 1118 for displaying a catheter adjustment indicator or reticle 1120 (shown in FIG. 39), in the 3D view pane (e.g., panes 1012 in FIGS. 34A and 34b). In this preferred embodiment the reticle 1120 comprises a series of concentric rings (hexagonal in this preferred embodiment) with a perpendicular line extending through its center point, although the active area of adjustment is really an umbrella-shaped surface that includes the displayed rings. The reticle 1120 is displayed at a point selected by the user. If the point selected by the user (for example by pointing a cursor and clicking) is not on a surface, the reticle 1120 is preferably displayed centered at the distal tip of the representation of the medical device, in an orientation perpendicular to the orientation of the distal end of the medical device. If the point selected by the user is on a surface, the center of the reticle 1120 is preferably positioned on a line normal to the surface point at a default distance from the surface selected by the user. This default distance may be zero to position the reticle 1120 at the surface, or it may be a positive distance to position the reticle 1120 beyond the surface, or a negative distance to position the reticle short of the surface. In this preferred embodiment, the user can also specify that the reticle be displayed in the plane of the display at the selected point by using button 1116.

The position of the reticle 1120 and thus the position of the representation of the distal end of the medical device, which follows the reticle, can be adjusted to achieve a desired position or configuration of the representation of the medical device. Once the desired position or configuration is achieve, the navigation system can be operated to cause the actual medical device to conform to the representation. Alternatively, the navigation system could automatically operate to cause the actual medical device to conform to the representation of the medical device as changes are made to the representation.

The box includes an indicator 1098 which indicates the distance between the reticle 1120 (and the distal end of the medical device being controlled with the interface), and the starting point. Where an offset from the surface is specified, this offset is automatically displayed in the indicator 1098. Further movement of the reticle 1120 is reflected in the indicator 1098. Buttons 1100 and 1102 allow the user to selectively increase or decrease the distance between the reticle 1120 and the representation of distal end of the medical device) and the starting point. The box 1080 can also include a slide control 1104 for selecting the distance (+ or −) of the reticle 1120 and the representation of the distal portion of the elongate medical device and the starting point, increasing and decreasing the distance between the reticle and the starting point, and thereby changing the configuration of the representation of the distal end of the medical device. This distance can be either negative indicating that the desired destination point is inside of the starting point, or the distance can be positive indicating that the desired destination point is outside starting point.

As shown in FIG. 38, the box 1080 can also include a surface persistent box 1106. When the user selects the surface persistent box 1106, the indicator 1120 remains at its current location even if the distal tip of the medical device moves. A store button 1108 stores the location of the indicator 1120, and the recall button 1110 recalls the location of the indicator 1120. This facilitates returning to a previously navigated location.

As shown in FIG. 38, the box 1078 can have a window 1090 indicating the change in length of the elongate medical device to reach the destination point represented by the reticle. The window indicates amount of the change, and increase and decrease indicators 1092 and 1094 indicate the direction of change (i.e. whether the length needs to be increased or decreased) to bring the distal end of the actual device to the point indicated by the representation of the distal end of the medical device on the reticle 1120. When the free length of the medical device needs to be increased to reach the position in the operating region corresponding to the position represented by the representation of the medical device on the reticle 1120, the increase indicator 1092 is activated, and when the free length of the medical device needs to be decreased to reach the position in the operating region corresponding to the position represented by the representation of the medical device on the reticle 1120 indicator, the decrease indicator 1094 is activated. The box 1078 also includes a reset button 1096 to reset the window 1090.

In operation the user navigates the distal end of the device to a point on the surface, and clicks on the show/hide button 1118. The reticle 1120 comprising a set of concentric rings is displayed centered at the selected point in the operating region. Alternatively, the user could operate button 1114 to display the indicator 1120 at the distal end of the medical device, perpendicular to the current orientation of the distal end of the device, or the user could operate button 1116 to display the indicator 1120 at the distal end of the medical device, in a plane perpendicular to the plane of this pane. A line 1122 normal to the surface at the selected current point is also displayed. The user adjusts the position of the reticle 1120 to identified the desired destination of the distal end of the medical device in the operating region. The representation of the medical device, which is preferably based upon a computational model, displays the predicted or theoretical configuration of the distal end portion of the medical device. The user adjusts the position of the reticle 1120 along the normal line 112 by operating the buttons 1100 and 1102, or operating the slide control 1104. The reticle also defines an active surface, and the user can also move the representation of the distal end of the medical device from the center of the recycle to some other point on the surface of the reticle by selecting the point on the surface of the reticle (for example by pointing with a cursor and clicking). The representation of the medical device updates to display the predicted or theoretical configuration of the medical device.

By adjusting the position of the reticle 1120 along the line 1122, and by adjusting the position of the representation of the medical device relative to the surface of the reticle, the user can accurately make minor adjustments in the position and configuration of the actual device. Once the desired configuration of the medical device is correctly indicated in the display, the user can then apply the configuration. In this preferred embodiment employing a magnetic navigation system, the user simply click the apply field button and the navigation system orients the actual device in the direction required to reach the target point indicated on the display. The user then advances or retracts the device as indicated on the indicators 1090-1094, to bring the medical device to the desired destination. With other navigation systems, the system could be operated to orient the distal end portion in the appropriate configuration, and the device advanced. In this manner the distal end of the device can be easily advanced into a lumen, or pressed against a wall of an anatomical structure.

It is possible that the movement of the distal end of the device could be automated as well as the orientation of the distal end. Feedback from a localization system could also be incorporated to facilitate the automation of the orientation and movement of the distal end of the device.

The display 1000 also includes an anatomical pane 1014, with a representation 1126 of a three-dimensional anatomical feature, obtained from imaging data from the subject. Each point on the surface of the representation corresponds to a location in the operating region. The anatomical pane 1014 has a pan button 1128, a show/hide objects button 1130, a center point button 1132, a fit-objects-to-window button 1134, a view synchronization button 1136, a transparency selection button 1138, a Tissue Editor button 1140, and a "Share Fluoro Points" button 1142. The pan button 1128 allows the user to use the cursor to click and drag the display in the pane, for example with the mouse, joystick, or keyboard to change the view. With a mouse click on this button, a toolbar of other choices for the mouse mode (such as rotation) can also be brought up to change the mouse mode if desired. The show/hide objects button 1130 allows the user to display objects such as the points selected on the surface of the representation 1126 of the three dimensional anatomical feature, within the anatomical window pane 1014. The center point button 1132 centers the display on the pane 1014 on a selected point. The fit-objects-to-window button 1134 rescales the display scale within the window so that all objects are visibly displayed in the pane 1014. The view synchronization button 1136 synchronizes the display perspective in the pane 1014 to that of the display selected with this button, for example that of the bull's eye display. The transparency selection button 1138 allows for a choice of opaque, semi-transparent or transparent display of the three dimensional image displayed in the pane 1014. The Tissue Editor button 1140 brings up a choice of colors, shades and transfer functions for the data that may be chosen by a user to display the three dimensional image data in customized form. The "Share Fluoro Points" button 1142 permits display of fluoro-localized points in the pane 1014 after a suitable registration between preoperative image data and the X-ray or navigation system has been effected, in a manner similar to that described herein.

The pane 1014 also includes a window 1144. The window 1144 allows the user to selected one of several standard views.

Once the three dimensional image data has been registered to the navigation system, the user can manipulate the representation 1126 and select a target by picking a point on the surface of the representation. As also shown in FIG. 34A, the user can also employ the distance adjustment tool to advance and retract the medical device along a line normal to the surface of a selected target point.

Figure 49A:
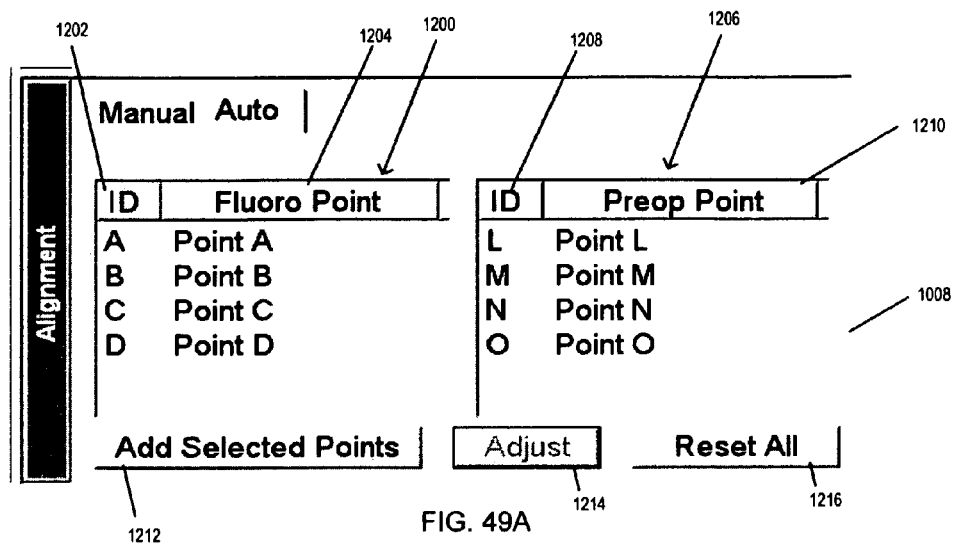
FIG. 49A is an enlarged view of Alignment window, shown in the auto mode.
Figure 49B:
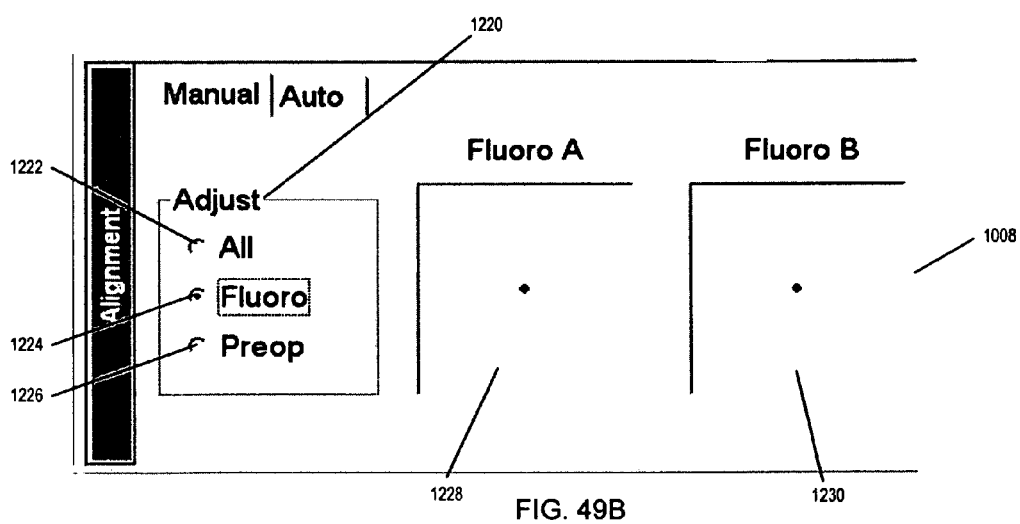
FIG. 49B is an enlarged view of the Alignment window, shown in the manual mode.

The alignment pane 1008 can be used to align or register the 3D image in pane 1014 with the x-ray image in pane 1016. As best shown in FIGS. 49A and 49B, the alignment pane has tabs to select between an auto (automatic) mode (FIG. 49A) and a manual mode (FIG. 49B). In the automatic mode shown in FIG. 49A, the pane has a fluoro point box 1200, with an ID column 1202 and a name column 1204, and a preop point box 1206 with an ID column 1208 and a name column 1210. In the auto mode, pane 1008 also includes an "Add Selected Points" button 1212, and "Adjust" button 1214, and a "Reset All" button 1216. The user selects point from the Points & Constellations pane 1004. The user picks a group from column 1026, and then selects one or more of the points in the group that are displayed on list 1036. Once a point has been selected, the point can be added to one of the lists (1202 or 1206) with the Add Selected Points button 1212. The user tries to mark the same points on both the anatomical display and the fluoro display. In the case of an EP procedure, an effective technique is to identify the highest (most superior) point in two or more of the pulmonary veins in each display. Once an appropriate number of corresponding points have been identified in both the anatomical and the x-ray views, the user can use the Adjust button 1024 to automatically find the best fit between the anatomical and x-ray views. If the match is not satisfactory (i.e. if the corresponding points from the x-ray view and the anatomical view are not satisfactorily aligned), the user can reset the points and start over with the Reset All button 1216. Alignment with the pane 1008 allows points and directions identified on the anatomical model to be displayed and used on the x-ray view, and vice versa. Thus the indicators in columns 1028 and 1030 in pane 1032 can be checked to display fluoro points, not just on the x-ray pane 1016, but also on the anatomical pane 1014, and to display anatomical points, not just on the anatomical pane 1016 but also on the x-ray pane 1016. As shown in FIG. 34A, the set of fluoro points indicated by yellow circles in the anatomical pane 1014 and the set of preoperative points indicated by red squares in the anatomical pane 1014 are fairly well aligned.

The automatic best fit alignment or registration can be implemented as a cost function optimization procedure. Since preoperative image points are being registered to X-ray or fluoro-localized points, a natural measure or cost function is the sum of the squared distances between corresponding points after a rigid transformation has been applied to one set of points, say the preoperative image points. The rigid transformation in general consists of a rotation and a translation. Standard algorithms such as the so-called Procrustes method can be used for this purpose. In some cases the three dimensional image data may not require further orientational corrections, in which case only a best-fit translation is required to implement the registration. In this latter case it can be mathematically shown that a best-fit registration is achieved by matching the centroids of the 2 sets of points (the preoperative image set and the fluoro-localized set); thus the distance vector between the corresponding centroids defines the requisite translation. Thus the "Adjust" button 1024 could implement any of these schemes. Other intensity-based schemes familiar to those skilled in the art could also be used for the automatic registration process.

As shown in FIG. 49B, in the manual mode the pane 1008, has an adjust box 1220 with an "All" pick button 1222, a "Fluoro" pick button 1224, a "Preop" pick button 1226. The pane 1008 also has a "Fluoro A" button 1228 and a "Fluoro B" button 1230. The user can select the "Fluoro" pick button 1228, and then move the fluoro points displayed on the preoperative anatomical image in pane 1014. The user can also select the "Preop" pick button 1224, and then move the preop points displayed on the x-ray fluoroscopic image in pane 1016. Finally the user can select the "All" button, and then move the preop points displayed on the x-ray fluoroscopic image in pane 1016 and/or the fluoro points displayed on the preoperative anatomical image in pane 1014. The user can use the Fluoro A and Fluoro B buttons 1228 and 1230, which preferably display thumbnail images, to switch the image that user uses to align with the preoperative image points.

FIG. 34B is a view of the display 1000 similar to the view in FIG. 34A, except that the button 1070 has been pressed to display object 1058 cut in half by a plane in order to display the interior rather than the exterior of the object. The object 1058 has also been rotated slightly in FIG. 34B from FIG.

Figure 40:
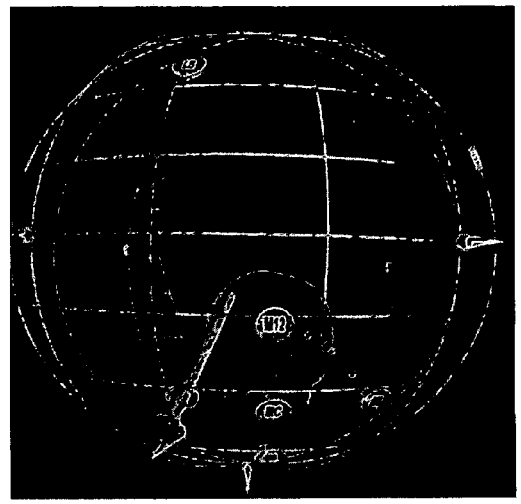
FIG. 40 is a view of the spherical navigation mode of the preferred embodiment of the user interface.
Figure 41:
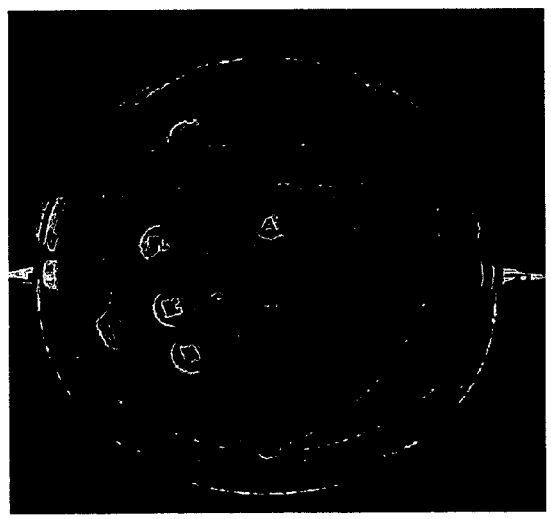
FIG. 41 is a view of the spherical navigation mode of the preferred embodiment.
Figure 42:
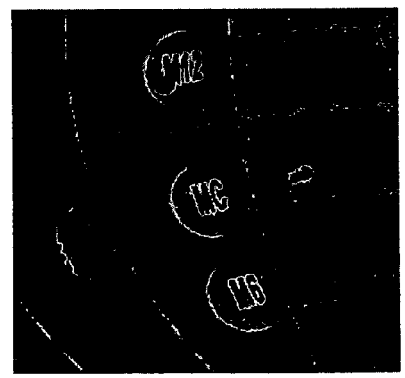
FIG. 42 is an enlarged partial view of the spherical object used in the spherical object navigation mode of the preferred embodiment of the present invention.

34A. As shown in pane 1018 in FIG. 34B, the inside view is preferably taken along a vertical plane through the point of rotation of the object 1058. The outside of the object 1058 is shown in FIG. 40, the inside of the object 1058 (rotated from FIG. 40) is shown in FIG. 41, and the standard user directions, several user selected directions, and the desired field direction are shown in the enlarged inside view of the object in FIG. 42.

Figure 43A:
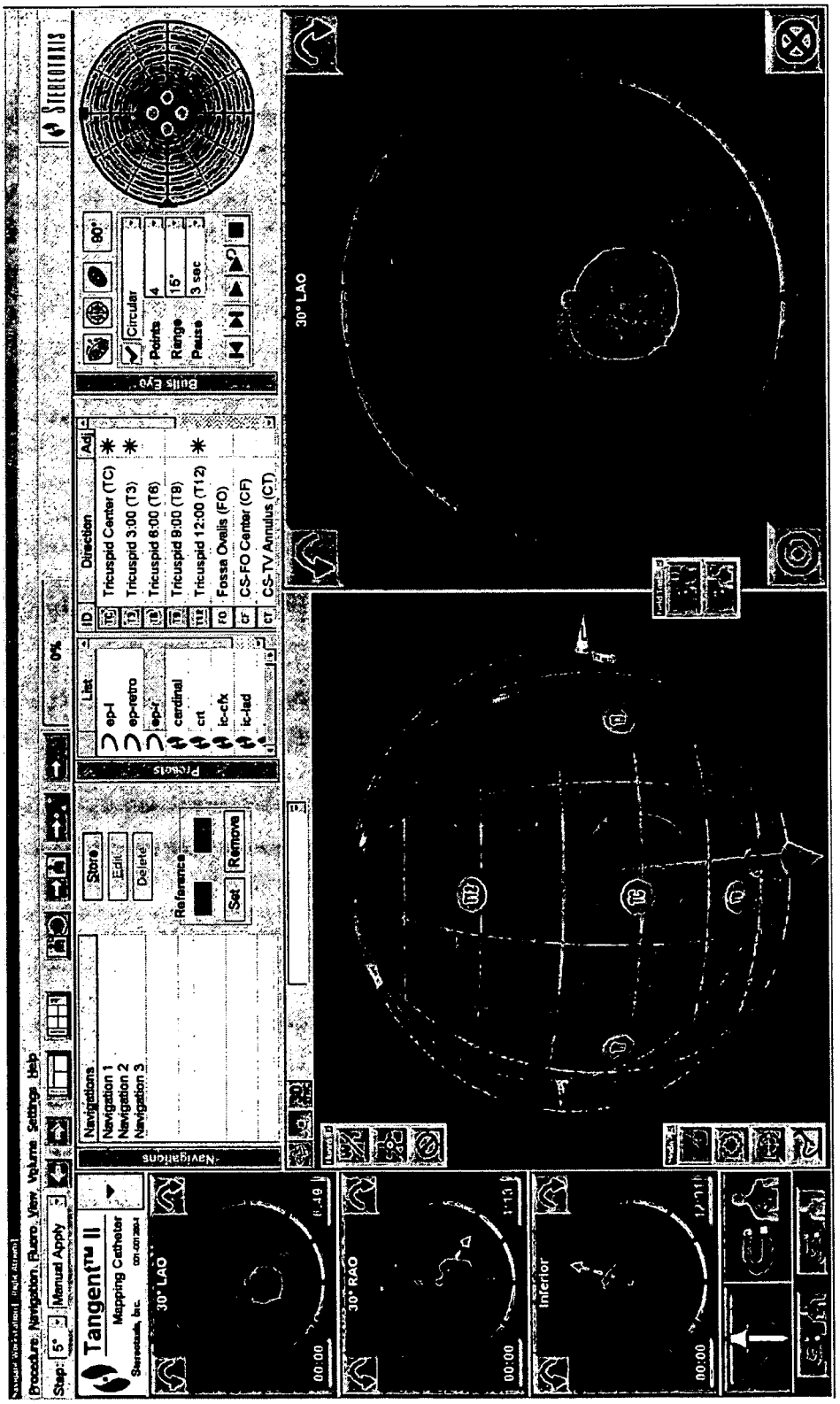
FIG. 43A is a view of a display from the EP mode of the fourth preferred embodiment of a user interface, in the right atrium mode.

FIG. 43A is another view of the display 1000 configured by the user with button 814, and selecting 2D Pane 1002, Navigations pane 1250, Presets pane 1006, and Bull's Eye pane 834. The user has also selected the object navigation pane 1018, and the 30° LAO subpane from the 2D pane 1002. In the object navigations pane, the user has selected (for example by right clicking on the representation 1058 of the object) to display a representation of the right atrium inside the representation 1058 of the object.

The Navigations pane 1250 is adapted for storing and displaying defined directions. As shown in FIG. 43A, the Navigations pane 1250 includes a "Navigations" list 1252 for listing various user defined directions. The Navigations pane 1250 also includes a "Store" button 1254, an "Edit" button 1256, and a "Delete" button 1258. In this preferred embodiment, the Store button 1254 stores the current direction of the magnetic field, although when used with a non-magnetic navigation system it might simply store the current direction of the medical device. The Edit button allows the user to edit the name of a previously stored point on the Navigations list 1252. The Navigations pane 1250 also includes a "Reference" box 1260. The navigations box 1260 has two indicator windows 1262 and 1264 for setting identifying information about a stored user-defined direction. For example, the user can right click on the window to 1262 and 1264 to select color and shape, respectively, or the windows 1262 and 1264 could be set up to receive text labels entered, for example with a keyboard. The reference box 1260 also includes a "Set" button 1266 to set the selected identifiers in the windows 1262 and 1264 for a selected direction highlighted on the Navigations list 1252. The reference box 1260 preferably also includes a "Remove" button to remove the identifiers for a selected direction highlighted on the Navigations list 1252.

The Bull's Eye pane 834 is adapted for manually or automatically adjusting the distal tip of the medical device.

Figure 43B:
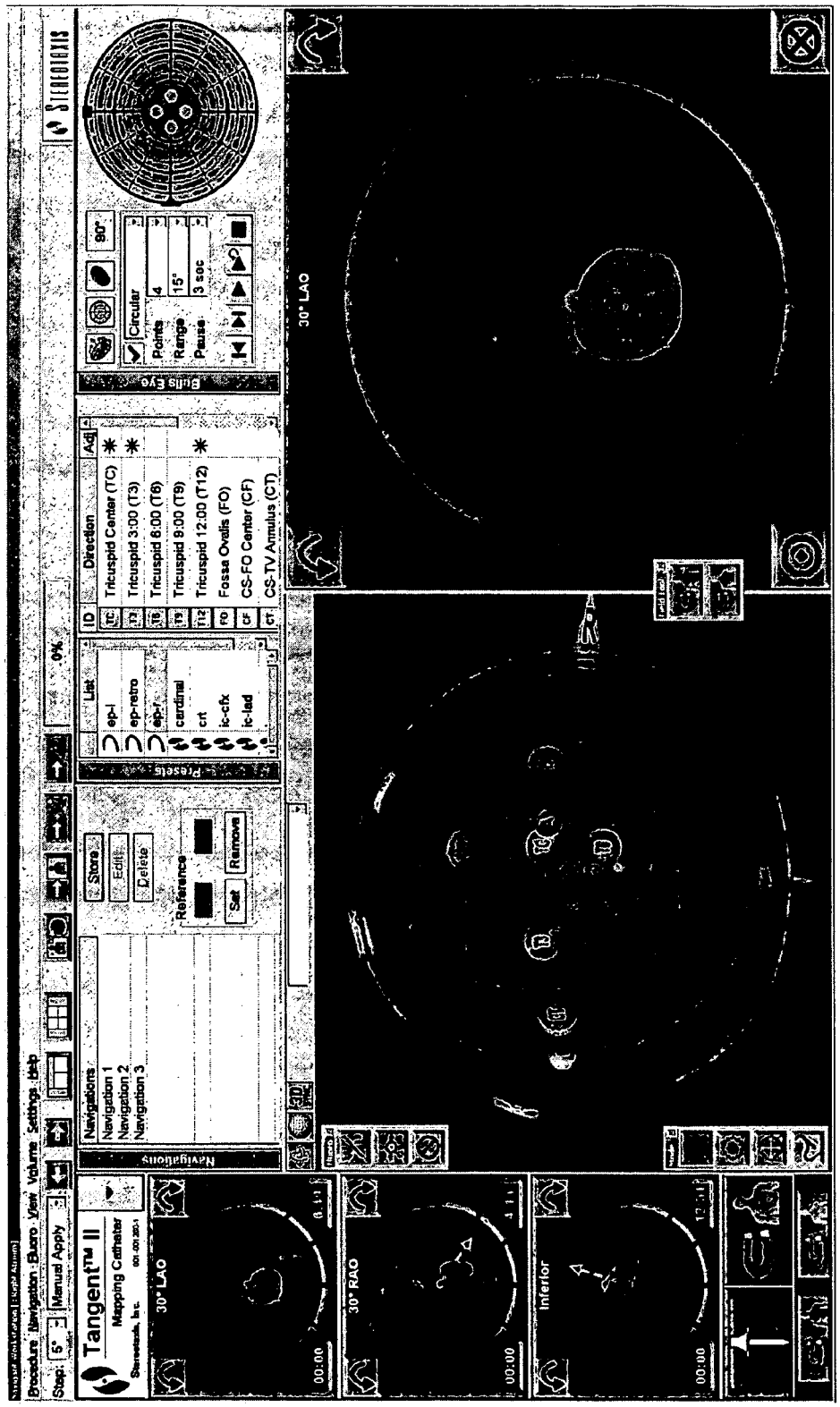
FIG. 43B is a view of an alternative to the display of FIG. 43A.

FIG. 43B is a view similar to FIG. 43A, except that the sphere/hemisphere button has been operated in FIG. 43B to show the interior of object 1058, and the object has been rotated.

Figure 44:
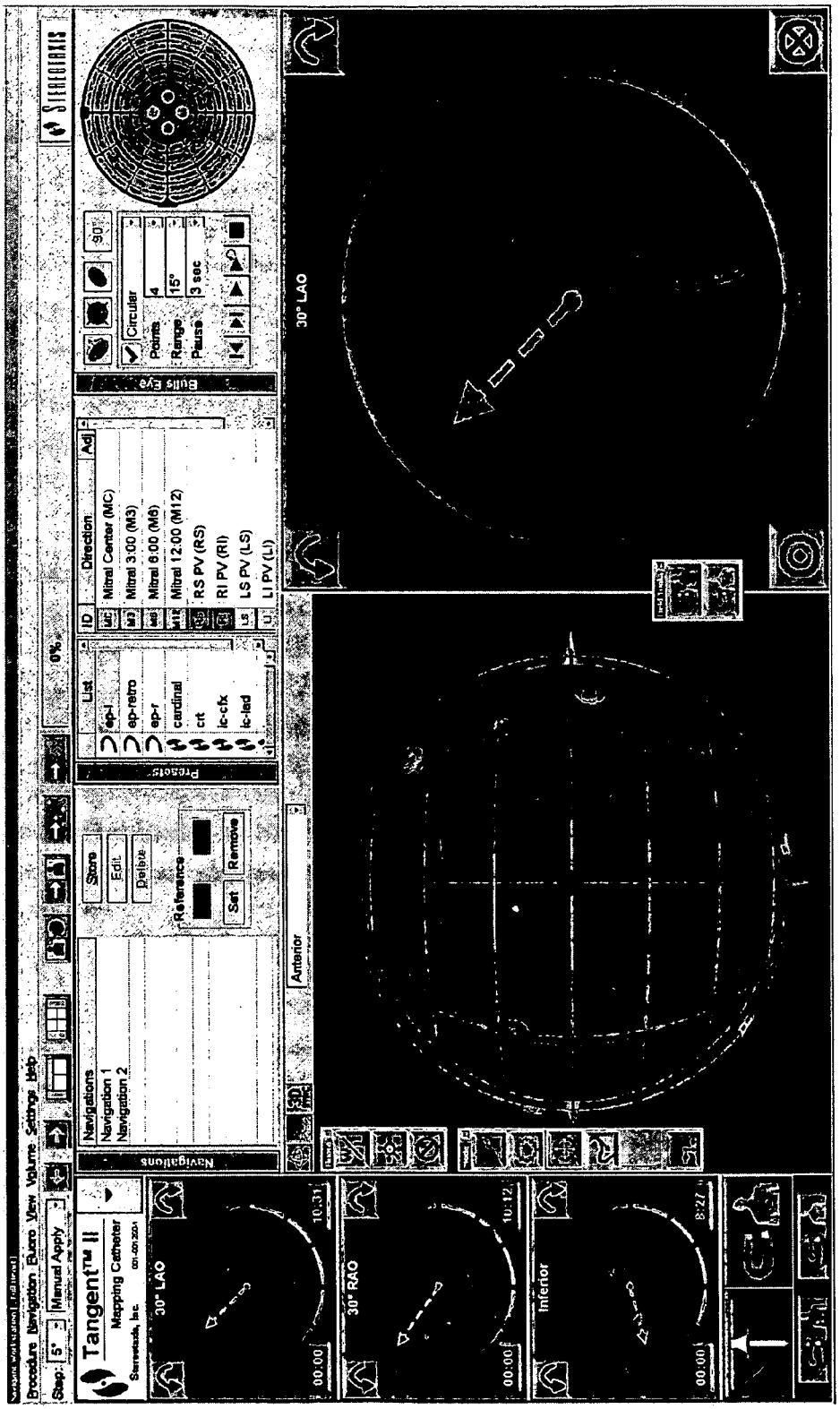
FIG. 44 is a view of a display from the EP mode of the fourth preferred embodiment of a user interface, in the full heart mode.

FIG. 44 is another view of the display 1000 configured by the user with button 814, and selecting 2D Pane 1002, Navigations pane 1250, Presets pane 1006, and Bull's Eye pane 834. The user has also selected the object navigation pane 1018, and the 30° LAO subpane from the 2D pane 1002. In the object navigations pane 1018, the user has selected (for example by right clicking on the representation 1058 of the object) to display a representation of the entire heart inside the representation of the object.

The Navigations pane 1250 is adapted for storing and displaying user-defined directions. The Presets pane 1006 is adapted for recalling various preset directions and sets of directions. The Bull's Eye pane 834 is adapted for manually pr automatically adjusting the distal tip of the medical device.

Figure 45A:
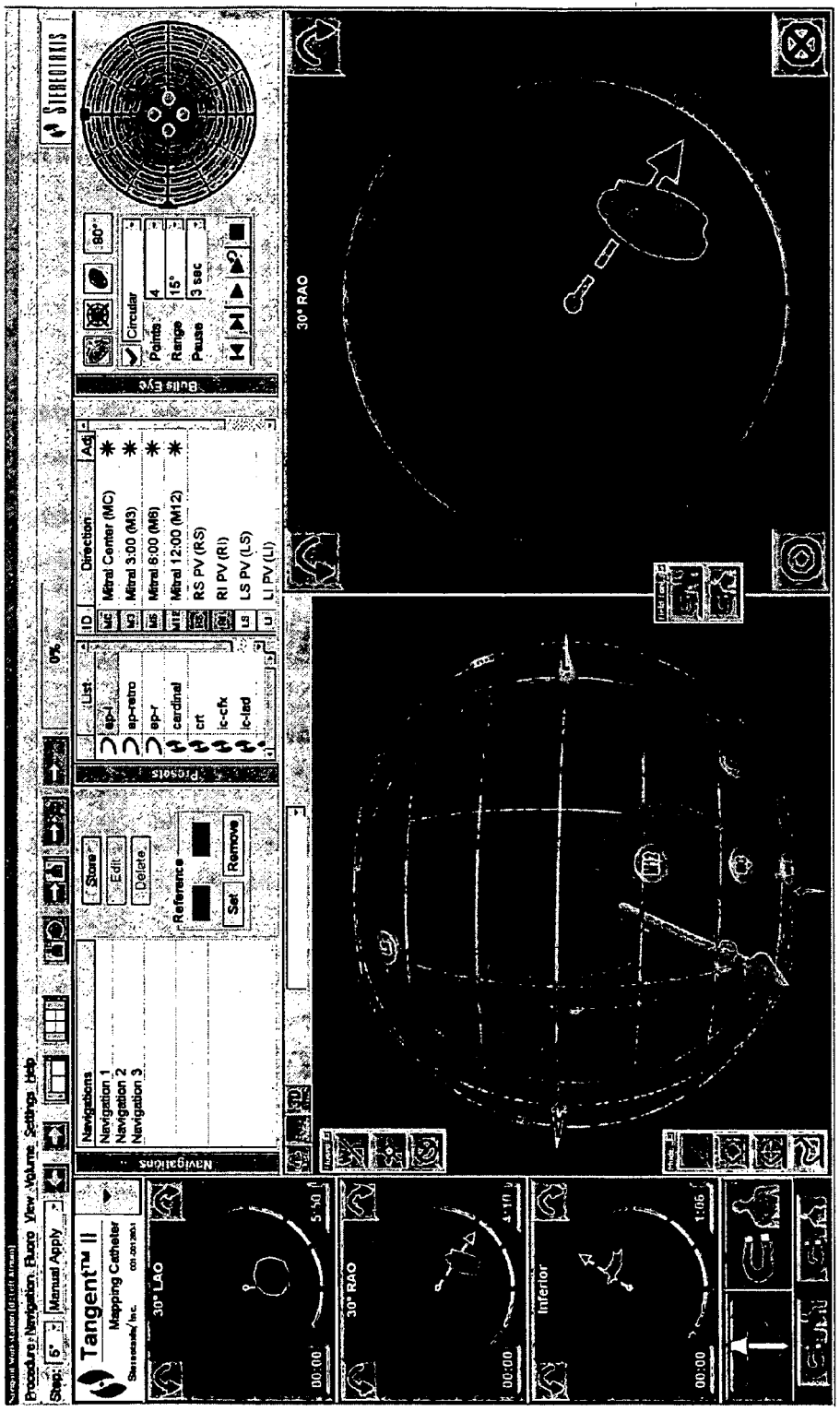
FIG. 45A a view of a display from the EP mode of the fourth preferred embodiment of a user interface, in the left atrium mode.

FIG. 45A is another view of the display 1000 configured by the user with button 814, and selecting 2D Pane 1002, Navigations pane 1250, Presets pane 1006, and Bull's Eye pane 834. The user has also selected the object navigation pane 1018, and the 30° RAO subpane from the 2D pane 1002. In the object navigations pane 1018, the user has selected (for example by right clicking on the representation 1058 of the object) to display a representation of the left atrium inside the representation of the object.

The Navigations pane 1250 is adapted for storing and displaying defined directions. The Presets pane 1006 is adapted for recalling various preset directions and sets of directions. The Bull's Eye pane 834 is adapted for manually or automatically adjusting the distal tip of the medical device.

Figure 45B:
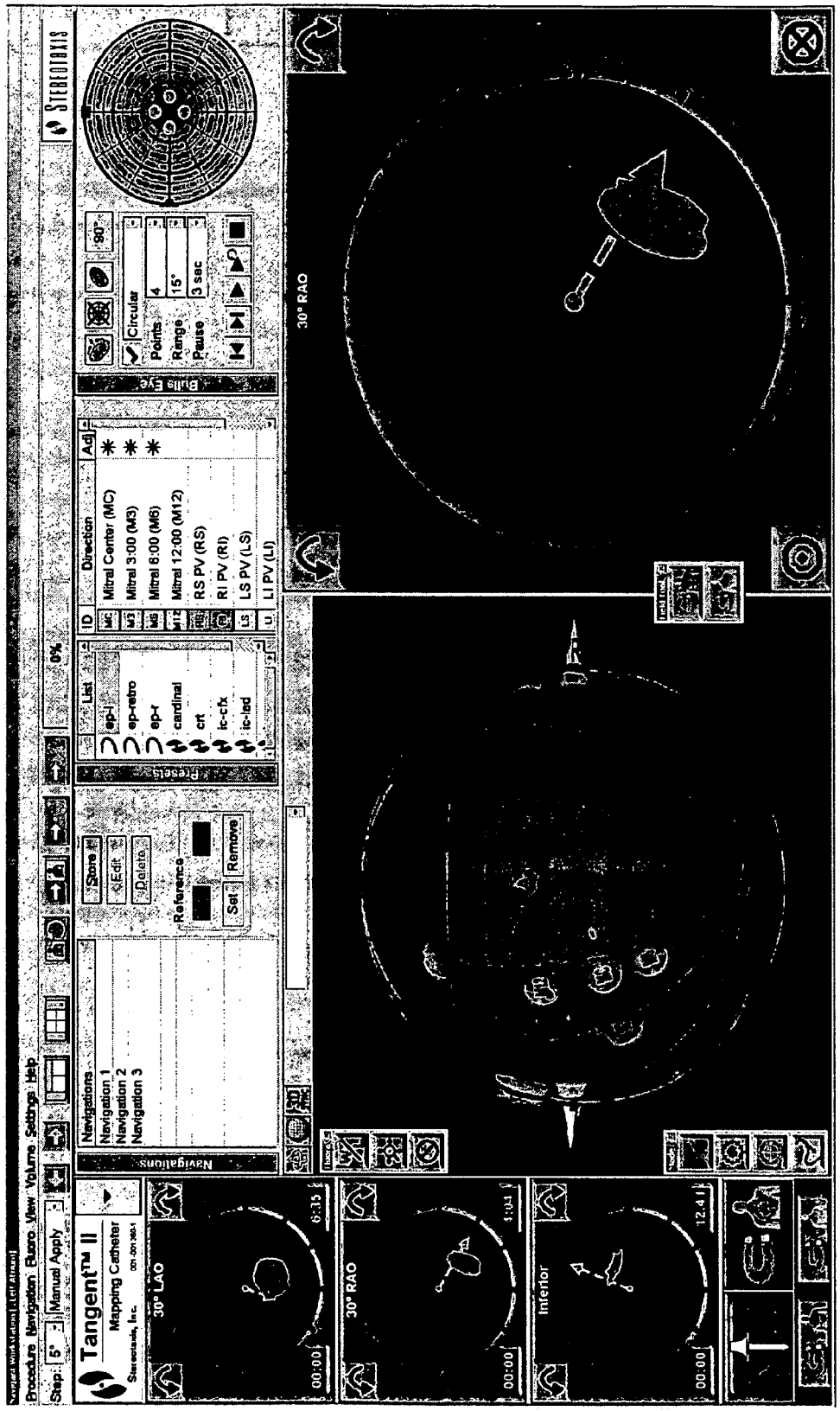
FIG. 45B is a view of an alternative to the display of FIG. 45A.

FIG. 45B is a view similar to FIG. 45A, except that the sphere/hemisphere button has been operated in FIG. 45B to show the interior of the representation 1058 of the object, and the object is shown rotated.

Figure 46:
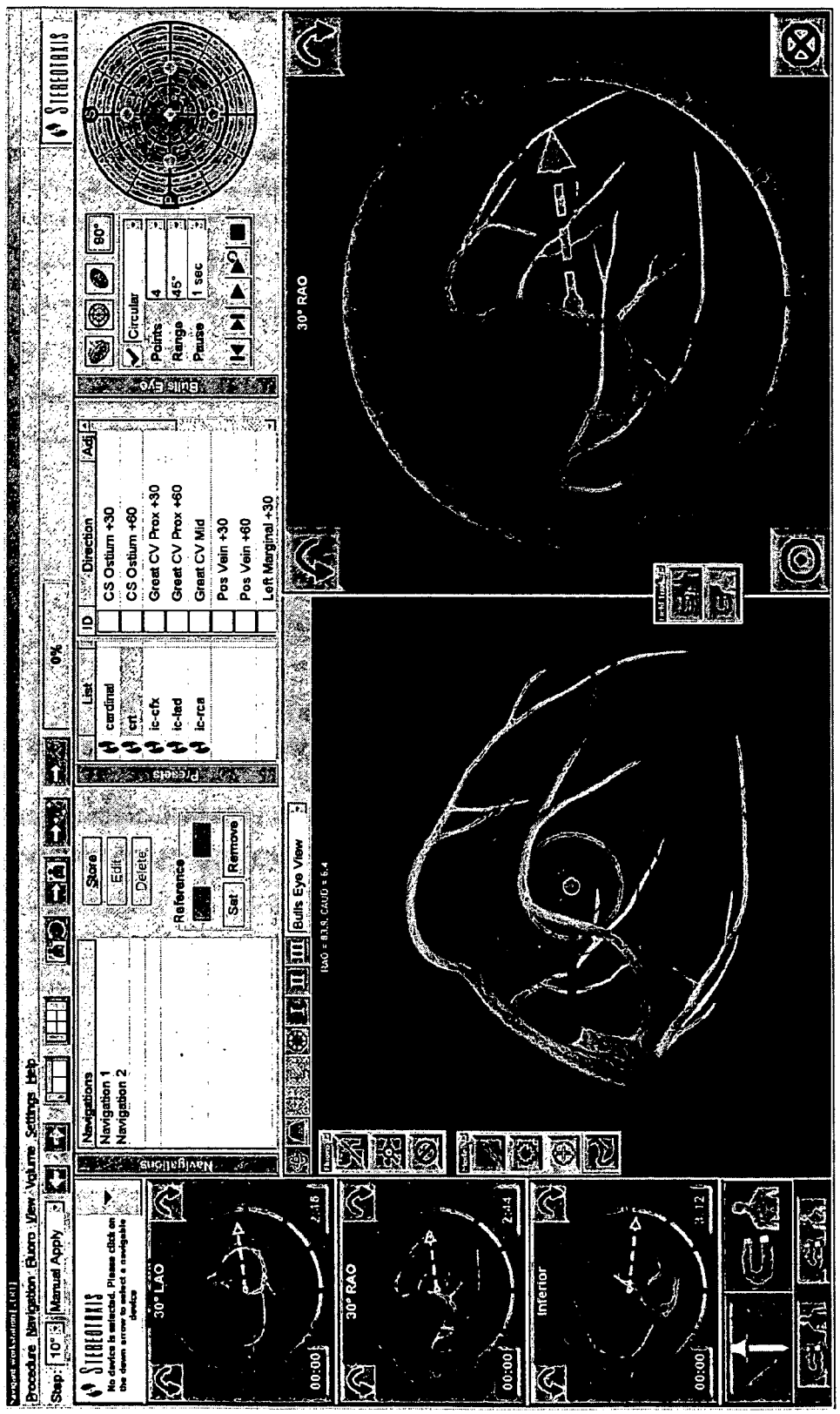
FIG. 46 is a view of a display from the CRT mode of the preferred embodiment of the user interface.

FIG. 46 is a view of a display 1300 from the CRT mode of the preferred embodiment of the user interface, selected by operating button 708 on the menu 700 in FIG. 32. The display 1300 is similar to the display 1000 and corresponding parts are identified with corresponding reference numerals. The user has configured the display 1300 with button 814, and selecting 2D Pane 1002, Navigations pane 1252, Presets pane 1006, and Bull's Eye pane 834. The user has also selected the object navigation pane 1018, and the 30° LAO subpane from the 2D pane 1002. In the object navigations pane 1018, the user has selected (for example by right clicking on the representation 1058 of the object) to display a representation of the right atrium inside the representation 1058 of the object.

Figure 47:
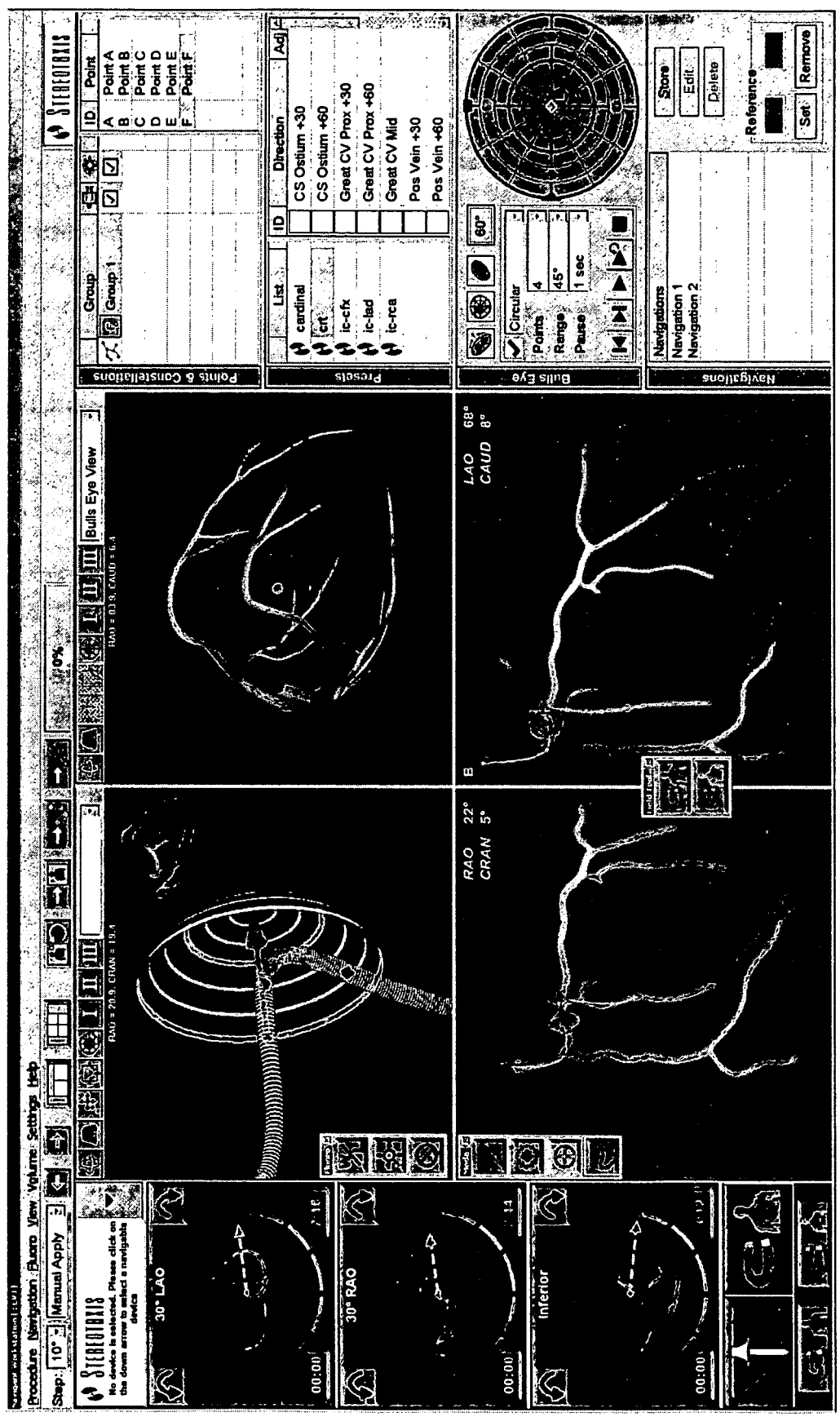
FIG. 47 is an alternate view of a display from the CRT mode of the preferred embodiment of the user interface

FIG. 47 is a view of a display 1300 from the CRT mode of the preferred embodiment of the user interface, selected by operating button 708 on the menu 700 in FIG. 32. The display 1300 is similar to the display 1000 and corresponding parts are identified with corresponding reference numerals. The user has configured the display 1300 with button 816, and selecting 2D Pane 1002, "Points & Constellations" pane 1004, Presets pane 1006, Bull's Eye pane 834, and Navigations pane 1250. The user has also selected the 3D pane 1012, the preoperative anatomical pane 1014 (which in FIG. 47 shows the venous structure of the heart), and two fluoro panes 1066 to display the RAO and LAO images of the operating region.

As shown in FIG. 47, a vessel grouping is also possible in the Points and Constellations pane 1004. In the vessel grouping a series of points are joined as a continuous path, as a blood vessel. The user can use columns 1028 and 1030 to elect to display the vessel grouping on the images in the fluoro panes 1066, and on the 3D pane 1012. As shown in FIG. 47, a vessel grouping 1400 is displayed in both fluoro panes 1066, and in the 3D pane 1012. The user can pick a direction parallel to the longitudinal axis of the vessel grouping simply by selecting a point on the vessel grouping. This is useful in navigating through vessels. As shown in FIG. 47, the Bull's Eye pane 834 is in use so that the user can conveniently alter the indicated desired direction from the tangential direction to the vessel grouping.

Figure 48A:
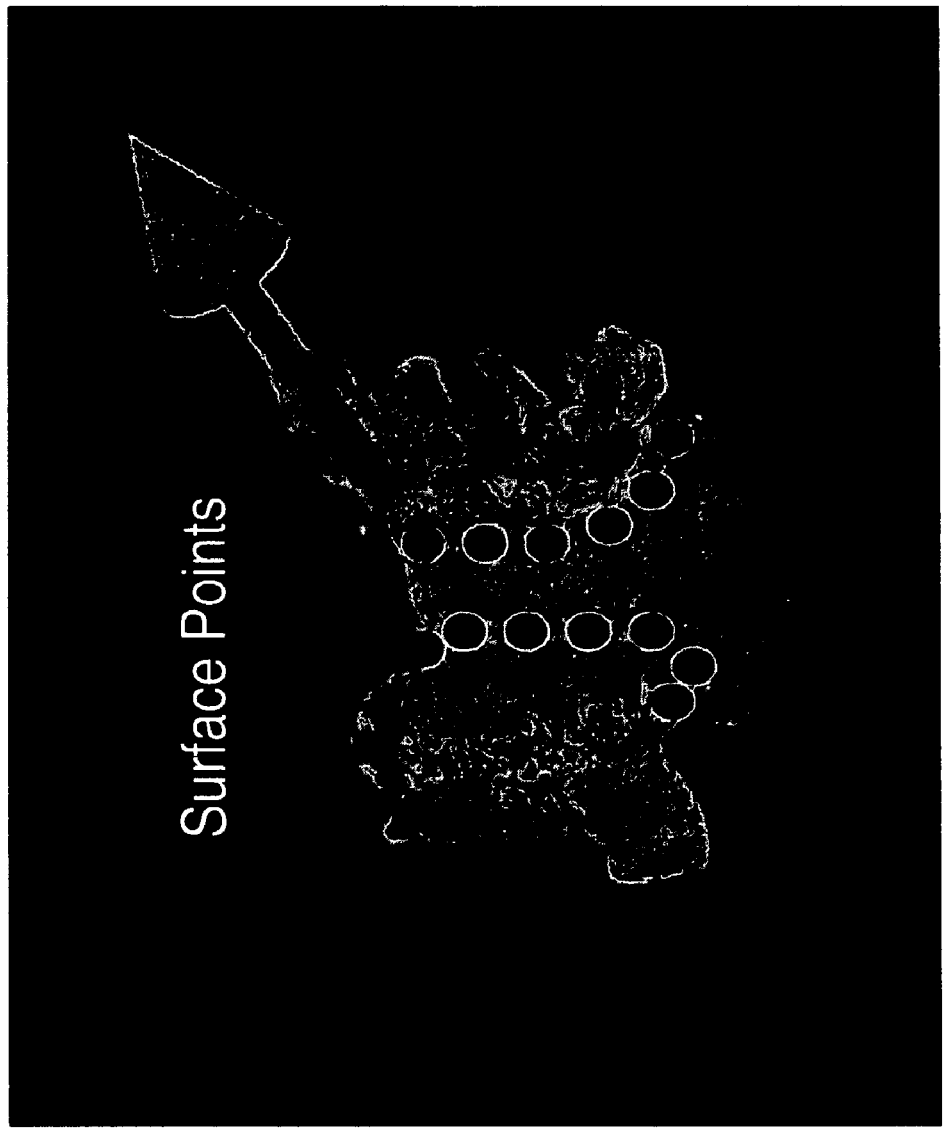
FIG. 48A is a view of the display of an anatomical object navigation mode.
Figure 48B:
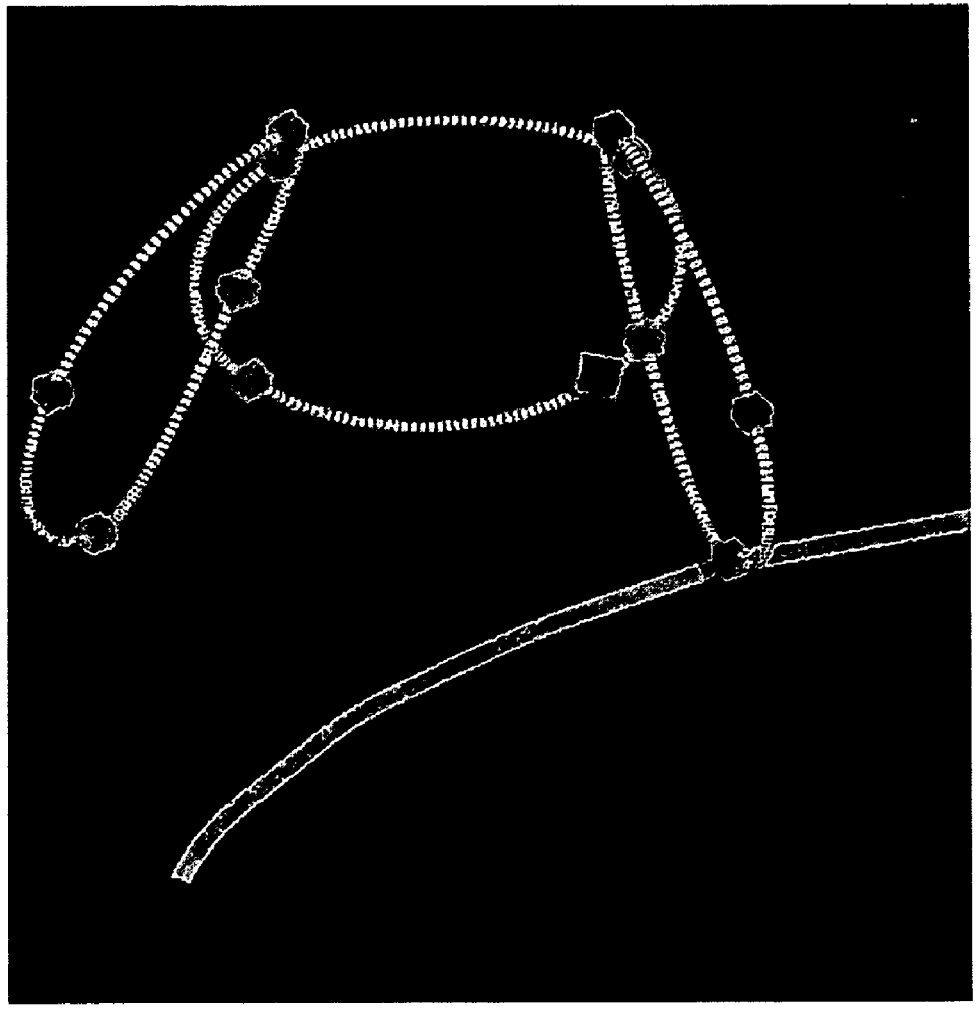
FIG. 48B is an alternate view of the selections made.

FIG. 48A is a view of the display of an anatomical object navigation pane 1014. The user can identify points on the surface of the anatomical object 1126 by manipulating the object and pointing and clicking on points on its surface. These points can be grouped as constellations, for example splines, 1402, 1404, 1404, and displayed on a 3D pane 1012. This facilitates visualization of the points selected directly from subject-derived anatomy.

While discussed above with respect to controlling a magnetic navigation system, it should be understood that any of the interfaces described above can be used to control any system for remotely orienting the distal end of an elongate device, including but not limited to medical devices such as catheters and guide wires.

What is claimed is:

1. An interface device for controlling a magnetic navigation system that applies a magnetic field in a selected direction to an operating region in a subject to magnetically orient a medical device in the operating region, the interface comprising:
   a display on which at least one image of the operating region is displayed;
   an input device for identifying on the at least one image on the display a plurality of points along the subject's vasculature in an image of the operating region in the subject, to establish a predetermined branched path through the subject's vasculature, and for identifying an identified navigation point in the operating region on the at least one image on the display;
   a processor for detecting the input of an identified point, where in response to detecting said input the processor responds by determining an application point in the operating region on a predetermined branched path through the subject's vasculature that is closest to the identified point, and generates a command causing the magnetic navigation system to apply a magnetic field at the application point, in a direction tangent to the predetermined path at the application point, to thereby magnetically orient a medical device in the operating region towards the identified point.

2. The interface according to claim 1, wherein there are at least two images of the operating region in different planes on the display, and wherein the input device comprises a device for moving an indicator over each image of the operating region and for selecting a point on the image indicated by the indicator.

3. The interface according to claim 1 wherein the display displays at least two images of the operating region, and wherein the input moves a cursor in each of the at least two images to identify a point in the operating region of the subject.

4. The interface according to claim 1 wherein the predetermined branched path was manually identified.

5. The interface according to claim 1 wherein the predetermined branched path was determined from a plurality of points on the subject's vasculature identified on the at least one image of the operating region on the display.

6. The interface according to claim 5 wherein each point on the subject's vasculature was identified on at least two images of the operating region indifferent planes.

7. The interface according to claim 1 wherein the predetermined branched path was determined by automated processing of an image of the operating region.

8. The interface according to claim 1 wherein the predetermined branched path is superimposed over the image of the operating region on the display.

9. The interface according to claim 8 wherein each branch of the predetermined branched path is displayed in a different color.

10. A method of making a predetermined branched path through the vasculature in an operating region in a subjects vasculature, the method comprising:
    accepting the identification of a plurality of points on the subject's vasculature on at least one image of the operating region; and
    connecting each point with its nearest neighboring point to form the branched path through the vasculature;
    determining an application point on the branched path through the subject's vasculature in the operating region that is closest to the selected point; and
    applying a magnetic field at the application point in a direction tangent to the navigable path at the application point.

11. The method according to claim 10 wherein each point is identified on at least two images of the operating region in different planes.

12. A method of operating a magnetic navigation system to apply a magnetic field in a selected direction in an operating region in a subject, to magnetically orient a medical device in the operating region, the method comprising:
    identifying a plurality of points along the subject's vasculature in an image of the operating region in the subject;
    connecting each point to the closest adjacent point to create a network of navigable paths through the subject's vasculature;
    identifying a selected point on an image of the operating region, and identifying an application point that is on the network of navigable paths, closest to the selected point; and applying a magnetic field at the application point in a direction tangent to the navigable path at the application point.

13. The method according to claim 12 wherein the step of identifying a plurality of points on an image of the operating region comprises identifying each point on at least two images of the operating region in different planes.

14. The method according to claim 12 wherein the step of identifying a selected point comprises identifying the selected point on at least two images of the operating region in different planes.

15. A method of operating a magnetic navigation system to apply a magnetic field in a selected direction in an operating region in a subject to magnetically orient a medical device in the operating region the method comprising:
    identifying a selected point on an image of the operating region;
    determining an application point on a predetermined navigable path through the subject's vasculature in the operating region corresponding that is closest to the selected point; and
    applying a magnetic field at the application point in a direction tangent to the navigable path at the application point.

16. The method according to claim 15 wherein the step of identifying a selected point comprises identifying the selected point on two images of the operating region in different planes.

17. The method according to claim 15 wherein the predetermined navigable path is created by identifying points on the vasculature on an image of the operating region, and connecting each point to the closest adjacent points to create the navigable paths.

18. A method of controlling a magnetic navigation system to apply a magnetic field in a selected direction in an operating region in a subject to magnetically orient a medical device in the operating region the method comprising:
    accepting the identification of a selected point on an image of the operating region;
    determining an application point on a predetermined navigable path through the subject's vasculature in the operating region corresponding that is closest to the selected point; and
    applying a magnetic field at the application point in a direction tangent to the navigable path at the application point.

19. The method according to claim 18 wherein the step of accepting the identification a selected point comprises accepting the identification of the point on two images of the operating region in different planes.

20. The method according to claim 18 wherein the predetermined navigable path is created by accepting the identification of points on the vasculature on two image of the operating region in different planes, and connecting each point to the closest adjacent points to create the navigable paths.

21. A magnetic navigation system that applies a magnetic field in a selected direction to an operating region in a subject to magnetically orient a medical device in the operating region, the system comprising:

at least one magnet;
 an interface for controlling the at least one magnet, including:
 a display on which at least one image of the operating region is displayed;
 an input device for identifying a point in the operating region on the at least one image on the display;
 a processor for determining an application point in the operating region on a predetermined branched path through the subject's vasculature that is closest to the identified point, and causing the magnet to apply a magnetic field at the application point, in a direction tangent to the predetermined path at the application point.

22. The magnetic navigation system of claim 21 wherein there are at least two magnets, arid further comprising a movable support for each magnet to change the position and orientation of the each magnet to change the direction of the magnetic field applied to the operating region.

* * * * *